US007723574B2

(12) United States Patent
Zank et al.

(10) Patent No.: US 7,723,574 B2
(45) Date of Patent: May 25, 2010

(54) PROCESS FOR THE PRODUCTION OF Δ5-UNSATURATED FATTY ACIDS IN TRANSGENIC ORGANISMS

(75) Inventors: Thorsten Zank, Mannheim (DE); Johnathan A. Napier, Preston (GB); Olga Sayanova, St. Albans (GB)

(73) Assignee: BASF Plant Science GmbH, Ludwigshafen (DE)

( * ) Notice: Subject to any disclaimer, the term of this patent is extended or adjusted under 35 U.S.C. 154(b) by 604 days.

(21) Appl. No.: 11/603,557

(22) Filed: Nov. 22, 2006

(65) Prior Publication Data
US 2007/0136892 A1 Jun. 14, 2007

(30) Foreign Application Priority Data
Nov. 24, 2005 (GB) .................................. 0523915.7
Nov. 30, 2005 (GB) .................................. 0524420.7
Jun. 19, 2006 (GB) .................................. 0612109.9

(51) Int. Cl.
*A01H 5/00* (2006.01)
*C12N 15/82* (2006.01)
*C07H 21/04* (2006.01)
(52) U.S. Cl. ........................ 800/298; 800/281; 536/23.2
(58) Field of Classification Search ........................ None
See application file for complete search history.

(56) References Cited

U.S. PATENT DOCUMENTS

| 6,459,018 | B1 | 10/2002 | Knutzon |
| 6,762,345 | B1 * | 7/2004 | Cahoon et al. ............... 800/281 |
| 2007/0028326 | A1 | 2/2007 | Cirpus et al. |

FOREIGN PATENT DOCUMENTS

| WO | WO-98/46765 | 10/1998 |
| WO | WO-99/49050 | 9/1999 |
| WO | WO-03/093482 | 11/2003 |
| WO | WO-2005/012316 A2 | 2/2005 |

OTHER PUBLICATIONS

Asset, G., et al., "Effects of *Pinus pinaster* and *Pinus Koraiensis* Seed Oil Supplementation on Lipoprotein Metabolism in the Rat", Lipids, vol. 34, No. 1 (1999), pp. 39-44.
Berger, A., et al., "Epidermal Anti-Inflammatory Properties Of 5,11,14 20:3: Effects On Mouse Ear Edema, $PGE_2$ Levels In Cultured Keratinocytes, and PPAR Activation", Lipids in Health and Disease, vol. 1:5 (2002), pp. 1-12.
Cahoon, E.B., et al., "Production of Fatty Acid Components of Meadowfoam Oil in Somatic Soybean Embryos", Plant Physiology, vol. 124, (2000), pp. 243-251.
Destaillats, F., et al., "Regiospecific Analysis of Conifer Seed Triacylglycerols by Gas-Liquid Chromatography with Particular Emphasis on Δ5-Olefinic Acids", Lipids, vol. 36, No. 11 (2001), pp. 1247-1254.
Heilmann, I., et al., "Switching Desaturase Enzyme Specificity by Alternate Subcellular Targeting", PNAS, vol. 101, No. 28 (2004), pp. 10266-10271.
Marillia, E.-F., et al., "A Desaturase-like Protein from White Spruce is a '9 Desaturase", FEBS Letters, vol. 526, (2002), pp. 49-52.
Fukuchi-Mizutani, M., et al., "Characterization of Δ9 Acyl-lipid Desaturase Homologues from *Arabidopsis thaliana*", Plant Cell Physiol., vol. 39, No. 2 (1998), pp. 247-253.
Moreau, R.A., et al., "Properties of a Δ5-Fatty Acyl-CoA Desaturase in the Cotyledons of Developing *Limnanthes alba*", Archives of Biochemistry and Biophysics, vol. 209, No. 2 (1981), pp. 376-384.
Sakuradani, E., et al., "Δ6-Fatty Acid Desaturase From an Arachidonic Acid-producing *Mortierella* Fungus Gene Cloning and its Heterologous Expression in a Fungus, *Aspergillus*", Gene, vol. 238, (1999), pp. 445-453.
Smith, C.R., et al., "*Caltha palustris* L. Seed Oil. A Source of Four Fatty Acids with *cis*-5-Unsaturation", Lipids, vol. 3, No. 1 (1968), pp. 37-42.
Sprecher, H., "Metabolism of Highly Unsaturated *n*-3 and *n*-6 Fatty Acids", Biochimica et Biophysica Acta, vol. 1486, (2000), pp. 219-231.
Takeyama, H., et al., "Expression of the Eicosapentaenoic Acid Synthesis Gene Cluster from *Shewanella* sp. in a Transgenic Marine Cyanobacterium, *Synechococcus* sp.", Microbiology, vol. 143, (1997), pp. 2725-2731.
Tanaka, T., et al., "Metabolic Characterization of Sciadonic Acid (5c, 11c, 14c-eicosatrienoic acid) as an Effective Substitute for Arachidonate of Phosphatidylinositol", Eur. J. Biochem, vol. 268, (2001), pp. 4928-4939.
Tanaka, T., et al., "Non-methylene-Interrupted Polyunsaturated Fatty Acids: Effective Substitute for Arachidonate of Phosphatidylinositol", Biochemical and Biophysical Research Comm., vol. 264, (1999), pp. 683-688.
Tsevegsüren, N. et al., "Unusual Δ5*cis*-Fatty Acids in Seed Oils of *Cimicifuga* Species", J. High Resol., Chromatogr., vol. 20, (1997), pp. 237-241.
Whitney, H.M., et al., "Functional Characterisation of Two Cytochrome $b_5$-fusion Desaturases from *Anemone leveillei*: The Unexpected Identification of a Fatty Acid $Δ^6$-desaturase", Planta, vol. 217, (2003), pp. 983-992.
Wolff R.L., et al., "Abietoid Seed Fatty Acid Compositions-A Review of the *Genera Abies, Cedrus, Hesperopeuce, Keteleeria, Pseudolarix*, and *Tsuga* and Preliminary Inferences on the Taxomony of Pinaceae", Lipids, vol. 37, No. 1 (2002), pp. 17-26.
Wolff, R.L., et al., "Arachidonic, Eicosapentaenoic, and Biosynthetically Related Fatty Acids in the Seed Lipids from a Primitive Gymnosperm, *Agathis robusta*", Lipids, vol. 34, No. 10 (1999), pp. 1083-1097.
Wolff, R.L., et al., "Fatty Acid Composition of Pinaceae as Taxonomic Markers", Lipids, vol. 36, No. 5 (2001), pp. 439-451.
Yao, K., et al., "Expression of the *Arabidopsis ADS1* gene in *Brassica juncea* Results in a Decreased Level of Total Saturated Fatty Acids", Plant Biotechnology Journal, vol. 1, (2003), pp. 221-229.

(Continued)

*Primary Examiner*—Elizabeth F McElwain
(74) *Attorney, Agent, or Firm*—Connolly Bove Lodge & Hutz LLP

(57) ABSTRACT

A process for the production of Δ5-unsaturated fatty acids in transgenic organisms comprises transforming an organism with nucleic acid encoding a Δ5-desaturase.

30 Claims, 13 Drawing Sheets

OTHER PUBLICATIONS

Yu, R. et al., "Production of Eicosapentaenoic Acid by a Recombinant Marine Cyanobacterium, *Synechococcus* sp.", Lipids, vol. 35, No. 10 (2002), pp. 1061-1064.

Zank, T.K., et al., "Cloning and Functional Characterisation of an Enzyme Involved in the Elongation of Δ6-polyunsaturated Fatty Acids from the Moss *Physcomitrella patens*", The Plant Journal, vol. 31, No. 3 (2002), pp. 255-268.

U.S. Appl. No. 11/566,944, filed Jan. 1, 2006, Zank, et al.

Abbadi, A., et al., "Biosynthesis of Very-Long-Chain Polyunsaturated Fatty Acids in Transgenic Oilseeds: Constraints on Their Accumulation", The Plant Cell, vol. 16, No. 10, (2004), pp. 2734-2748.

Marillia, E.-F. et al., "Expression of Meadowfoam *Des5* and *FAE1* genes in Yeast and in Transgenic Soybean Somatic Embryos, and Their Roles in Fatty Acid Modification", Plant Physiology and Biochemistry, vol. 40, No. 10, (2002), pp. 821-828.

Napier, J.A., et al., "The Production of Long Chain Polyunsaturated Fatty Acids in Transgenic Plants by Reverse-Engineering", Biochimie, vol. 86, (2004) pp. 785-793.

Qi, B., et al., "Production of Very Long Chain Polyunsaturated Omega-3 and Omega-6 Fatty Acids in Plants", Nature Biotechnology, vol. 22, No. 6 (2004), pp. 739-745.

Wolff, R.L., et al., "General Characteristics of *Pinus* spp. Seed Fatty Acid Compositions, and Improtance of Δ 5-Olefinic Acids in the Taxonomy and Phylogeny of the Genus", Lipids, vol. 35, No. 1, (2000), pp. 1-22.

Wu, G., et al., "Stepwise Engineering to Produce High Yields of Very Long-Chain Polyunsaturated Fatty Acids in Plants", Nature Biotechnology, vol. 23, No. 8, (2005), pp. 1013-1017.

* cited by examiner

Figure 1

```
                          *         20          *         40          *         60          *         80
AL21     : ~~~~~~~~~~~~~~~~~~~~~~~~~~~~~~~~~~~~~~~~~~~~~~~~~~~~~~~~~~~~~~~~~~~~~~~~~MELPAMALQ-- :   9
AL10     : ~~~~~~~~~~~~~~~~~~~~~~~~~~~~~~~~~~~~~~~~~~~~~~~~~~~~~~~~~~~~~~~~~~~~~~~MDLTSMAMQET :  11
Cal2     : ~~~~MALIATTPKATFYPSSPYLRPTRRGNPKSISTYPKVPSSISFISKTNSSTICFPNTCLTLERRNKRCTRSISCSAA :  76
ADS1     : ~~~~~~~~~~~~~~~~~~~~~~~~~~~~~~~~~~~~~~~~~~~~~~~~~~~~~~~~~~~~~~~~~~~~~~~~~MSLSAS :   6
pined9   : MSALVLSLAPSTPARGGGESRFAEGKALRRRLNASSCNASSKNAQLMCERRILSWCYGIRRRNSAGLWGKATRVQV--SA :  78
limd5    : ~~~~~~~~~~~~~~~~~~~~~~~~~LRLSLYFPISISLSLSLEAMASFIATTTPAMPAFASVLDPKIPTKPEPKTETP :  53

*        100          *        120          *        140          *        160
AL21     : -SELKQDKFPS DUP KD T KITWV- VWNST FHIILVGGL VC SA F S SWL SLT Y-A CVPF T S :  86
AL10     : TAAAEEDRLPC E P KE T KITWV- PKWNST VFHILFIGGL VL LF ES F SKSEWVCFA Y-AIC VF T F :  89
Cal2     : TTGEDSGKIFL D  IRR-PQVYWG-PK NTVD ATGSVVLGM IL SLF AEF T S WS LSMAFV N-V T LF C F : 153
ADS1     : EKEENNKKMAADKAEMGR F  RAMCE-PK KRLD VKAFASLF PF CIL AP NF TMPA LRVALIVM-TVGGL GI VSV :  82
pined9   : VAEEEGGRILL D V KR R P PFLLEL E SLG I GAAGTVF M AL CLI AP FT TMRA E GVPAVLY-V T LL F S : 157
limd5    : KPKDDLERFRTC E W VLERRAHGP- M R RKMNPRE QNAVTLLVLHA AAMAP Y S D FWISFI LGFASSVL TCF : 131

*        180          *        200          *        220          *        240
AL21     : HPNLTHRSFKLEFIYLEYFFAIVELHAL QGDF VWMVSTHRYHHKET TYLLEHSFIEGFWFSHLFLEDSKYILEE-CFRY : 165
AL10     : HPNLTHRSFKLEPYLEYFAYVELHALNGD PID MVSTHRYHHOKC SERDFHSPLEGFWFCHIFLEDTS LT K-FVP : 168
Cal2     : HRNIAHKAPIDEWLEXIFAYCBACAQL GNPID MVSTHRYHHOKC SERDFHSPLEGFWFCHIFLED SLT K-FVP : 232
ADS1     : HFMILAHRSFR V DFWLEFAYCELLA DCGDPID MVSTHRYHHOET SDRIFHSPNEGFWFSHLLGLEDTGYLVEK-CCRR : 161
pined9   : HPNLSHRSFRDFIW DE LFAYCGVQA VQDPLDM VSTHRYHHEYCL SVKDEHSPNEGEWYSMSTM LEKTMPDR-V TR : 236
limd5    : HPCLTHGGFKLPRL VEXIFAYCGSLA QGDPME MVSNHRYHHQEV TERP VHSETQGFWFCHIGMVLDKDLFVEKRGEER : 211

*        260          *        280          *        300          *        320
AL21     : ELAG ILK SY REW LER P VPHVYLQAA L MPSGRPFIV GFA RTWGFHASWI VHSVCERYHQAMDTGDISTHL P : 245
AL10     : ELAG IMK SY REF LER T PVYHVYLQAA DLF PPFIAL G RVWVYHI LVMSAEHVHGSQSTM DILSRHL F : 248
Cal2     : NIVSDIEKFFAKFMERHYPLHPIALAN V AL S G IHKL EYLG RVWWVYHI LVNSAEHV HGSQSTM DILSRHLNW : 312
ADS1     : TLVEDIKR WY R  QRT VLYHILTFGFL YFBGLSFLT GIGIVAMEHVYC LINSLGHVW GSRTMKNL TGRIVHW : 241
pined9   : NIVSDLEMIPP R IRDLYIIPPIAMGLL AL GG P VINGMAVP WVYHI LVNSAAF V GYOALM TGDISRHWGW : 316
limd5    : NLV NLKRKAFSRFLQRE YMYFQLALIALLYVGGRE YIMLGFRLYFMFHSFAIHSVCRK GRPLMTGDISTHLMF : 291

*        340          *        360          *        380
AL21     : ILMITSEESWHIIIHHAFEYSARHCIEWWCITTT VEKLLEY GLATDVRVFS VHRRKLSPKNCVQDKQFCVNDK*      : 321
AL10     : IAMITSEESWHIIIHHAFEYSARHCIEWWCITTT IDKLLEY GLATEIRVFBEITHRRKMSPKN*~~~~~~~~~~~~~     : 312
Cal2     : VLLA  EESWHIIIHHAFESSARHCIEWWCILT TWTTVRILOAIGLATDVRVFSEVQIQRRTCFSE*~~~~~~~~~~     : 376
ADS1     : LSVFS ESWHIIIHHAFESSARQCIEWWCIIS ISWTIVRPLEIIGLATDVKLE SSQRRRMAMVR~~~~~~~~~~~~    : 305
pined9   : VEAHAFGESWHIIIHHAFCMSARHCIEWCFDPTEMVEKILEALGLARDVRAELEQHTTRSSSKPGL~~~~~~~~~~~~     : 382
limd5    : VFLCAFGESWHIIIHHAFECSARHCIEWMELIVTHMVERTLOAIGLATNVKLETAQIQKLKASA~~~~~~~~~~~~~~    : 356
```

Figure 3 (contd.)
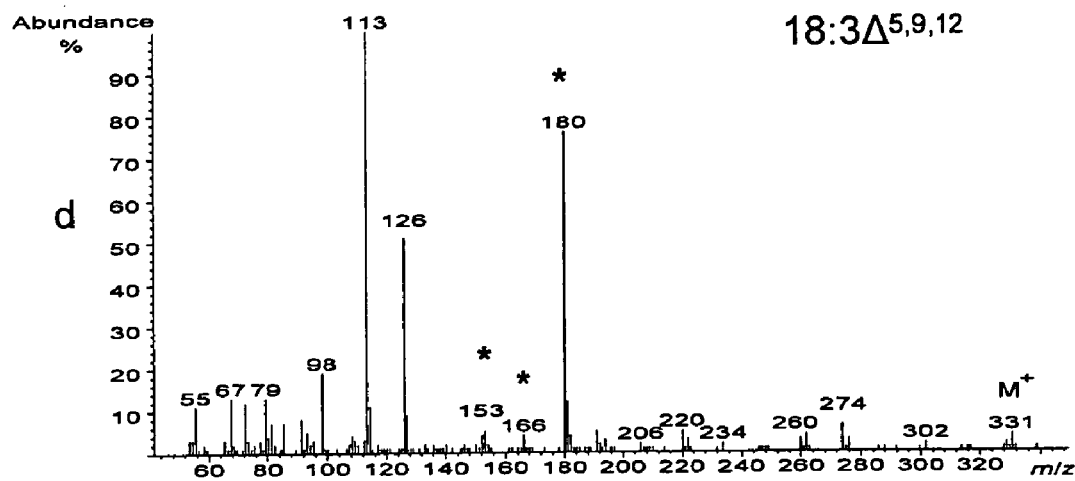
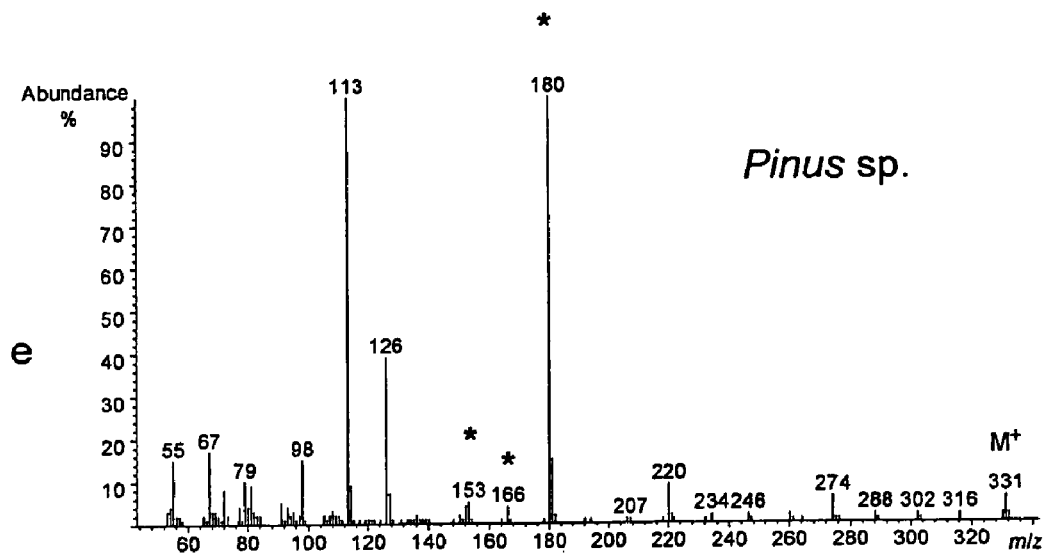

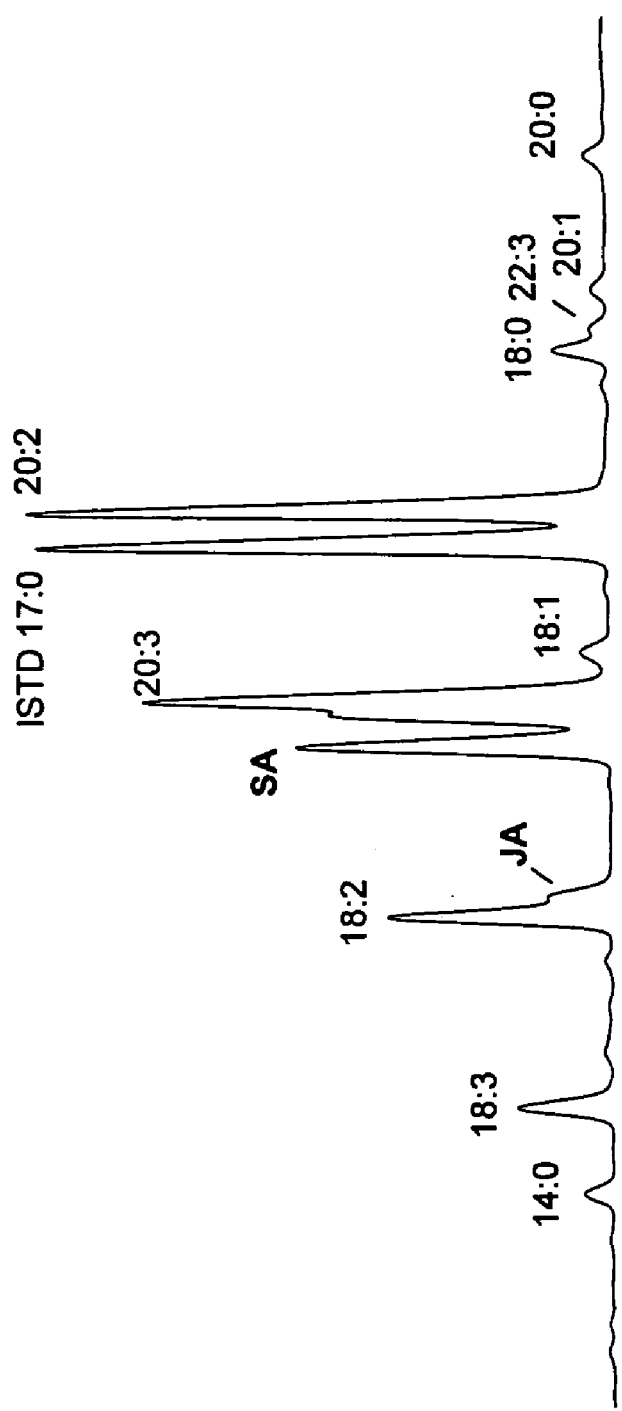
Figure 7 (contd.)

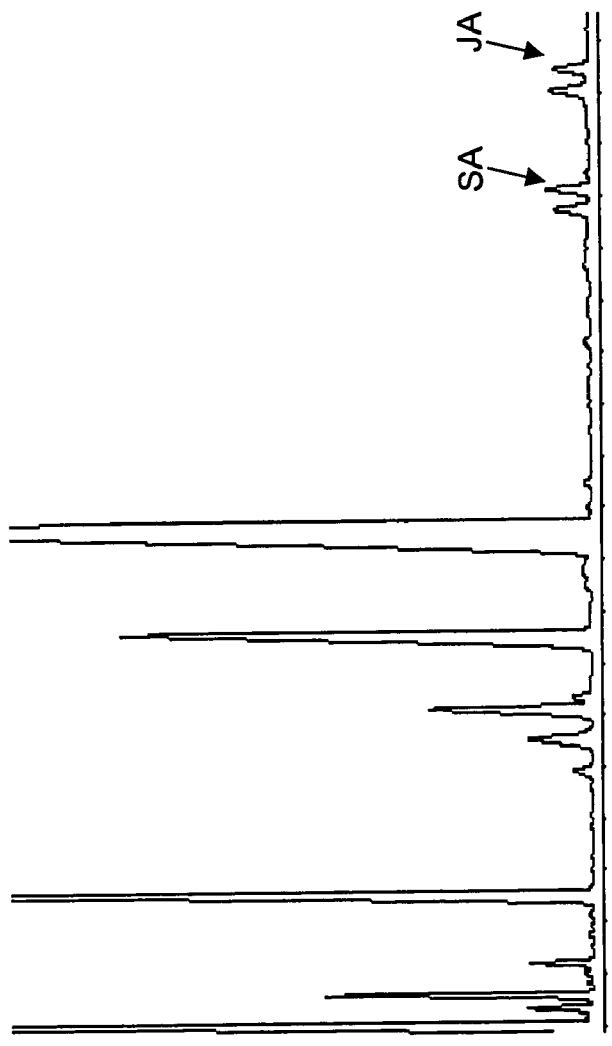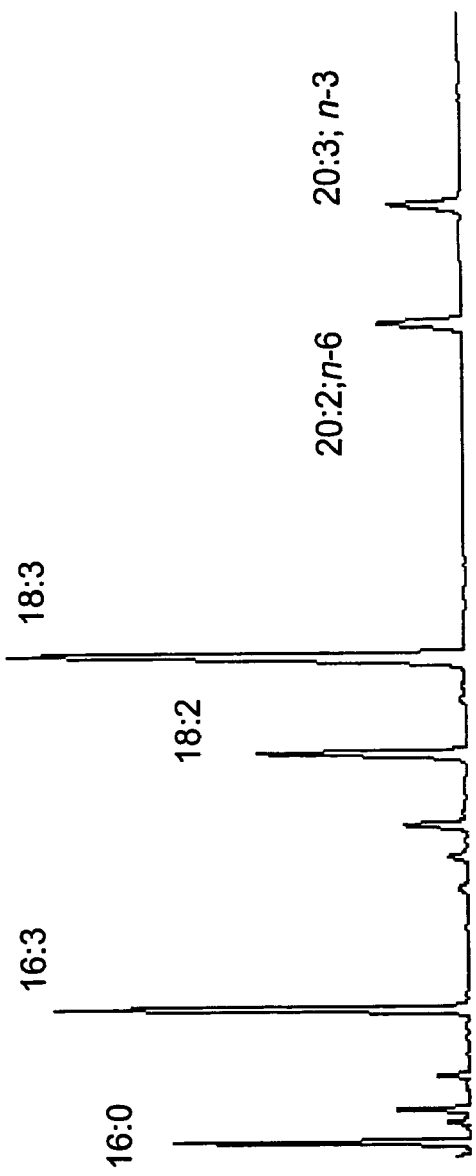
Figure 9a
Figure 9b

SEQUENCE LISTING

```
<160> NUMBER OF SEQ ID NOS: 25

<210> SEQ ID NO 1
<211> LENGTH: 1131
<212> TYPE: DNA
<213> ORGANISM: Caltha palustris
<220> FEATURE:
<221> NAME/KEY: CDS
<222> LOCATION: (1)..(1131)

<400> SEQUENCE: 1 atg gct cta att gca aca acc ccc aaa gcc aca ttc tat ccc tct tct      48
Met Ala Leu Ile Ala Thr Thr Pro Lys Ala Thr Phe Tyr Pro Ser Ser
1               5                   10                  15 cca tac ctt cgt cca act agg cgt gga aac ccc aaa tcc att tcc act      96
Pro Tyr Leu Arg Pro Thr Arg Arg Gly Asn Pro Lys Ser Ile Ser Thr
            20                  25                  30 tat ttc aaa gtt ttt tct tca att tca ttt att tcc aag aca aat tcc     144
Tyr Phe Lys Val Phe Ser Ser Ile Ser Phe Ile Ser Lys Thr Asn Ser
        35                  40                  45 agt acc att tgt ttt ccc aat act tgc cta act ttg gaa agg aga aac     192
Ser Thr Ile Cys Phe Pro Asn Thr Cys Leu Thr Leu Glu Arg Arg Asn
    50                  55                  60 aag aga tgt aca aga tcc ata tct tgt tcg gcg gcc aca act gga gaa     240
Lys Arg Cys Thr Arg Ser Ile Ser Cys Ser Ala Ala Thr Thr Gly Glu
65                  70                  75                  80 gac tcg ggg aag atc ttt tta tct gat gtg caa gtg ata cga cga cca     288
Asp Ser Gly Lys Ile Phe Leu Ser Asp Val Gln Val Ile Arg Arg Pro
                85                  90                  95
```

```
cag gtt tat tgg gga aga aaa tgg aac aca gta gat att gct act ggc      336
Gln Val Tyr Trp Gly Arg Lys Trp Asn Thr Val Asp Ile Ala Thr Gly
        100                 105                 110 tca gta gtc ttg ggg atg cac att ctg tcc ttg ttt gcc cct ttt aca      384
Ser Val Val Leu Gly Met His Ile Leu Ser Leu Phe Ala Pro Phe Thr
115                 120                 125 ttc agt tgg tct gca ctt agt atg gca ttc gtg ctt tat gtg gta aca      432
Phe Ser Trp Ser Ala Leu Ser Met Ala Phe Val Leu Tyr Val Val Thr
130                 135                 140 ggg ctg ttt ggg att act ctg tca tat cat aga aat ctt gct cat aaa      480
Gly Leu Phe Gly Ile Thr Leu Ser Tyr His Arg Asn Leu Ala His Lys
145                 150                 155                 160 gca ttc aag ctt cct aaa tgg ctt gaa tac tta ttt gca tat tgc ggg      528
Ala Phe Lys Leu Pro Lys Trp Leu Glu Tyr Leu Phe Ala Tyr Cys Gly
                165                 170                 175 gca cag gca ttg cag ggg aat cca att gat tgg gtt agt act cac agg      576
Ala Gln Ala Leu Gln Gly Asn Pro Ile Asp Trp Val Ser Thr His Arg
            180                 185                 190 tac cac cac cag ttc tgt gat tcc gaa aga gac cct cat agt cct ctt      624
Tyr His His Gln Phe Cys Asp Ser Glu Arg Asp Pro His Ser Pro Leu
        195                 200                 205 gaa gga ttc tgg ttc agt cat ata agt tgg ttc ttt gac acc aaa tct      672
Glu Gly Phe Trp Phe Ser His Ile Ser Trp Phe Phe Asp Thr Lys Ser
210                 215                 220 ctt act gag aag tgt gga gtg ccc aac aat gtg tct gat tta gag aag      720
Leu Thr Glu Lys Cys Gly Val Pro Asn Asn Val Ser Asp Leu Glu Lys
225                 230                 235                 240 caa cca ttc tac aaa ttt atg gaa aag aca tat cct ctt cat cca att      768
Gln Pro Phe Tyr Lys Phe Met Glu Lys Thr Tyr Pro Leu His Pro Ile
                245                 250                 255 gca ctt gca gct gtg cta tat gca cta gga gga ttt ccc ttt ctt gta      816
Ala Leu Ala Ala Val Leu Tyr Ala Leu Gly Gly Phe Pro Phe Leu Val
            260                 265                 270 tgg agc atg ggc gta agg gtt gta tgg gta tat cat att aca tgg ctc      864
Trp Ser Met Gly Val Arg Val Val Trp Val Tyr His Ile Thr Trp Leu
        275                 280                 285 gta aat tca gct tgt cat gta tgg gga agc cag tcg tgg aat acg ggc      912
Val Asn Ser Ala Cys His Val Trp Gly Ser Gln Ser Trp Asn Thr Gly
290                 295                 300 gac tta tct agg aac aac tgg tgg gtg gct ttg ctt gca ttt gga gag      960
Asp Leu Ser Arg Asn Asn Trp Trp Val Ala Leu Leu Ala Phe Gly Glu
305                 310                 315                 320 ggt tgg cat aac aat cac cat gca ttt gaa ttt tca gct cgg cat gga     1008
Gly Trp His Asn Asn His His Ala Phe Glu Phe Ser Ala Arg His Gly
                325                 330                 335 ttg gaa tgg tgg caa ctt gac ttg aca tgg tat act gta cga att ctt     1056
Leu Glu Trp Trp Gln Leu Asp Leu Thr Trp Tyr Thr Val Arg Ile Leu
            340                 345                 350 caa gca ctt gga ttg gcg aca gat gtg aaa gtt cca tcc gag gta cag     1104
Gln Ala Leu Gly Leu Ala Thr Asp Val Lys Val Pro Ser Glu Val Gln
        355                 360                 365 aag caa agg atg tgt ttc agc gag taa                                 1131
Lys Gln Arg Met Cys Phe Ser Glu
370                 375

<210> SEQ ID NO 2
<211> LENGTH: 376
<212> TYPE: PRT
<213> ORGANISM: Caltha palustris

<400> SEQUENCE: 2
```

```
Met Ala Leu Ile Ala Thr Thr Pro Lys Ala Thr Phe Tyr Pro Ser Ser
1               5                   10                  15

Pro Tyr Leu Arg Pro Thr Arg Arg Gly Asn Pro Lys Ser Ile Ser Thr
            20                  25                  30

Tyr Phe Lys Val Phe Ser Ser Ile Ser Phe Ile Ser Lys Thr Asn Ser
        35                  40                  45

Ser Thr Ile Cys Phe Pro Asn Thr Cys Leu Thr Leu Glu Arg Arg Asn
50                  55                  60

Lys Arg Cys Thr Arg Ser Ile Ser Cys Ser Ala Ala Thr Thr Gly Glu
65                  70                  75                  80

Asp Ser Gly Lys Ile Phe Leu Ser Asp Val Gln Val Ile Arg Arg Pro
                85                  90                  95

Gln Val Tyr Trp Gly Arg Lys Trp Asn Thr Val Asp Ile Ala Thr Gly
            100                 105                 110

Ser Val Val Leu Gly Met His Ile Leu Ser Leu Phe Ala Pro Phe Thr
            115                 120                 125

Phe Ser Trp Ser Ala Leu Ser Met Ala Phe Val Leu Tyr Val Val Thr
130                 135                 140

Gly Leu Phe Gly Ile Thr Leu Ser Tyr His Arg Asn Leu Ala His Lys
145                 150                 155                 160

Ala Phe Lys Leu Pro Lys Trp Leu Glu Tyr Leu Phe Ala Tyr Cys Gly
                165                 170                 175

Ala Gln Ala Leu Gln Gly Asn Pro Ile Asp Trp Val Ser Thr His Arg
            180                 185                 190

Tyr His His Gln Phe Cys Asp Ser Glu Arg Asp Pro His Ser Pro Leu
            195                 200                 205

Glu Gly Phe Trp Phe Ser His Ile Ser Trp Phe Phe Asp Thr Lys Ser
210                 215                 220

Leu Thr Glu Lys Cys Gly Val Pro Asn Val Ser Asp Leu Glu Lys
225                 230                 235                 240

Gln Pro Phe Tyr Lys Phe Met Glu Lys Thr Tyr Pro Leu His Pro Ile
            245                 250                 255

Ala Leu Ala Ala Val Leu Tyr Ala Leu Gly Gly Phe Pro Phe Leu Val
            260                 265                 270

Trp Ser Met Gly Val Arg Val Val Trp Val Tyr His Ile Thr Trp Leu
            275                 280                 285

Val Asn Ser Ala Cys His Val Trp Gly Ser Gln Ser Trp Asn Thr Gly
            290                 295                 300

Asp Leu Ser Arg Asn Asn Trp Trp Val Ala Leu Leu Ala Phe Gly Glu
305                 310                 315                 320

Gly Trp His Asn Asn His His Ala Phe Glu Phe Ser Ala Arg His Gly
                325                 330                 335

Leu Glu Trp Trp Gln Leu Asp Leu Thr Trp Tyr Thr Val Arg Ile Leu
            340                 345                 350

Gln Ala Leu Gly Leu Ala Thr Asp Val Lys Val Pro Ser Glu Val Gln
            355                 360                 365

Lys Gln Arg Met Cys Phe Ser Glu
370                 375

<210> SEQ ID NO 3
<211> LENGTH: 966
<212> TYPE: DNA
<213> ORGANISM: Anemone leveillei
<220> FEATURE:
```

```
<221> NAME/KEY: CDS
<222> LOCATION: (1)..(966)

<400> SEQUENCE: 3 atg gaa ctc cca gcg atg gcg ttg caa agt gaa cta aag caa gac aaa      48
Met Glu Leu Pro Ala Met Ala Leu Gln Ser Glu Leu Lys Gln Asp Lys
1               5                   10                  15 ttt cca tcc tcc gat gtg ccg gtg aaa gac aag acg aag aag ata act      96
Phe Pro Ser Ser Asp Val Pro Val Lys Asp Lys Thr Lys Lys Ile Thr
            20                  25                  30 tgg gtt agg gta tgg aac tcg acc gat atc ttc cac ata att ctc gta     144
Trp Val Arg Val Trp Asn Ser Thr Asp Ile Phe His Ile Ile Leu Val
        35                  40                  45 ggc ggt ctg cat gtt ttg tgc ttg tct gca cct ttc acc ttc agt tgg     192
Gly Gly Leu His Val Leu Cys Leu Ser Ala Pro Phe Thr Phe Ser Trp
    50                  55                  60 agt gca ttt tgg ttg tcc tta acg cta tac gcc gtc tgt gga gtc ttc     240
Ser Ala Phe Trp Leu Ser Leu Thr Leu Tyr Ala Val Cys Gly Val Phe
65                  70                  75                  80 ggg act act ctg tca tac cac agg aac ctt act cat aga agt ttc aag     288
Gly Thr Thr Leu Ser Tyr His Arg Asn Leu Thr His Arg Ser Phe Lys
                85                  90                  95 ctt cca aag tat ctc gag tac ttc ttc gcc tat gtt gga ctt cat gct     336
Leu Pro Lys Tyr Leu Glu Tyr Phe Phe Ala Tyr Val Gly Leu His Ala
            100                 105                 110 tta cag ggg gat cct gta tgg tgg gtg agc aca cac agg tac cat cac     384
Leu Gln Gly Asp Pro Val Trp Trp Val Ser Thr His Arg Tyr His His
        115                 120                 125 aag ttc acc gac aca tac ctg gat cca cac agt cca att gaa gga ttt     432
Lys Phe Thr Asp Thr Tyr Leu Asp Pro His Ser Pro Ile Glu Gly Phe
    130                 135                 140 tgg ttc tct cac ata ttc tgg ctg ttc gac tct aaa tat ata ctc gaa     480
Trp Phe Ser His Ile Phe Trp Leu Phe Asp Ser Lys Tyr Ile Leu Glu
145                 150                 155                 160 gag tgc gga cgg tac gaa aat gcc ggc gat cta ctg aaa caa agc tat     528
Glu Cys Gly Arg Tyr Glu Asn Ala Gly Asp Leu Leu Lys Gln Ser Tyr
                165                 170                 175 tac agg ttt cta gaa agg act ttt gtg ttt cac gtt tac cta caa gca     576
Tyr Arg Phe Leu Glu Arg Thr Phe Val Phe His Val Tyr Leu Gln Ala
            180                 185                 190 gct ttg ctg tat atg ttc gga gga ttt cct ttc atc gtc tgg gga atg     624
Ala Leu Leu Tyr Met Phe Gly Gly Phe Pro Phe Ile Val Trp Gly Met
        195                 200                 205 gca gta aga act gta tgg gga ttc cat gcc tct tgg cta gtg aat tca     672
Ala Val Arg Thr Val Trp Gly Phe His Ala Ser Trp Leu Val Asn Ser
    210                 215                 220 gta tgc cac aga tat gga cac caa gca tgg gac aca ggg gac ttg tca     720
Val Cys His Arg Tyr Gly His Gln Ala Trp Asp Thr Gly Asp Leu Ser
225                 230                 235                 240 aca aac aac tgg ttc ata gcg atg ctt aca tcg ggt gag ggc tgg cat     768
Thr Asn Asn Trp Phe Ile Ala Met Leu Thr Ser Gly Glu Gly Trp His
                245                 250                 255 aac aac cat cac gct ttt gag tat tca gct cgg cat gga ata gag tgg     816
Asn Asn His His Ala Phe Glu Tyr Ser Ala Arg His Gly Ile Glu Trp
            260                 265                 270 tgg caa ata gat acg aca tgg tat gta ata aag cta ctc gaa tat ctc     864
Trp Gln Ile Asp Thr Thr Trp Tyr Val Ile Lys Leu Leu Glu Tyr Leu
        275                 280                 285 gga ttg gca acg gat gtg aag gtg cct tca gag gtt cac aag cga aag     912
Gly Leu Ala Thr Asp Val Lys Val Pro Ser Glu Val His Lys Arg Lys
```

```
                    290                     295                     300
atg tct ttc aaa aat tgc gtt cag gat aaa cag ttc tgt gtg aac gac        960
Met Ser Phe Lys Asn Cys Val Gln Asp Lys Gln Phe Cys Val Asn Asp
305                     310                     315                     320 aag taa                                                                 966
Lys

<210> SEQ ID NO 4
<211> LENGTH: 321
<212> TYPE: PRT
<213> ORGANISM: Anemone leveillei

<400> SEQUENCE: 4

Met Glu Leu Pro Ala Met Ala Leu Gln Ser Glu Leu Lys Gln Asp Lys
1               5                   10                  15

Phe Pro Ser Ser Asp Val Pro Val Lys Asp Lys Thr Lys Lys Ile Thr
            20                  25                  30

Trp Val Arg Val Trp Asn Ser Thr Asp Ile Phe His Ile Ile Leu Val
        35                  40                  45

Gly Gly Leu His Val Leu Cys Leu Ser Ala Pro Phe Thr Phe Ser Trp
    50                  55                  60

Ser Ala Phe Trp Leu Ser Leu Thr Leu Tyr Ala Val Cys Gly Val Phe
65                  70                  75                  80

Gly Thr Thr Leu Ser Tyr His Arg Asn Leu Thr His Arg Ser Phe Lys
                85                  90                  95

Leu Pro Lys Tyr Leu Glu Tyr Phe Phe Ala Tyr Val Gly Leu His Ala
            100                 105                 110

Leu Gln Gly Asp Pro Val Trp Trp Val Ser Thr His Arg Tyr His His
        115                 120                 125

Lys Phe Thr Asp Thr Tyr Leu Asp Pro His Ser Pro Ile Glu Gly Phe
130                 135                 140

Trp Phe Ser His Ile Phe Trp Leu Phe Asp Ser Lys Tyr Ile Leu Glu
145                 150                 155                 160

Glu Cys Gly Arg Tyr Glu Asn Ala Gly Asp Leu Leu Lys Gln Ser Tyr
                165                 170                 175

Tyr Arg Phe Leu Glu Arg Thr Phe Val Phe His Val Tyr Leu Gln Ala
            180                 185                 190

Ala Leu Leu Tyr Met Phe Gly Gly Phe Pro Phe Ile Val Trp Gly Met
        195                 200                 205

Ala Val Arg Thr Val Trp Gly Phe His Ala Ser Trp Leu Val Asn Ser
    210                 215                 220

Val Cys His Arg Tyr Gly His Gln Ala Trp Asp Thr Gly Asp Leu Ser
225                 230                 235                 240

Thr Asn Asn Trp Phe Ile Ala Met Leu Thr Ser Gly Glu Gly Trp His
                245                 250                 255

Asn Asn His His Ala Phe Glu Tyr Ser Ala Arg His Gly Ile Glu Trp
            260                 265                 270

Trp Gln Ile Asp Thr Thr Trp Tyr Val Ile Lys Leu Leu Glu Tyr Leu
        275                 280                 285

Gly Leu Ala Thr Asp Val Lys Val Pro Ser Glu Val His Lys Arg Lys
    290                 295                 300

Met Ser Phe Lys Asn Cys Val Gln Asp Lys Gln Phe Cys Val Asn Asp
305                 310                 315                 320

Lys
```

<210> SEQ ID NO 5
<211> LENGTH: 939
<212> TYPE: DNA
<213> ORGANISM: Anemone leveillei
<220> FEATURE:
<221> NAME/KEY: CDS
<222> LOCATION: (1)..(939)

<400> SEQUENCE: 5

| | | | | | | | | | | | | | | | | |
|---|---|---|---|---|---|---|---|---|---|---|---|---|---|---|---|---|
| atg | gat | ctc | aca | tca | atg | gca | atg | caa | gaa | aca | acc | gct | gct | gca | gag | 48 |
| Met | Asp | Leu | Thr | Ser | Met | Ala | Met | Gln | Glu | Thr | Thr | Ala | Ala | Ala | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gaa | gac | aga | ctt | cca | tgc | tca | gaa | gtt | cca | gtg | aag | gag | aag | aca | aag | 96 |
| Glu | Asp | Arg | Leu | Pro | Cys | Ser | Glu | Val | Pro | Val | Lys | Glu | Lys | Thr | Lys | |
| | | 20 | | | | | 25 | | | | | 30 | | | | |

| | | | | | | | | | | | | | | | | |
|---|---|---|---|---|---|---|---|---|---|---|---|---|---|---|---|---|
| aag | atc | act | tgg | gtt | agg | aaa | tgg | aac | tcc | acc | gac | gtc | ttc | cac | att | 144 |
| Lys | Ile | Thr | Trp | Val | Arg | Lys | Trp | Asn | Ser | Thr | Asp | Val | Phe | His | Ile | |
| | | 35 | | | | | 40 | | | | | 45 | | | | |

| | | | | | | | | | | | | | | | | |
|---|---|---|---|---|---|---|---|---|---|---|---|---|---|---|---|---|
| ctg | ttt | att | ggt | ggt | ttg | cac | gtt | ttg | tgc | ttg | ttt | gca | cct | tcc | acc | 192 |
| Leu | Phe | Ile | Gly | Gly | Leu | His | Val | Leu | Cys | Leu | Phe | Ala | Pro | Ser | Thr | |
| | 50 | | | | | 55 | | | | | 60 | | | | | |

| | | | | | | | | | | | | | | | | |
|---|---|---|---|---|---|---|---|---|---|---|---|---|---|---|---|---|
| ttc | agc | tgg | aaa | tct | ttt | tgg | gtg | tgc | ttc | gcg | cta | tat | gcc | atc | tgt | 240 |
| Phe | Ser | Trp | Lys | Ser | Phe | Trp | Val | Cys | Phe | Ala | Leu | Tyr | Ala | Ile | Cys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gga | gtg | ttc | ggg | act | act | ttg | tcc | ttc | cac | agg | aac | ctt | aca | cac | aga | 288 |
| Gly | Val | Phe | Gly | Thr | Thr | Leu | Ser | Phe | His | Arg | Asn | Leu | Thr | His | Arg | |
| | | | | 85 | | | | | 90 | | | | | 95 | | |

| | | | | | | | | | | | | | | | | |
|---|---|---|---|---|---|---|---|---|---|---|---|---|---|---|---|---|
| agt | ttc | aag | ctt | cca | aag | tat | ctc | gag | tac | ttc | ttc | gct | tat | gtc | gga | 336 |
| Ser | Phe | Lys | Leu | Pro | Lys | Tyr | Leu | Glu | Tyr | Phe | Phe | Ala | Tyr | Val | Gly | |
| | | | 100 | | | | | 105 | | | | | 110 | | | |

| | | | | | | | | | | | | | | | | |
|---|---|---|---|---|---|---|---|---|---|---|---|---|---|---|---|---|
| ctt | cat | gct | cta | cag | ggt | gat | cca | gtg | tgg | tgg | gtg | agc | aca | cat | aga | 384 |
| Leu | His | Ala | Leu | Gln | Gly | Asp | Pro | Val | Trp | Trp | Val | Ser | Thr | His | Arg | |
| | | 115 | | | | | 120 | | | | | 125 | | | | |

| | | | | | | | | | | | | | | | | |
|---|---|---|---|---|---|---|---|---|---|---|---|---|---|---|---|---|
| tac | cat | cac | aag | tac | act | gac | aca | tac | ctg | gat | cca | cac | agt | cca | atc | 432 |
| Tyr | His | His | Lys | Tyr | Thr | Asp | Thr | Tyr | Leu | Asp | Pro | His | Ser | Pro | Ile | |
| | 130 | | | | | 135 | | | | | 140 | | | | | |

| | | | | | | | | | | | | | | | | |
|---|---|---|---|---|---|---|---|---|---|---|---|---|---|---|---|---|
| gaa | gga | ttt | tgg | ttc | tgc | cac | ata | ttc | tgg | ctt | ttc | gac | tcc | aaa | tat | 480 |
| Glu | Gly | Phe | Trp | Phe | Cys | His | Ile | Phe | Trp | Leu | Phe | Asp | Ser | Lys | Tyr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ata | atc | gaa | aag | tgc | gga | agg | tat | gaa | aat | gca | ggg | gat | ctt | atg | aaa | 528 |
| Ile | Ile | Glu | Lys | Cys | Gly | Arg | Tyr | Glu | Asn | Ala | Gly | Asp | Leu | Met | Lys | |
| | | | | 165 | | | | | 170 | | | | | 175 | | |

| | | | | | | | | | | | | | | | | |
|---|---|---|---|---|---|---|---|---|---|---|---|---|---|---|---|---|
| cag | agc | tat | tac | agg | ttt | ctg | gag | agg | act | ttc | gtg | tat | cat | gtt | tac | 576 |
| Gln | Ser | Tyr | Tyr | Arg | Phe | Leu | Glu | Arg | Thr | Phe | Val | Tyr | His | Val | Tyr | |
| | | | 180 | | | | | 185 | | | | | 190 | | | |

| | | | | | | | | | | | | | | | | |
|---|---|---|---|---|---|---|---|---|---|---|---|---|---|---|---|---|
| tta | caa | gca | gct | ttg | ttg | tat | ctg | ttc | gga | ggg | ttt | ccg | ttc | atc | gtt | 624 |
| Leu | Gln | Ala | Ala | Leu | Leu | Tyr | Leu | Phe | Gly | Gly | Phe | Pro | Phe | Ile | Val | |
| | | 195 | | | | | 200 | | | | | 205 | | | | |

| | | | | | | | | | | | | | | | | |
|---|---|---|---|---|---|---|---|---|---|---|---|---|---|---|---|---|
| tgg | gga | atg | gca | gta | aga | act | ata | ttg | gga | ttc | cat | ctc | tct | tgg | cta | 672 |
| Trp | Gly | Met | Ala | Val | Arg | Thr | Ile | Leu | Gly | Phe | His | Leu | Ser | Trp | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| gtg | aat | tca | gtt | tgc | cat | aga | tgg | gga | aac | cga | cca | tgg | aac | acc | ggg | 720 |
| Val | Asn | Ser | Val | Cys | His | Arg | Trp | Gly | Asn | Arg | Pro | Trp | Asn | Thr | Gly | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gac | ttg | tca | aca | aac | aat | tgg | ttc | att | gct | atg | ctt | aca | tcg | ggt | gag | 768 |
| Asp | Leu | Ser | Thr | Asn | Asn | Trp | Phe | Ile | Ala | Met | Leu | Thr | Ser | Gly | Glu | |
| | | | | 245 | | | | | 250 | | | | | 255 | | |

| | | | | | | | | | | | | | | | | |
|---|---|---|---|---|---|---|---|---|---|---|---|---|---|---|---|---|
| ggt | tgg | cat | aac | aac | cat | cat | gcg | ttt | gag | tat | tca | gct | cgg | cat | gga | 816 |
| Gly | Trp | His | Asn | Asn | His | His | Ala | Phe | Glu | Tyr | Ser | Ala | Arg | His | Gly | |
| | | | 260 | | | | | 265 | | | | | 270 | | | |

| | | | | | | | | | | | | | | | | |
|---|---|---|---|---|---|---|---|---|---|---|---|---|---|---|---|---|
| ata | gag | tgg | tgg | caa | ata | gac | acg | acg | tgg | tac | ata | ata | aag | cta | ctc | 864 |
| Ile | Glu | Trp | Trp | Gln | Ile | Asp | Thr | Thr | Trp | Tyr | Ile | Ile | Lys | Leu | Leu | |
| | | 275 | | | | 280 | | | | | 285 | | | | | |
| gag | tat | ctc | gga | ttg | gca | act | gat | atc | aag | gtg | ccc | tca | gaa | att | cac | 912 |
| Glu | Tyr | Leu | Gly | Leu | Ala | Thr | Asp | Ile | Lys | Val | Pro | Ser | Glu | Ile | His | |
| | 290 | | | | | 295 | | | | | 300 | | | | | |
| aag | cgt | aag | atg | tct | ttc | aaa | aat | tga | | | | | | | | 939 |
| Lys | Arg | Lys | Met | Ser | Phe | Lys | Asn | | | | | | | | | |
| 305 | | | | | 310 | | | | | | | | | | | |

<210> SEQ ID NO 6
<211> LENGTH: 312
<212> TYPE: PRT
<213> ORGANISM: Anemone leveillei

<400> SEQUENCE: 6

Met Asp Leu Thr Ser Met Ala Met Gln Glu Thr Thr Ala Ala Ala Glu
1               5                   10                  15

Glu Asp Arg Leu Pro Cys Ser Glu Val Pro Val Lys Glu Lys Thr Lys
            20                  25                  30

Lys Ile Thr Trp Val Arg Lys Trp Asn Ser Thr Asp Val Phe His Ile
        35                  40                  45

Leu Phe Ile Gly Gly Leu His Val Leu Cys Leu Phe Ala Pro Ser Thr
    50                  55                  60

Phe Ser Trp Lys Ser Phe Trp Val Cys Phe Ala Leu Tyr Ala Ile Cys
65                  70                  75                  80

Gly Val Phe Gly Thr Thr Leu Ser Phe His Arg Asn Leu Thr His Arg
                85                  90                  95

Ser Phe Lys Leu Pro Lys Tyr Leu Glu Tyr Phe Phe Ala Tyr Val Gly
            100                 105                 110

Leu His Ala Leu Gln Gly Asp Pro Val Trp Val Ser Thr His Arg
        115                 120                 125

Tyr His His Lys Tyr Thr Asp Thr Tyr Leu Asp Pro His Ser Pro Ile
    130                 135                 140

Glu Gly Phe Trp Phe Cys His Ile Phe Trp Leu Phe Asp Ser Lys Tyr
145                 150                 155                 160

Ile Ile Glu Lys Cys Gly Arg Tyr Glu Asn Ala Gly Asp Leu Met Lys
                165                 170                 175

Gln Ser Tyr Tyr Arg Phe Leu Glu Arg Thr Phe Val Tyr His Val Tyr
            180                 185                 190

Leu Gln Ala Ala Leu Leu Tyr Leu Phe Gly Gly Phe Pro Phe Ile Val
        195                 200                 205

Trp Gly Met Ala Val Arg Thr Ile Leu Gly Phe His Leu Ser Trp Leu
    210                 215                 220

Val Asn Ser Val Cys His Arg Trp Gly Asn Arg Pro Trp Asn Thr Gly
225                 230                 235                 240

Asp Leu Ser Thr Asn Asn Trp Phe Ile Ala Met Leu Thr Ser Gly Glu
                245                 250                 255

Gly Trp His Asn Asn His His Ala Phe Glu Tyr Ser Ala Arg His Gly
            260                 265                 270

Ile Glu Trp Trp Gln Ile Asp Thr Thr Trp Tyr Ile Ile Lys Leu Leu
        275                 280                 285

Glu Tyr Leu Gly Leu Ala Thr Asp Ile Lys Val Pro Ser Glu Ile His
    290                 295                 300

Lys Arg Lys Met Ser Phe Lys Asn
305                 310

<210> SEQ ID NO 7
<211> LENGTH: 24
<212> TYPE: DNA
<213> ORGANISM: Artificial Sequence
<220> FEATURE:
<223> OTHER INFORMATION: Forward primer designed to encode conserved
      amino acid sequence corresponding to histidine box II in
      previously characterized acyl-CoA desaturases
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (18)..(18)
<223> OTHER INFORMATION: n is inosine

<400> SEQUENCE: 7
tgggtnwsna yncaymgnta ycay                                          24

<210> SEQ ID NO 8
<211> LENGTH: 29
<212> TYPE: DNA
<213> ORGANISM: Artificial Sequence
<220> FEATURE:
<223> OTHER INFORMATION: Reverse primer designed to encode the
      complement of histidine box III in previously characterized
      acyl-CoA desaturases
<220> FEATURE:
<221> NAME/KEY: misc_feature
<222> LOCATION: (21)..(21)
<223> OTHER INFORMATION: n is inosine
<220> FEATURE:
<221> NAME/KEY: misc_feature
<222> LOCATION: (27)..(27)
<223> OTHER INFORMATION: n is inosine

<400> SEQUENCE: 8
gcrtgrtgrt trttrtgcca nccytcncc                                     29

<210> SEQ ID NO 9
<211> LENGTH: 34
<212> TYPE: DNA
<213> ORGANISM: Caltha palustris

<400> SEQUENCE: 9
ggtcgacatg gctctaattg caacaacccc caaa                               34

<210> SEQ ID NO 10
<211> LENGTH: 34
<212> TYPE: DNA
<213> ORGANISM: Caltha palustris

<400> SEQUENCE: 10
gatcgatatg gctctaattg caacaacccc caaa                               34

<210> SEQ ID NO 11
<211> LENGTH: 26
<212> TYPE: DNA
<213> ORGANISM: Caltha palustris -continued

```
<400> SEQUENCE: 11
gagctcttac tcgctgaaac acatcc                                          26

<210> SEQ ID NO 12
<211> LENGTH: 27
<212> TYPE: DNA
<213> ORGANISM: Caltha palustris

<400> SEQUENCE: 12
gatcgattta ctcgctgaaa cacatcc                                         27

<210> SEQ ID NO 13
<211> LENGTH: 27
<212> TYPE: DNA
<213> ORGANISM: Anemone leveillei

<400> SEQUENCE: 13
ggtctagaat ggatctcaca tcaatgg                                         27

<210> SEQ ID NO 14
<211> LENGTH: 28
<212> TYPE: DNA
<213> ORGANISM: Anemone leveillei

<400> SEQUENCE: 14
ggcggccgca tggatctcac atcaatgg                                        28

<210> SEQ ID NO 15
<211> LENGTH: 26
<212> TYPE: DNA
<213> ORGANISM: Anemone leveillei

<400> SEQUENCE: 15
gatcgatatg gatctcacat caatgg                                          26

<210> SEQ ID NO 16
<211> LENGTH: 35
<212> TYPE: DNA
<213> ORGANISM: Anemone leveillei

<400> SEQUENCE: 16
ggtcgactca attttgaaa gacatcttac gcttg                                 35

<210> SEQ ID NO 17
<211> LENGTH: 37
<212> TYPE: DNA
<213> ORGANISM: Anemone leveillei

<400> SEQUENCE: 17
ggcggccgct caattttga aagacatctt acgcttg                               37

<210> SEQ ID NO 18
<211> LENGTH: 25
<212> TYPE: DNA
<213> ORGANISM: Anemone leveillei

<400> SEQUENCE: 18
ggcccgggat ggaactccca gcgat                                           25

<210> SEQ ID NO 19
<211> LENGTH: 24
<212> TYPE: DNA
<213> ORGANISM: Anemone leveillei
```

<400> SEQUENCE: 19
ggcggccgca gttcaccgac atac                                          24

<210> SEQ ID NO 20
<211> LENGTH: 24
<212> TYPE: DNA
<213> ORGANISM: Anemone leveillei

<400> SEQUENCE: 20
gatcgatatg gaactcccag cgat                                          24

<210> SEQ ID NO 21
<211> LENGTH: 29
<212> TYPE: DNA
<213> ORGANISM: Anemone leveillei

<400> SEQUENCE: 21
ggtcgactta cttgtcgttc acacagaac                                     29

<210> SEQ ID NO 22
<211> LENGTH: 31
<212> TYPE: DNA
<213> ORGANISM: Anemone leveillei

<400> SEQUENCE: 22
ggcggccgct tacttgtcgt tcacacagaa c                                  31

<210> SEQ ID NO 23
<211> LENGTH: 29
<212> TYPE: DNA
<213> ORGANISM: Anemone leveillei

<400> SEQUENCE: 23
gatcgattta cttgtcgttc acacagaac                                     29

<210> SEQ ID NO 24
<211> LENGTH: 891
<212> TYPE: DNA
<213> ORGANISM: A. castellanii elongase

<400> SEQUENCE: 24

```
atggcggctg cgacggcgac gacggcaacg acggcggtga tggagcaagt gcccattacg    60
gaggccatct tccggccgga cctctgggtc ggacgggacc agtgggaggc gaatgccgtg   120
agcttcgtat ggaggtactg gtggttcttc ctggtgatgg gcgtggcata cctgcccatc   180
atcttcggcc tcaagtactg gatgaaggat cgtccggcct tcaacctccg tcggccgctc   240
atcttgtgga atatcttcat ggcgacgttc tcgaccgccg gcttcctgtc gatcgtctac   300
cccctcatcg agaactgggt ctaccccggc ggcggcctca ccccgcatga gttcatctgc   360
tcggccagct actcctacaa gtttggtgat gcgccatct gggtgttcct cttcaacatg   420
tcgaagatcc tcgagttcgt cgacaccatc ttcatcgtcc caggaagac ccacctcggc   480
ttcctccact actaccacca catcatcacc tactccttct gcctctacgc cggccagtac   540
atgcaccact acaactgtgg cggctatttc ttctgcctca tgaacttctt cgtccacggc   600
atcatgtact tctactacgc ctctccgctc catgggcttc gtccctcctt cgatattggc   660
atcaccttcc tccagatttt gcaaatggtg ctcggcgtgg ccatcatcac catctccgcc   720
ggctgcgaga aggtggaccc catcggaacg accttcggct actttattta tttctcgttc   780
```

```
-continued
ttcgtcctct tctgcaagtt cttctactac cgctacatcg ccacgccgc caagaagccc        840 gaggccgccg ccaagtcgcc agccaccaag cccaagagga agcacgacta a                891

<210> SEQ ID NO 25
<211> LENGTH: 777
<212> TYPE: DNA
<213> ORGANISM: Isochrysis galbana

<400> SEQUENCE: 25
atggccctcg caaacgacgc gggagagcgc atctgggcgg ctgtgaccga cccggaaatc        60
ctcattggca ccttctcgta cttgctactc aaaccgctgc tccgcaattc cgggctggtg       120
gatgagaaga agggcgcata caggacgtcc atgatctggt acaacgttct gctggcgctc       180
ttctctgcgc tgagcttcta cgtgacggcg accgccctcg gctgggacta tggtacgggc       240
gcgtggctgc gcaggcaaac cggcgacaca ccgcagccgc tcttccagtg cccgtccccg       300
gtttgggact cgaagctctt cacatggacc gccaaggcat tctattactc caagtacgtg       360
gagtacctcg acacggcctg gctgagggtc tcctttctcc aggccttcca ccactttggc       420
gcgccgtggg atgtgtacct cggcattcgg ctgcacaacg agggcgtatg gatcttcatg       480
tttttcaact cgttcattca caccatcatg tacacctact acggcctcac cgccgccggg       540
tataagttca aggccaagcc gctcatcacc gcgatgcaga tctgccagtt cgtgggcggc       600
ttcctgttgg tctgggacta catcaacgtc ccctgcttca actcggacaa agggaagttg       660
ttcagctggg ctttcaacta tgcatacgtc ggctcggtct tcttgctctt ctgccacttt       720
ttctaccagg acaacttggc aacgaagaaa tcggccaagg cgggcaagca gctctag         777
```

PROCESS FOR THE PRODUCTION OF Δ5-UNSATURATED FATTY ACIDS IN TRANSGENIC ORGANISMS

RELATED APPLICATIONS

This application claims benefit of United Kingdom application GB 0523915.7 filed Nov. 24, 2005, United Kingdom application GB 0524420.7 filed Nov. 30, 2005, and United Kingdom application GB 0612109.9 filed Jun. 19, 2006.

DESCRIPTION

The present invention relates to a process for the production of Δ5-unsaturated fatty acids in an organism by introducing, into the organism, nucleic acids which encode polypeptides with Δ5-desaturase activity. These nucleic acid sequences, if appropriate together with further nucleic acid sequences which encode polypeptides of the biosynthesis of the fatty acid or lipid metabolism, can advantageously be expressed in the organism. The process can be used for the production of non-methylene-interrupted fatty acids (NMIFAs) such as sciadonic acid (Δ5cis-11, 14-20:3) and juniperonic acid (Δ5cis-11, 14, 17-20:4), which do not occur naturally in most food plants. The invention furthermore relates to a process for the production of oils and/or triacylglycerides with an elevated content of long-chain polyunsaturated fatty acids.

The invention furthermore relates to the nucleic acid sequences, gene constructs, vectors and organisms comprising the nucleic acid sequences according to the invention, vectors comprising the nucleic acid sequences and/or the gene constructs and to transgenic organisms comprising the abovementioned nucleic acid sequences, gene constructs and/or vectors.

A further part of the invention relates to oils, lipids and/or fatty acids produced by the process according to the invention and to their use. Moreover, the invention relates to Δ5-unsaturated fatty acids and to triglycerides with an elevated content of Δ5-unsaturated fatty acids and to their use.

Non-methylene-interrupted fatty acids (NMIFAs) have been found in algae, slime molds, marine sponges and plants. Seed plants are botanically divided into gymnosperms and angiosperms. It is believed that the angiosperms have evolved from their gymnospermous predecessors in the late Jurassic or early Cretaceous. The seed oils of nearly all gymnosperms contain Δ5-NMIFAs, usually in the form of C16-20 monounsaturates (see, for example, Wolff et al, Lipids 1999, October; 34(10); 1083-1097). Similar Δ5-NMIFAs occur in the seed oils of a very few angiosperm species, predominantly in the plant family Ranunculaceae but also found in some other "primitive" plant families, such as Menispermaceae and Limnanthacea. In angiosperms, the unusual NMIFAs are invariably found only in the seed oils and do not occur in vegetative tissue; this is in contrast to the gymnosperms, where the presence of these fatty acids in leaves is well-documented.

Recent studies have shown biomedical benefits of Δ5cis-NMIFA-containing oils, such as triglyceride-lowering effect and anti-inflammatory properties (Asset et al, 1999, Lipids, 34, 39-44; Berger et al, Lipids in Health and Disease 2002, 1:5, and references therein). Oils containing Δ5cis-11, 14-20:3 sciadonic acid (SA) can also lower plasma cholesterol in experimental animals. Several investigators have shown that the addition of sciadonic acid to animals or cultured cells is effective in reducing the level of 20:4n-6 (arachidonic acid, ARA) in phosphatidylinositol (PI), thereby modifying cellular ARA metabolism (Tanaka et al, 1999, Biochem. Biophys. Res. Comm., 264, 683-688; and Tanaka et al, 2001, Eur. J. Biochem., 268, 4928-4939).

It would therefore be advantageous to be able to produce Δ5cis-NMIFAs such as sciadonic acid and juniperonic acid in other organisms from where they can easily be extracted. One example of this is the production of the fatty acids in the vegetative tissues of angiospermous plants.

It is known that polyunsaturated fatty acids such as arachidonic acid, eicosapentaenoic acid (EPA) and docosahexaenoic acid (DHA) can be produced in a variety of ways. Thus, EPA or DHA are produced in marine bacteria such as Vibrio sp. or Shewanella sp. via the polyketide pathway (Yu, R. et al. Lipids 35:1061-1064, 2000; Takeyama, H. et al. Microbiology 143:2725-2731, 1997).

An alternative strategy is the alternating activity of desaturases and elongases (Zank, T. K. et al. Plant Journal 31:255-268, 2002; Sakuradani, E. et al. Gene 238:445-453, 1999). A modification of the above-described pathway by Δ6-desaturase, Δ6-elongase, Δ5-desaturase, Δ5-elongase and Δ4-desaturase is the Sprecher pathway (Sprecher 2000, Biochim. Biophys. Acta 1486:219-231) in mammals. Instead of the Δ4-desaturation, a further elongation step is effected here to give $C_{24}$, followed by a further Δ6-desaturation and finally β-oxidation to give the $C_{22}$ chain length. Thus what is known as Sprecher pathway (see FIG. 1) is, however, not suitable for the production in plants and microorganisms since the regulatory mechanisms are not known.

Our co-pending UK patent application No. 0523915.7 as well as UK patent application No. 0524420.7 teach the production of polyunsaturated fatty acids in a variety of plants and microorganism by means of genetically modifying these species with a selection of nucleic acid sequences encoding a series of elongase and desaturase enzymes.

The present inventors have decided to adopt a similar strategy in order to produce Δ5-NMIFAs. In order to do this, it was necessary to identify a desaturase capable of introducing a C═C double bond at the Δ5-position.

The biosynthesis of higher plant monounsaturated very long chain fatty acids (VLCFAs) containing a Δ5 double bond was studied previously by radio labeling of developing Limnanthes alba seeds. The seed oil of Limnanthes spp is enriched in the Δ5-eicosaenoic acid (20:1 Δ5). Based on in vitro analysis of Limnanthes spp. seed extracts, Moreau et al, Arch Biochem Biophys. 1981; 209:376-384 suggested that 20:0-CoA is the substrate for the Δ5-desaturase. In more recent studies, random sequencing of EST library from L. douglasii seeds resulted in the identification of a candidate cDNA for a Δ5-desaturase that showed similarity to known acyl-CoA desaturases from animals, yeast and cyanobactaria (Cahoon et al, 2000, Plant Physiology, 124, 243-251). Co-expression of this desaturase cDNA with an FAE1 (fatty acid elongating activity) homolog from L. douglasii in soybean somatic embryos resulted in the accumulation of Δ5-monounsaturated 16:1, 18:1 and 20:1 fatty acids, thus confirming the pathway proposed for 20:1 Δ5 formation in Limnanthes spp:

a) a large flux of palmitic acid (16:0) from the plastid to the endoplasmic reticulum;

b) microsomal elongation of 16:0, presumably as a CoA ester, to eicosanoic acid (20:0), c) Δ5-desaturation of 20:0 to form 20:1 Δ5 (see Cahoon et al, Plant Physiol. 2000 September; 124(1):243-51 and references therein).

However, no direct biochemical evidence has been presented to support the assertion that the Limnanthes desaturases utilises acyl-CoA substrates, as opposed to the predominant glycerolipid or ACP-linked desaturation occurring in plants.

Equally, cDNAs encoding proteins related to the animal and yeast acyl-CoA desaturases (abbreviated to ADS) have been identified in several plant species, though their activity towards acyl-CoA substrates is inferred only from homology (Fukuchi-Mizutani et al, 1998, Plant and Cell Physiology 39: 247-253).

Two cytoplasmic ADS enzymes from *Arabidopsis*, ADS1 and ADS2, formed Δ9-desaturated fatty acids when expressed in yeast (Heilmann et al. 2004, PNAS, 101(28), 10266-10271), *Arabidopsis* or in *Brassica juncea* (ADS1 only, Yao et al, 2003 Plant Biotechnol 1: 221-229). ADS3, another member of the *Arabidopsis* desaturase (ADS) multigene family, was characterized as a gene, encoding palmitoyl-monogalactosyldiacylglycerol Δ7-desaturase. A conifera white spruce (*Picea glauca*) homolog of ADS3 has been characterized as an 18:0 Δ9 desaturase gene by heterologous expression in yeast (Marillia et al., 2002, FEBS Lett, 526: 49-52). Δ5cis-C20 NMIFAs occur in seed and leaves in all Coniferae (see, for example, Destaillats et al, Lipids, 2001 November; 36(11); 1247-1254 and Wolff et al, Lipids. 2001 May; 36(5); 439-451). It was also found that seed oil of several members of the rather primitive angiosperm family Ranunculaceae contains significant amounts of these unusual fatty acids (see Wolff et al. 2002 for review: Lipids. 2002 January; 37(1):17-26 and see also Tsevegsuren et al, (1997) Hrc-Journal of High Resolution Chromatography, 20: 237-241).

*Cimicifuga* spp., *Caltha palustris* L. and *Anemone leveillei/rivularis* are all reported to produce cis Δ5 desaturated fatty acids, including 16:1 Δ5 and 18:1 Δ5 and (predominantly) 20:3Δ5,11,14 (sciadonic acid). *C. palustris* produces additional Δ5 desaturation products such as 18:4 Δ5,9,12,15 and 20:4 Δ5,11,14,17 Ouniperonic acid). In *Caltha*, *Cimicifuga* and *A. leveillei* the main Δ5cis-C20 NMIFA is sciadonic acid (SA, 20:3, Δ5,11,14). It is found at levels of 19.7% of total fatty acids in seed oils of *C. palustris* and of 9.8% of total fatty acids in *Anemone* seed oils. *C. palustris* produces additional Δ5 desaturation products such as 18:4Δ5,9,12,15, 20:1Δ5 and 20:4Δ5,11,14,17 (Smith et al, 1968, Lipids 3: 37-&). We have previously attempted to identify the Δ5-desaturase responsible for the synthesis of SA from *Anemone*, and initially considered it likely that this enzyme was a cytochrome b5 fusion desaturase. Although *Anemone* contains several such desaturases, none of them were identified as being involved in SA synthesis (Whitney et al. 2003, Planta, 217(6), 983-992)

The present inventors therefore hypothesized that the enzyme introducing a double bond at the Δ5 position to yield SA might be an acyl-CoA desaturase similar to the group of membrane bound fatty acid desaturases recently cloned from *Arabidopsis*, rose and *Limnanthes* and following this reasoning, have obtained nucleotide sequences which encode a Δ5-desaturase enzyme. This has made possible the development of a process for the production of Δ5-unsaturated NMIFAs in a variety of organisms.

Therefore, in a first aspect of the present invention, there is provided a process for the production of a compound of formula (I):

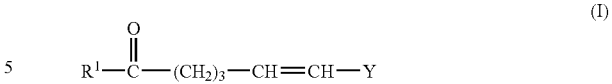

in an organism, the process comprising introducing into an organism which comprises a lipid of general formula (III):

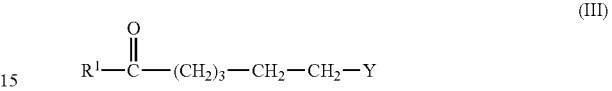

at least one nucleic acid sequence comprising:
a) SEQ ID NO: 1, SEQ ID NO: 3 or SEQ ID NO: 5;
b) a nucleic acid sequence which hybridizes under stringent conditions with a nucleic acid sequence of SEQ ID NO: 1, SEQ ID NO: 3 or SEQ ID NO: 5.
c) a nucleic acid sequence which encodes a polypeptide of SEQ ID NO: 2, SEQ ID NO: 4 or SEQ ID NO: 6;
d) a derivative of a nucleic acid sequence of SEQ ID NO: 1, SEQ ID NO: 3 or SEQ ID NO: 5 which encodes a polypeptide with at least 40% identity at the amino acid level with SEQ ID NO: 2, SEQ ID NO: 4 or SEQ ID NO: 6, wherein said polypeptide has Δ5-desaturase activity;

and expressing said nucleic acid sequence;

wherein, in general formulae I and III:
Y=a $C_{10}$-$C_{18}$ hydrocarbon chain containing up to four carbon-carbon double bonds;
$R^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

in which
$R^2$=hydrogen, lysophosphatidyl choline, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl,
$R^3$=hydrogen, saturated or unsaturated $C_2$-$C_{24}$-alkylcarbonyl, or $R^2$ and $R^3$ independently of one another are a radical of the formula Ia:

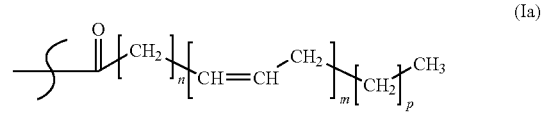

in which n=2, 3, 4, 5, 6, 7 or 9, m=2, 3, 4, 5 or 6 and p=0 or 3;

and wherein an oxygen in the $R^1$ radical may be replaced by sulphur such that $R^1$ is bonded to the remainder of the molecule via a thioester linkage.

In the context of the present invention "hybridizes under stringent conditions" is intended to describe hybridization and washing conditions under which nucleotide sequences with at least 60% homology to one another usually remain hybridized with one another. Conditions are preferably such that sequences with at least approximately 65%, preferably at least approximately 70% and especially preferably at least 75% or more homology to one another usually remain hybridized to one another. These stringent conditions are known to the skilled worker and described, for example, in Current Protocols in Molecular Biology, John Wiley & Sons, N.Y. (1989), 6.3.1-6.3.6. A preferred nonlimiting example of stringent hybridization conditions is hybridizations in 6× sodium chloride/sodium citrate (=SSC) at approximately 45° C., followed by one or more washing steps in 0.2×SSC, 0.1% SDS at 50 to 65° C. The skilled worker knows that these hybridization conditions differ depending on the type of nucleic acid and, for example when organic solvents are present, regarding temperature and buffer concentration. Under "standard hybridization conditions", for example, the hybridization temperature is, depending on the type of nucleic acid, between 42° C. and 58° C. in aqueous buffer with a concentration of 0.1 to 5×SSC (pH 7.2). If organic solvents, for example 50% formamide, are present in the abovementioned buffer, the temperature under standard conditions is approximately 42° C. The hybridization conditions for DNA:DNA hybrids, for example, are 0.1×SSC and 20° C. to 45° C., preferably 30° C. to 45° C. The hybridization conditions for DNA:RNA hybrids are, for example, 0.1×SSC and 30° C. to 55° C., preferably 45° C. to 55° C. The abovementioned hybridization conditions are determined by way of example for a nucleic acid with approximately 100 bp (=base pairs) in length and with a G+C content of 50% in the absence of formamide. The skilled worker knows how to determine the required hybridization conditions on the basis of the abovementioned textbooks or textbooks such as Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

Furthermore, when the present specification refers to isolated nucleic acid molecules of a nucleotide sequence which hybridize with one of the nucleotide sequences shown in SEQ ID NO: 1, SEQ ID NO: 3 or SEQ ID NO: 5 or with a part thereof under stringent conditions, "a part thereof" is understood as meaning, in accordance with the invention, that at least 25 base pairs (=bp), 50 bp, 75 bp, 100 bp, 125 bp or 150 bp, preferably at least 175 bp, 200 bp, 225 bp, 250 bp, 275 bp or 300 bp, especially preferably 350 bp, 400 bp, 450 bp, 500 bp or more base pairs are used for the hybridization.

In the context of the present invention "Homologs" of the Δ5-desaturase nucleic acid sequences with the sequence SEQ ID NO: 1, SEQ ID NO: 3 or SEQ ID NO: 5 means, for example, allelic variants with at least approximately 50 or 60%, preferably at least approximately 60 or 70%, more preferably at least approximately 70 or 80%, 90% or 95% and even more preferably at least approximately 85%, 86%, 87%, 88%, 89%, 90%, 91%, 92%, 93%, 94%, 95%, 96%, 97%, 98%, 99% or more identity or homology with a nucleotide sequence shown in SEQ ID NO: 1, SEQ ID NO: 3 or SEQ ID NO: 5. "Allelic variants" comprise in particular functional variants which can be obtained by deletion, insertion or substitution of nucleotides from/into the sequence, it being intended, however, that the enzyme activity of the resulting proteins which are synthesized is advantageously retained for the insertion of one or more genes. "Homologs" also means bacterial, fungal and plant homologs, truncated sequences, single-stranded DNA or RNA of the coding and noncoding DNA sequence and derivatives such as, for example, promoter variants. The promoters upstream of the nucleotide sequences detailed can be modified by one or more nucleotide exchanges, by insertion(s) and/or deletion(s) without the functionality or activity of the promoters being adversely affected, however. It is furthermore possible that the modification of the promoter sequence enhances their activity or that they are replaced entirely by more active promoters, including those from heterologous organisms.

In order to determine the percentage of homology (=identity) of two amino acid sequences, the sequences are written one under the other for an optimal comparison (for example, gaps may be introduced into the sequence of a protein or of a nucleic acid in order to generate an optimal alignment with the other protein or the other nucleic acid). Then, the amino acid residue or nucleotides at the corresponding amino acid positions or nucleotide positions are compared. If a position in a sequence is occupied by the same amino acid residue or the same nucleotide as the corresponding position in the other sequence, then the molecules are homologous at this position (i.e. amino acid or nucleic acid "homology" as used in the present context corresponds to amino acid or nucleic acid "identity"). The percentage of homology between the two sequences is a function of the number of positions which the sequences share (i.e. % homology= number of identical positions/total number of positions×100). The terms homology and identity are therefore to be considered as synonymous.

The homology was calculated over the entire amino acid or nucleic acid sequence region. The skilled worker has available a series of programs which are based on various algorithms for the comparison of various sequences. Here, the algorithms of Needleman and Wunsch or Smith and Waterman give particularly reliable results. The program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are part of the GCG software packet [Genetics Computer Group, 575 Science Drive, Madison, Wis., USA 53711 (1991)], were used for the sequence alignment. The sequence homology values which are indicated above as a percentage were determined over the entire sequence region using the program GAP and the following settings: Gap Weight: 50, Length Weight: 3, Average Match: 10.000 and Average Mismatch: 0.000. Unless otherwise specified, these settings were always used as standard settings for the sequence alignments.

In the context of the present invention "Δ5-desaturase activity" is understood as meaning that a protein encoded by a derivative of SEQ ID NO: 1, SEQ ID NO: 3 or SEQ ID NO: 5 retains an enzymatic activity of at least 10%, preferably 20%, especially preferably 30% and very especially 40% in comparison with the proteins/enzymes encoded by the sequence SEQ ID NO: 1, SEQ ID NO: 3 or SEQ ID NO: 5 and can thus catalyse the reaction of a compound of formula III to form a compound of formula I.

In the context of the present invention, the term "thioester linkage" refers to a compound in which the —O— of an ester group is replaced by a —S—. Thus, in the case where $R^1$ is lysophosphatidylcholine, the free oxygen of the lysophosphatidyl choline radical may be replaced by sulphur atom such that the linkage to the remainder of the molecule is via a thioester rather than an ester group. The same also applies to other $R^1$ groups.

In the context of the present invention, "saturated or unsaturated $C_2$-$C_{24}$-alkylcarbonyl chain" refers to a substituted or unsubsituted alkylcarbonyl, alkenylcarbonyl or alkynylcarbonyl group having one or more double and/or triple bonds. Suitable substituents include hydroxyl or epoxy.

When $R^2$ or $R^3$ are $C_2$-$C_{24}$-alkylcarbonyl chains, examples of suitable groups include radicals such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl-, n-nonadecylcarbonyl, n-eicosylcarbonyl, n-docosanylcarbonyl- or n-tetracosanylcarbonyl, which comprise one or more double bonds.

Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds are preferred.

Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds.

Even more preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These advantageous radicals can comprise two, three, four, five or six double bonds. The especially preferred radicals with 20 or 22 carbon atoms in the fatty acid chain comprise up to six double bonds, advantageously three, four, five or six double bonds, especially preferably five or six double bonds. All the above-mentioned radicals are derived from the corresponding fatty acids. The substituents $R^2$ or $R^3$ in formula II are advantageously and independently of one another saturated or unsaturated $C_{18}$-$C_{22}$-alkylcarbonyl, especially advantageously they are, independently of one another, unsaturated $C_{18}$-, $C_{20}$- or $C_{22}$-alkylcarbonyl with at least two double bonds.

In the compound of general formula (I), it is preferred that the —CH═CH— double bond is in the cis orientation.

The $C_{10}$-$C_{18}$ hydrocarbon chain which forms the group Y may contain up to 4 carbon-carbon double bonds and these will generally be positioned such that the product of formula I is a non-methylene-interrupted fatty acid.

In the moiety Y, the carbon-carbon double bonds are preferably in the cis orientation. Preferred Y moieties include:

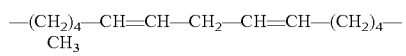

such that the compound of general formula I is sciadonic acid or a derivative thereof; and

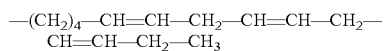

such that the compound of general formula (I) is juniperonic acid or a derivative thereof.

When Y is one of these moieties, the product can be obtained in any organism which naturally produces linoleic (C18:2 n-6) or linolenic (C18:3 n-3) acid by genetically modifying that organism to express a Δ9 elongase enzyme as well as a Δ5-desaturase enzyme. The processes are as follows:

C18:2 n-6 (linoleic acid) is converted by Δ9 elongase to 11,14 C20:2;

11,14 C20:2 is converted by Δ5-desaturase to Δ5cis-11,14-20:3 (SA).

C18:3 n-3 (linolenic acid) is converted by Δ9 elongase to 11,14,17 C20:3;

11,14,17 C20:3 is converted by Δ5-desaturase to Δ5cis-11,14,17-20:4 (JA).

Therefore, in a second aspect of the invention, there is provided a process for the production of a compound of general formula (I) as defined above and in which Y is:

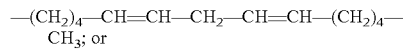

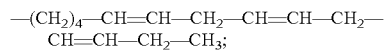

in an organism which comprises linoleic (C18:2 n-6) or linolenic (C18:3 n-3) acid, the process comprising introducing into the organism:

at least one nucleic acid sequence comprising:

a) SEQ ID NO: 1, SEQ ID NO: 3 or SEQ ID NO: 5;

b) a nucleic acid sequence which hybridizes under stringent conditions with a nucleic acid sequence of SEQ ID NO: 1, SEQ ID NO: 3 or SEQ ID NO: 5.

c) a nucleic acid sequence which encodes a polypeptide of SEQ ID NO:2, SEQ ID NO: 4 or SEQ ID NO: 6;

d) a derivative of a nucleic acid sequence of SEQ ID NO: 1, SEQ ID NO: 3 or SEQ ID NO: 5 which encodes a polypeptide with at least 40% identity at the amino acid level with SEQ ID NO: 2, SEQ ID NO: 4 or SEQ ID NO: 6, wherein said polypeptide has Δ5-desaturase activity;

and at least one nucleic acid sequence encoding a polypeptide having Δ9 elongase activity;

and expressing said nucleic acid sequences.

In the process of this aspect of the invention, the nucleic acid sequence encoding a polypeptide having Δ9 elongase activity may comprise a sequence encoding the C18-Δ9 elongase from *Isochrysis galbana* (SEQ ID NO: 25) or *Acanthamoeba castellanii* (SEQ ID NO: 24).

The processes according to the invention preferably yields total Δ5-unsaturated fatty acids in a content of at least 1% by weight, advantageously at least 3% by weight, based on the total fatty acids in the transgenic organisms, preferably in a transgenic plant.

The fatty acids are advantageously produced in bound form. These Δ5-unsaturated fatty acids can, with the aid of the nucleic acids used in the process according to the invention, be positioned at the sn1, sn2 and/or sn3 position of the advantageously produced triglycerides.

Since a plurality of reaction steps are performed by the starting compounds linoleic acid (C18:2) and linolenic acid (C18:3) in the process according to the second aspect of invention, the end products of the process such as, for example, sciadonic acid or juniperonic acid are not obtained as absolutely pure products; minor traces of the precursors are always present in the end product. If, for example, both linoleic acid and linolenic acid are present in the starting organism and the starting plant, the end products are present as mixtures.

Fatty acid esters or fatty acid mixtures produced by the process according to the invention advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acids which are present in the fatty acid esters or fatty acid mixtures are preferably at least 0.1, 0.2, 0.3, 0.4, 0.5, 0.6, 0.7, 0.8, 0.9 or 1% of arachidonic acid, based on the total fatty acid content. Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tariric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenyninic acid (9-octadecen-12-ynoic acid), 13,14-dihydrooropheic acid, octadecen-13-ene-9,11-diynoic acid, petroselenic acid (cis-6-octadecenoic acid), 9c, 12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c, 11t-octadecadienoic acid). The abovementioned fatty acids are, as a rule, advantageously only found in traces in the fatty acid esters or fatty acid mixtures produced by the process according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. In a further preferred form of the invention, these abovementioned fatty acids occur to less than 0.9%, 0.8%, 0.7%, 0.6% or 0.5%, especially preferably to less than 0.4%, 0.3%, 0.2%, 0.1%, based on the total fatty acids. The fatty acid esters or fatty acid mixtures produced by the process according to the invention advantageously comprise less than 0.1%, based on the total fatty acids, and/or no butyric acid, no cholesterol, no clupanodonic acid (=docosapentaenoic acid, $C22:5^{\Delta 4,8,12,15,21}$) and no nisinic acid (tetracosahexaenoic acid, $C23:6^{\Delta 3,8,12,15,18,21}$).

Chemically pure polyunsaturated fatty acids or fatty acid compositions can also be synthesized by the processes described above. To this end, the fatty acids or the fatty acid compositions are isolated from the organisms, such as the microorganisms or the plants or the culture medium in or on which the organisms have been grown, or from the organism and the culture medium, in the known manner, for example via extraction, distillation, crystallization, chromatography or a combination of these methods. These chemically pure fatty acids or fatty acid compositions are advantageous for applications in the food industry sector, the cosmetic sector and especially the pharmacological industry sector.

Suitable organisms for the production in the process according to the invention are, in principle, any organisms such as microorganisms, nonhuman animals or plants.

Plants which are suitable are, in principle, all those plants which are capable of synthesizing fatty acids, such as all dicotyledonous or monocotyledonous plants, algae or mosses. Advantageous plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Euglenaceae, Prasinophyceae or vegetable plants or ornamentals such as *Tagetes*.

Examples which may be mentioned are the following plants selected from the group consisting of: Adelotheciaceae such as the genera *Physcomitrella*, for example the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Camelina, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Camelina sativa, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae, such as the genera *Amphora, Cymbella, Okedenia, Phaeodactylum, Reimeria*, for example the genus and species *Phaeodactylum tricornutum*, Ditrichaceae, such as the genera Ditrichaceae, *Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpurascens, Ceratodon purpureus, Ceratodon purpureus* ssp. *convolutus, Ceratodon purpureus* ssp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium altemifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae, such as the genus *Elaeagnus*, for example the genus and species *Olea europaea* [olive], Ericaceae, such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euglenaceae, such as the genera *Ascoglena, Astasia, Colacium, Cyclidiopsis, Euglena, Euglenopsis, Hyalaphacus, Khawkinea, Lepocinclis, Phacus, Strombomonas, Trachelomonas*, for example the genus and species *Euglena gracilis*; Euphorbiaceae, such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [cassava] or *Ricinus communis* [castor-oil plant], Fabaceae, such as the genera *Pisum, Albizia, Cathormion, Feuillea, Inga, Pithecolobium, Acacia, Mimosa, Medicajo, Glycine, Dolichos, Phaseolus,* soybean, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbeck, Feuilleea lebbeck, Mimosa lebbeck, Mimosa speciosa, Medicago sativa, Medicago falcata, Medicago varia* [alfalfa] *Glycine max Dolichos soja, Glycine gracilis, Glycine hispida, Phaseolus max, Soja hispida* or *Soja max* [soybean], Funariaceae, such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella califomica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans califomica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elaeis*, for example the genus and species *Elaeis guineensis* [oil palm], Papaveraceae, such as, for example, the genus *Papaver*, for example the genera and species *Papaver orientale, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize] *Triticum aestivum, Tritcum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia*, for example the genus and species *Porphyridium cruentum*, Proteaceae, such as the genus *Macadamia*, for example the genus and species *Macadamia intergrfolia* [macadamia], Prasinophyceae, such as the genera *Nephroselmis, Prasinococcus, Scherffelia, Tetraselmis, Mantoniella, Ostreococcus*, for example the genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae, such as the genus *Coffea*, for example the genera and species *Coffea* spp., *Coffea arabica, Coffea canephora* or *Coffea liberica* [coffee], Scrophulariaceae, such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [verbascum], Solanaceae, such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant] *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea].

Advantageous microorganisms are, for example, fungi selected from the group of the families Chaetomiaceae, Choanephoraceae, Cryptococcaceae, Cunninghamellaceae, Demetiaceae, Moniliaceae, Mortierellaceae, Mucoraceae, Pythiaceae, Sacharomycetaceae, Saprolegniaceae, Schizosacharomycetaceae, Sodariaceae or Tuberculariaceae.

Examples of microorganisms which may be mentioned are those from the groups: Choanephoraceae, such as the genera *Blakeslea, Choanephora*, for example the genera and species *Blakeslea trispora, Choanephora cucurbitanum, Choanephora infundibulifera* var. *cucurbitanum*, Mortierellaceae, such as the genus *Mortierella*, for example the genera and species *Mortierella isabellina, Mortierella polycephala, Mortierella ramanniana, Mortierella vinacea, Mortierella zonata*, Pythiaceae, such as the genera *Phytium, Phytophthora*, for example the genera and species *Pythium debaryanum, Pythium intermedium, Pythium irregulare, Pythium megalacanthum, Pythium paroecandrum, Pythium sylvaticum, Pythium ultimum, Phytophthora cactonum, Phytophthora cinnamomi, Phytophthora citricola, Phytophthora citrophthora, Phytophthora cryptogea, Phytophthora drechsleri, Phytophthora erythroseptica, Phytophthora lateralis, Phytophthora megasperma, Phytophthora nicotianae, Phytophthora nicotianae* var. *parasitica, Phytophthora palmivora, Phytophthora parasitica, Phytophthora syringae*, Saccharomycetaceae, such as the genera *Hansenula, Pichia, Saccharomyces, Saccharomycodes, Yarrowia*, for example the genera and species *Hansenula anomala, Hansenula californica, Hansenula canadensis, Hansenula capsulata, Hansenula ciferrii, Hansenula glucozyma, Hansenula henricii, Hansenula holstii, Hansenula minuta, Hansenula nonfermentans, Hansenula philodendri, Hansenula polymorpha, Hansenula saturnus, Hansenula subpelliculosa, Hansenula wickerhamii, Hansenula wingei, Pichia alcoholophila, Pichia angusta, Pichia anomala, Pichia bispora, Pichia burtonii, Pichia canadensis, Pichia capsulata, Pichia carsonii, Pichia cellobiosa, Pichia ciferrii, Pichia farinosa, Pichia fermentans, Pichia finlandica, Pichia glucozyma, Pichia guilliermondii, Pichia haplophila, Pichia henricii, Pichia holstii, Pichia jadinii, Pichia lindnerii, Pichia membranaefaciens, Pichia methanolica, Pichia minuta* var. *minuta, Pichia minuta* var. *nonfermentans, Pichia norvegensis, Pichia ohmeri, Pichia pastoris, Pichia philodendri, Pichia pini, Pichia polymorpha, Pichia quercuum, Pichia rhodanensis, Pichia sargentensis, Pichia stipitis, Pichia strasburgensis, Pichia subpelliculosa, Pichia toletana, Pichia trehalophila, Pichia vini, Pichia xylosa, Saccharomyces aceti, Saccharomyces bailii, Saccharomyces bayanus, Saccharomyces bisporus, Saccharomyces capensis, Saccharomyces carlsbergensis, Saccharomyces cerevisiae, Saccharomyces cerevisiae* var. *ellipsoideus, Saccharomyces chevalieri, Saccharomyces delbrueckii, Saccharomyces diastaticus, Saccharomyces drosophilarum, Saccharomyces elegans, Saccharomyces ellipsoideus, Saccharomyces fermentati, Saccharomyces florentinus, Saccharomyces fragilis, Saccharomyces heterogenicus, Saccharomyces hienipiensis, Saccharomyces inusitatus, Saccharomyces italicus, Saccharomyces kluyveri, Saccharomyces krusei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces rosei, Saccharomyces rouxii, Saccharomyces uvarum, Saccharomycodes ludwigii, Yarrowia lipolytica*, Schizosacharomycetaceae such as the genera *Schizosaccharomyces* e.g. the species *Schizosaccharomyces japonicus* var. *japonicus, Schizosaccharomyces japonicus* var. *versatilis, Schizosaccharomyces malidevorans, Schizosaccharomyces octosporus, Schizosaccharomyces pombe* var. *malidevorans, Schizosaccharomyces pombe* var. *pombe*, Thraustochytriaceae such as the genera *Althomia, Aplanochytrium, Japonochytrium, Schizochytrium, Thraustochytrium* e.g. the species *Schizochytrium aggregatum, Schizochytrium limacinum, Schizochytrium mangrovei, Schizochytrium minutum, Schizochytrium octosporum, Thraustochytrium aggregatum, Thraustochytrium amoeboideum, Thraustochytrium antacticum, Thraustochytrium arudimentale, Thraustochytrium aureum, Thraustochytrium benthicola, Thraustochytrium globosum, Thraustochytrium indicum, Thraustochytrium kerguelense, Thraustochytrium kinnei, Thraustochytrium motivum, Thraustochytrium multirudimentale, Thraustochytrium pachydermum, Thraustochytrium proliferum*,

*Thraustochytrium roseum, Thraustochytrium rossii, Thraustochytrium striatum* or *Thraustochytrium visurgense*.

Further advantageous microorganisms are, for example, bacteria selected from the group of the families Bacillaceae, Enterobacteriacae or Rhizobiaceae.

Examples which may be mentioned are the following microorganisms selected from the group consisting of: Bacillaceae, such as the genus *Bacillus*, for example the genera and species *Bacillus acidocaldarius, Bacillus acidoterrestris, Bacillus alcalophilus, Bacillus amyloliquefaciens, Bacillus amylolyticus, Bacillus brevis, Bacillus cereus, Bacillus circulans, Bacillus coagulans, Bacillus sphaericus* subsp. *fusiformis, Bacillus galactophilus, Bacillus globisporus, Bacillus globisporus* subsp. *marinus, Bacillus halophilus, Bacillus lentimorbus, Bacillus lentus, Bacillus licheniformis, Bacillus megaterium, Bacillus polymyxa, Bacillus psychrosaccharolyticus, Bacillus pumilus, Bacillus sphaericus, Bacillus subtilis* subsp. *spizizenii, Bacillus subtilis* subsp. *subtilis* or *Bacillus thuringiensis*; Enterobacteriacae such as the genera *Citrobacter, Edwardsiella, Enterobacter, Erwinia, Escherichia, Klebsiella, Salmonella* or *Serratia*, for example the genera and species *Citrobacter amalonaticus, Citrobacter diversus, Citrobacter freundii, Citrobacter genomospecies, Citrobacter gillenii, Citrobacter intermedium, Citrobacter koseri, Citrobacter murliniae, Citrobacter* sp., *Edwardsiella hoshinae, Edwardsiella ictaluri, Edwardsiella tarda, Erwinia alni, Erwinia amylovora, Erwinia ananatis, Erwinia aphidicola, Erwinia billingiae, Erwinia cacticida, Erwinia cancerogena, Erwinia carnegieana, Erwinia carotovora* subsp. *atroseptica, Erwinia carotovora* subsp. *betavasculorum, Erwinia carotovora* subsp. *odorifera, Erwinia carotovora* subsp. *wasabiae, Erwinia chrysanthemi, Erwinia cypripedii, Erwinia dissolvens, Erwinia herbicola, Erwinia mallotivora, Erwinia milletiae, Erwinia nigrifluens, Erwinia nimipressuralis, Erwinia persicina, Erwinia psidii, Erwinia pyrifoliae, Erwinia quercina, Erwinia rhapontici, Erwinia rubrifaciens, Erwinia salicis, Erwinia stewartii, Erwinia tracheiphila, Erwinia uredovora, Escherichia adecarboxylata, Escherichia anindolica, Escherichia aurescens, Escherichia blattae, Escherichia coli, Escherichia coli* var. *communior, Escherichia coli-mutabile, Escherichia ferguson, Escherichia hermannii, Escherichia* sp., *Escherichia vulneris, Klebsiella aerogenes, Klebsiella edwardsii* subsp. *atlantae, Klebsiella omithinolytica, Klebsiella oxytoca, Klebsiella planticola, Klebsiella pneumoniae, Klebsiella pneumoniae* subsp. *pneumoniae, Klebsiella* sp., *Klebsiella terrigena, Klebsiella trevisanii, Salmonella abony, Salmonella arizonae, Salmonella bongori, Salmonella choleraesuis* subsp. *arizonae, Salmonella choleraesuis* subsp. *bongori, Salmonella choleraesuis* subsp. *cholereasuis, Salmonella choleraesuis* subsp. *diarizonae, Salmonella choleraesuis* subsp. *houtenae, Salmonella choleraesuis* subsp. *indica, Salmonella choleraesuis* subsp. *salamae, Salmonella daressalaam, Salmonella enterica* subsp. *houtenae, Salmonella enterica* subsp. *salamae, Salmonella enteritidis, Salmonella gallinarum, Salmonella heidelberg, Salmonella panama, Salmonella senftenberg, Salmonella typhimurium, Serratia entomophila, Serratia ficaria, Serratia fonticola, Serratia grimesii, Serratia liquefaciens, Serratia marcescens, Serratia marcescens* subsp. *marcescens, Serratia marinorubra, Serratia odorifera, Serratia plymouthensis, Serratia plymuthica, Serratia proteamaculans, Serratia proteamaculans* supsp. *quinovora, Serratia quinivorans* or *Serratia nubidaea*; Rhizobiaceae, such as the genera *Agrobacterium, Carbophilus, Chelatobacter, Ensifer, Rhizobium, Sinorhizobium*, for example the genera and species *Agrobacterium atlanticum, Agrobacterium ferrugineum, Agrobacterium gelatinovorum, Agrobacterium larrymoorei, Agrobacterium meteori, Agrobacterium radiobacter, Agrobacterium rhizogenes, Agrobacterium rubi, Agrobacterium stellulatum, Agrobacterium tumefaciens, Agrobacterium vitis, Carbophilus carboxidus, Chelatobacter heintzii, Ensifer adhaerens, Ensifer arboris, Ensifer fredii, Ensifer kostiensis, Ensifer kummerowiae, Ensifer medicae, Ensifer meliloti, Ensifer saheli, Ensifer terangae, Ensifer xinjiangensis, Rhizobium ciceri Rhizobium etli, Rhizobium fredii, Rhizobium galegae, Rhizobium gallicum, Rhizobium giardinii, Rhizobium hainanense, Rhizobium huakuii, Rhizobium huautlense, Rhizobium indigoferae, Rhizobium japonicum, Rhizobium leguminosarum, Rhizobium loessense, Rhizobium loti, Rhizobium lupini, Rhizobium mediterraneum, Rhizobium meliloti, Rhizobium mongolense, Rhizobium phaseoli, Rhizobium radiobacter, Rhizobium rhizogenes, Rhizobium rubi, Rhizobium sullae, Rhizobium tianshanense, Rhizobium trifolii, Rhizobium tropici, Rhizobium undicola, Rhizobium vitis, Sinorhizobium adhaerens, Sinorhizobium arboris, Sinorhizobium fredii, Sinorhizobium kostiense, Sinorhizobium kummerowiae, Sinorhizobium medicae, Sinorhizobium meliloti, Sinorhizobium morelense, Sinorhizobium saheli* or *Sinorhizobium xinjiangense*.

Further examples of advantageous microorganisms for the process according to the invention are protists or diatoms selected from the group of the families Dinophyceae, Turaniellidae or Oxytrichidae, such as the genera and species: *Crypthecodinium cohnii, Phaeodactylum tricornutum, Stylonychia mytilus, Stylonychia pustulata, Stylonychia putrina, Stylonychia notophora, Stylonychia* sp., *Colpidium campylum* or *Colpidium* sp. Those which are advantageously applied in the process according to the invention are transgenic organisms such as fungi, such as *mortierella* or *thraustrochytrium*, yeasts such as *Saccharomyces* or *Schizosaccharomyces*, mosses such as *Physcomitrella* or *Ceratodon*, nonhuman animals such as *Caenorhabditis*, algae such as *Nephroselmis, Pseudoscourfielda, Prasinococcus, Scherffelia, Tetraselmis, Mantoniella, Ostreococcus, Crypthecodinium* or *Phaeodactylum* or plants such as dicotyledonous or monocotyledonous plants. Organisms which are especially advantageously used in the process according to the invention are organisms which belong to the oil-producing organisms, that is to say which are used for the production of oil, such as fungi, such as *Mortierella* or *Thraustochytrum*, algae such as *Nephroselmis, Pseudoscourfielda, Prasinococcus, Scherffelia, Tetraselmis, Mantoniella, Ostreococcus, Crypthecodinium, Phaeodactylum*, or plants, in particular plants, preferably oilseed or oil crop plants which comprise large amounts of lipid compounds, such as peanut, oilseed rape, canola, sunflower, safflower (*Carthamus tinctoria*), poppy, mustard, hemp, castor-oil plant, olive, sesame, *Calendula, Punica*, evening primrose, verbascum, thistle, wild roses, hazelnut, almond, macadamia, avocado, bay, pumpkin/squash, linseed, soybean, pistachios, borage, trees (oil palm, coconut or walnut) or arable crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred for the second aspect of the invention are plants which are high in C18:2- and/or C18:3-fatty acids, such as sunflower, safflower, tobacco, verbascum, sesame, cofton, pumpkin/squash, poppy, evening primrose, walnut, linseed, hemp or thistle. Very especially preferred plants are plants such as safflower, sunflower, poppy, evening primrose, walnut, linseed or hemp. It is also be advantageous for the above-described method according to the invention additionally to introduce, into the organism, further nucleic acids which encode enzymes of the fatty acid or lipid metabolism, in addition to the nucleic acids introduced in the processes of the first and second aspects of the invention.

Nucleic acids used in the process according to the invention are advantageously derived from plants such as algae, for example algae of the family of the Prasinophyceae such as the genera *Heteromastix, Mammella, Mantoniella, Micromonas, Nephroselmis, Ostreococcus, Prasinocladus, Prasinococcus, Pseudoscourfielda, Pycnococcus, Pyramimonas, Scherffelia* or *Tetraselmis* such as the genera and species *Heteromastix longifillis, Mamiella gilva, Mantoniella squamata, Micromonas pusilla, Nephroselmis olivacea, Nephroselmis pyriformis, Nephroselmis rotunda, Ostreococcus tauri, Ostreococcus* sp. *Prasinocladus ascus, Prasinocladus lubricus, Pycnococcus provasolii, Pyramimonas amylifera, Pyramimonas disomata, Pyramimonas obovata, Pyramimonas orientalis, Pyramimonas parkeae, Pyramimonas spinifera, Pyramimonas* sp., *Tetraselmis apiculata, Tetraselmis carteriaformis, Tetraselmis chui, Tetraselmis convolutae, Tetraselmis desikacharyi, Tetraselmis gracilis, Tetraselmis hazeni, Tetraselmis impellucida, Tetraselmis inconspicua, Tetraselmis levis, Tetraselmis maculata, Tetraselmis marina, Tetraselmis striata, Tetraselmis subcordiformis, Tetraselmis suecica, Tetraselmis tetrabrachia, Tetraselmis tetrathele, Tetraselmis verrucosa, Tetraselmis verrucosa fo. rubens* or *Tetraselmis* sp. or from algae of the family Euglenaceae such as the genera *Ascoglena, Astasia, Colacium, Cyclidiopsis, Euglena, Euglenopsis, Hyalophacus, Khawkinea, Lepocinclis, Phacus, Strombomonas* or *Trachelomonas*, such as the genera and species *Euglena acus, Euglena geniculata, Euglena gracilis, Euglena mixocylindracea, Euglena rostrifera, Euglena viridis, Colacium stentorium, Trachelomonas cylindrica* or *Trachelomonas volvocina*. The nucleic acids used are advantageously derived from algae of the genera *Euglena, Mantoniella* or *Ostreococcus*.

Further advantageous plants are algae such as *Isochrysis* or *Crypthecodinium*, algae/diatoms such as *Thalassiosira* or *Phaeodactylum*, mosses such as *Physcomitrella* or *Ceratodon*, or higher plants such as the *Primulaceae* such as *Aleuritia, Calendula stellata, Osteospermum spinescens* or *Osteospermum hyoseroides*, microorganisms such as fungi, such as *Aspergillus, Thraustochytrium, Phytophthora, Entomophthora, Mucor* or *Mortierella*, bacteria such as *Shewanella*, yeasts or animals such as nematodes such as *Caenorhabditis*, insects, frogs, abalone, or fish. The isolated nucleic acid sequences according to the invention are advantageously derived from an animal of the order of the vertebrates. Preferably, the nucleic acid sequences are derived from the classes of the Vertebrata; *Euteleostomi, Actinopterygii; Neopterygii; Teleostei; Euteleostei, Protacanthopterygii, Salmoniformes; Salmonidae* or *Oncorhynchus* or Vertebrata, *Amphibia, Anura, Pipidae, Xenopus* or Evertebrata such as Protochordata, Tunicata, Holothuroidea, Cionidae such as *Amaroucium constellatum, Botryllus schlosseri, Ciona intestinalis, Molgula citrina, Molgula manhattensis, Perophora viridis* or *Styela partita*. The nucleic acids are especially advantageously derived from fungi, animals, or from plants such as algae or mosses, preferably from the order of the Salmoniformes, such as the family of the Salmonidae, such as the genus *Salmo*, for example from the genera and species *Oncorhynchus mykiss, Trutta trutta* or *Salmo trutta fario*, from algae, such as the genera *Mantoniella* or *Ostreococcus*, or from the diatoms such as the genera *Thalassiosira* or *Phaeodactylum* or from algae such as *Crypthecodinium*.

In a preferred embodiment, the process furthermore comprises the step of obtaining a cell or an intact organism which comprises the nucleic acid sequences used in the process, where the cell and/or the organism is transformed with a nucleic acid sequence according to the invention which encodes the Δ5-desaturase, a gene construct or a vector as described above, alone or in combination with further nucleic acid sequences which encode proteins of the fatty acid or lipid metabolism. In a further preferred embodiment, this process furthermore comprises the step of obtaining the oils, lipids or free fatty acids from the organism or from the culture. The culture can, for example, take the form of a fermentation culture, for example in the case of the cultivation of microorganisms, such as, for example, *Mortierella, Thalassiosira, Mantoniella, Ostreococcus, Saccharomyces* or *Thraustochytrium*, or a greenhouse- or field-grown culture of a plant. The cell or the organism produced thus is advantageously a cell of an oil-producing organism, such as an oil crop, such as, for example, peanut, oilseed rape, canola, linseed, hemp, peanut, soybean, safflower, hemp, sunflowers or borage.

In the case of plant cells, plant tissue or plant organs, "growing" is understood as meaning, for example, the cultivation on or in a nutrient medium, or of the intact plant on or in a substrate, for example in a hydroponic culture, potting compost or on arable land.

For the purposes of the invention, "transgenic" or "recombinant" means with regard to, for example, a nucleic acid sequence, an expression cassette (=gene construct) or a vector comprising the nucleic acid sequence or an organism transformed with the nucleic acid sequences, expression cassettes or vectors according to the invention, all those constructions brought about by recombinant methods in which either a) the nucleic acid sequence according to the invention, or
b) a genetic control sequence which is operably linked with the nucleic acid sequence according to the invention, for example a promoter, or
c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original organism or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding Δ5-desaturase gene—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic organism or transgenic plant for the purposes of the invention is therefore understood as meaning, as above, that the nucleic acids used in the process are not at their natural locus in the genome of an organism, it being possible for the nucleic acids to be expressed homologously or heterologously. However, as mentioned, transgenic also means that, while the nucleic acids according to the invention are at their natural position in the genome of an organism, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic organisms are fungi such as *Mortierella* or *Phytophtora*, mosses such as *Physcomitrella*, algae such as *Mantoniella, Euglena, Crypthecodinium* or *Ostreococcus*, diatoms such as *Thalassiosira* or *Phaeodactylum*, or plants such as the oil crops.

Organisms or host organisms for the nucleic acids, the expression cassette or the vector used in the process according to the invention are, in principle, advantageously all organisms which are capable of synthesizing fatty acids, specifically unsaturated fatty acids, and/or which are suitable for the expression of recombinant genes. Examples which may be mentioned are plants such as *Arabidopsis*, Asteraceae such as *Calendula* or crop plants such as soybean, peanut, castor-oil plant, sunflower, maize, cotton, flax, oilseed rape, coconut, oil palm, safflower (*Carthamus tinctorius*) or cacao bean, microorganisms, such as fungi, for example the genus *Mortierella, Thraustochytrium, Saprolegnia, Phytophtora* or *Pythium*, bacteria, such as the genus *Escherichia* or *Shewanella*, yeasts, such as the genus *Saccharomyces*, cyanobacteria, ciliates, algae such as *Mantoniella, Euglena, Thalassiosira* or *Ostreococcus*, or protozoans such as dinoflagellates, such as Crypthecodinium. Preferred organisms are those which are naturally capable of synthesizing substantial amounts of oil, such as fungi, such as *Mortierella alpina, Pythium insidiosum, Phytophtora infestans*, or plants such as soybean, oilseed rape, coconut, oil palm, safflower, flax, hemp, castor-oil plant, Calendula, peanut, cacao bean or sunflower, or yeasts such as *Saccharomyces cerevisiae* with soybean, flax, oilseed rape, safflower, sunflower, *Calendula, Mortierella* or *Saccharomyces cerevisiae* being especially preferred. In principle, host organisms are, in addition to the abovementioned transgenic organisms, also transgenic animals, advantageously nonhuman animals, for example *C. elegans, Ciona intestinalis* or *Xenopus laevis*.

Further utilizable host cells are detailed in: Goeddel, Gene Expression Technology: Methods in Enzymology 185, Academic Press, San Diego, Calif. (1990).

Expression strains which can be used, for example those with a lower protease activity, are described in: Gottesman, S., Gene Expression Technology: Methods in Enzymology 185, Academic Press, San Diego, Calif. (1990) 119-128.

These include plant cells and certain tissues, organs and parts of plants in all their phenotypic forms such as anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant.

Transgenic plants which comprise the polyunsaturated fatty acids synthesized in the process according to the invention can advantageously be marketed directly without there being any need for the oils, lipids or fatty acids synthesized to be isolated. Plants for the process according to the invention are listed as meaning intact plants and all plant parts, plant organs or plant parts such as leaf, stem, seeds, root, tubers, anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant. In this context, the seed comprises all parts of the seed such as the seed coats, epidermal cells, seed cells, endosperm or embryonic tissue. However, the compounds produced in the process according to the invention can also be isolated from the organisms, advantageously plants, in the form of their oils, fats, lipids and/or free fatty acids.

Polyunsaturated fatty acids produced by this process can be obtained by harvesting the organisms, either from the crop in which they grow, or from the field. This can be done via pressing or extraction of the plant parts, preferably the plant seeds. In this context, the oils, fats, lipids and/or free fatty acids can be obtained by what is known as cold-beating or cold-pressing without applying heat. To allow for greater ease of disruption of the plant parts, specifically the seeds, they are previously comminuted, steamed or roasted. The seeds which have been pretreated in this manner can subsequently be pressed or extracted with solvents such as warm hexane. The solvent is subsequently removed. In the case of microorganisms, the latter are, after harvesting, for example extracted directly without further processing steps or else, after disruption, extracted via various methods with which the skilled worker is familiar. In this manner, more than 96% of the compounds produced in the process can be isolated. Thereafter, the resulting products are processed further, i.e. refined. In this process, substances such as the plant mucilages and suspended matter are first removed. What is known as desliming can be effected enzymatically or, for example, chemicophysically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigment remaining in the product, the products are subjected to bleaching, for example using filler's earth or active charcoal. At the end, the product is deodorized, for example using steam.

The fatty acids produced by the processes of the present invention can be isolated from the organism in the form of an oil, a lipid or a free fatty acid. Suitable organisms are, for example, those mentioned above. Preferred organisms are transgenic plants. One embodiment of the invention is therefore oils, lipids or fatty acids of formula I or fractions thereof which have been produced by the above-described process, especially preferably oil, lipid or a fatty acid composition comprising a compound of formula I and being derived from transgenic plants.

As described above, these oils, lipids or fatty acids advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms.

Advantageous polyunsaturated fatty acids which are present in the fatty acid esters or fatty acid mixtures are preferably at least 0.1, 0.2, 0.3, 0.4, 0.5, 0.6, 0.7, 0.8, 0.9 or 1% of arachidonic acid, based on the total fatty acid content. Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyocta-deca-9,11-dienoic acid), vemolic acid (9,10-epoxyoctadec-12-enoic acid), tariric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenyninic acid (9-octadecen-12-ynoic acid), 13,14-dihydrooropheic acid, octadecen-13-ene-9,11-diynoic acid, petroselenic acid (cis-6-ctadecenoic acid), 9c, 12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c, 11 t-octadecadienoic acid). The abovementioned fatty acids are, as a rule, advantageously only found in traces in the fatty acid esters or fatty acid mixtures produced by the process according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. In a further preferred form of the invention, these abovementioned fatty acids occur to less than 0.9%, 0.8%, 0.7%, 0.6% or 0.5%, especially preferably to less than 0.4%, 0.3%, 0.2%, 0.1%, based on the total fatty acids. The fatty acid esters or fatty acid mixtures produced by the process according to the invention advantageously comprise less than 0.1%, based on the total fatty acids, and/or no butyric acid, no cholesterol, no clupanodonic acid (=docosapentaenoic acid, $C22:5^{\Delta 4,8,12,15,21}$) and no nisinic acid (tetracosahexaenoic acid, $C23:6^{\Delta 3,8,12,15,18,21}$).

A further embodiment according to the invention is the use of the oil, lipid, the fatty acids and/or the fatty acid composition in feedstuffs, foodstuffs, cosmetics or pharmaceuticals. The oils, lipids, fatty acids or fatty acid mixtures according to the invention can be used in the manner with which the skilled worker is familiar for mixing with other oils, lipids, fatty acids or fatty acid mixtures of animal origin, such as, for example, fish oils. These oils, lipids, fatty acids or fatty acid mixtures, which are composed of vegetable and animal constituents, may also be used for the preparation of feedstuffs, foodstuffs, cosmetics or pharmacologicals.

The term "oil", "lipid" or "fat" is understood as meaning a fatty acid mixture comprising unsaturated, saturated, preferably esterified, fatty acid(s). The oil, lipid or fat is preferably high in polyunsaturated free or, advantageously, esterified fatty acid(s), in particular linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid or docosahexaenoic acid.

The amount of unsaturated esterified fatty acids preferably amounts to approximately 30%, a content of 50% is more preferred, a content of 60%, 70%, 80% or more is even more preferred. For the analysis, the fatty acid content can, for example, be determined by gas chromatography after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism.

The Δ5-unsaturated fatty acids which are produced in the process are, as described above, for example sphingolipids, phosphoglycerides, lipids, glycolipids, phospholipids, monoacylglycerol, diacylglycerol, triacylglycerol or other fatty acid esters. Starting from the polyunsaturated fatty acids with advantageously at least five or six double bonds, which acids have been prepared in the process according to the invention, the polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the above-described processing step.

After their introduction into an organism, advantageously a plant cell or plant, the nucleic acids used in the process can either be present on a separate plasmid or, advantageously, integrated into the genome of the host cell. In the case of integration into the genome, integration can be random or else be effected by recombination such that the native gene is replaced by the copy introduced, whereby the production of the desired compound by the cell is modulated, or by the use of a gene in trans, so that the gene is linked operably with a functional expression unit which comprises at least one sequence which ensures the expression of a gene and at least one sequence which ensures the polyadenylation of a functionally transcribed gene. The nucleic acids are advantageously introduced into the organisms via multiexpression cassettes or constructs for multiparallel expression, advantageously into the plants for the multiparallel seed-specific expression of genes.

If microorganisms such as yeasts, such as *Saccharomyces* or *Schizosaccharomyces*, fungi such as *Mortierella, Aspergillus, Phytophtora, Entomophthora, Mucor* or *Thraustochytrium*, algae such as *Isochrysis, Mantoniella, Euglena, Ostreococcus, Phaeodactylum* or *Crypthecodinium* are used as organisms in the process according to the invention, these organisms are advantageously grown in fermentation cultures. If microorganisms are used as organisms in the process according to the invention, they are grown or cultured in the manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while passing in oxygen. The pH of the liquid medium can either be kept constant, that is to say regulated during the culturing period, or not. The cultures can be grown batchwise, semi-batchwise or continuously. Nutrients can be provided at the beginning of the fermentation or fed in semicontinuously or continuously. The polyunsaturated fatty acids produced can be isolated from the organisms as described above by processes known to the skilled worker, for example by extraction, distillation, crystallization, if appropriate precipitation with salt, and/or chromatography. To this end, the organisms can advantageously be disrupted beforehand.

If the host organisms are microorganisms, the process according to the invention is advantageously carried out at a temperature of between 0° C. and 95° C., preferably between 10° C. and 85° C., especially preferably between 15° C. and 75° C., very especially preferably between 15° C. and 45° C.

In this process, the pH value is advantageously kept between pH 4 and 12, preferably between pH 6 and 9, especially preferably between pH 7 and 8.

The process according to the invention can be operated batchwise, semibatchwise or continuously. An overview over known cultivation methods can be found in the textbook by Chmiel (Bioprozeβtechnik 1. Einführung in die Bioverfahrenstechnik [Bioprocess technology 1. Introduction to Bioprocess technology] (Gustav Fischer Verlag, Stuttgart, 1991)) or in the textbook by Storhas (Bioreaktoren und periphere Einrichtungen [Bioreactors and peripheral equipment] (Vieweg Verlag, Braunschweig/Wiesbaden, 1994)).

The culture medium to be used must suitably meet the requirements of the strains in question. Descriptions of culture media for various microorganisms can be found in the textbook "Manual of Methods fur General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of very good carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar raffination. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus. Chelating agents may be added to the medium in order to keep the metal ions in solution. Particularly suitable chelating agents include dihydroxyphenols such as catechol or protocatechuate and organic acids such as citric acid.

The fermentation media used according to the invention for culturing microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, comsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20 to 40° C. and preferably 25° C. to 40° C. The culture is continued until formation of the desired product is at a maximum. This aim is normally achieved within 10 to 160 hours.

The fermentation broths obtained in this way, in particular those containing polyunsaturated fatty acids, usually contain a dry mass of from 7.5 to 25% by weight. The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

The fatty acids obtained in the process are also suitable as starting material for the chemical synthesis of further products of interest. For example, they can be used in combination with one another or alone for the preparation of pharmaceuticals, foodstuffs, animal feeds or cosmetics.

All of the nucleic acid sequences used in the process according to the invention are advantageously derived from a eukaryotic organism such as a plant, a microorganism or an animal. The nucleic acid sequences are preferably derived from the order Salmoniformes, algae such as *Mantoniella, Crypthecodinium, Euglena* or *Ostreococcus*, fungi such as the genus *Phytophthora* or from diatoms such as the genera *Thalassiosira* or *Phaeodactylum*.

The invention furthermore relates to isolated nucleic acid sequences encoding polypeptides with Δ5-desaturase activity.

Therefore, in a further aspect of the invention there is provided an isolated nucleic acid sequence which encodes a polypeptide with Δ5-desaturase activity and which is selected from the group consisting of:

a) SEQ ID NO: 1, SEQ ID NO: 3 or SEQ ID NO: 5;
b) nucleic acid sequences which hybridize under stringent conditions with a nucleic acid sequence of SEQ ID NO: 1, SEQ ID NO: 3 or SEQ ID NO: 5.
c) an isolated nucleic acid sequence which encodes a polypeptide with Δ5-desaturase activity, wherein the polypeptide is selected from the group consisting of SEQ ID NO:2, SEQ ID NO: 4 or SEQ ID NO: 6;
d) A derivative of a nucleic acid sequence of SEQ ID NO: 1, SEQ ID NO: 3 or SEQ ID NO: 5 which encodes a polypeptide with at least 40% identity at the amino acid level with SEQ ID NO: 2, SEQ ID NO: 4 or SEQ ID NO: 6, wherein said polypeptide has Δ5-desaturase activity.

In still another aspect of the invention there is provided an amino acid sequence which is encoded by a nucleic acid sequence in (a), (b), (c) or (d) above.

Advantageously, the proteins encoded by these nucleic acid molecules have at least approximately 50%, preferably at least approximately 60% and more preferably at least approximately 70%, 80% or 90% and most preferably at least approximately 85%, 86%, 87%, 88%, 89%, 90%, 91%, 92%, 93%, 94%, 95%, 96%, 97%, 98%, 99% or more identity with the amino acid sequences shown in SEQ ID NO: 2, SEQ ID NO: 4 or SEQ ID NO: 6.

The nucleic acid sequences used in the process are advantageously introduced into an expression cassette which makes possible the expression of the nucleic acids in organisms such as microorganisms or plants.

Therefore, in another aspect of the invention there is provided a gene construct comprising a nucleic acid sequence which encodes a polypeptide with Δ5-desaturase activity as set out above, operably linked with one or more regulatory sequences.

In the expression cassette, the nucleic acid sequence which encode Δ5-desaturase, is linked operably with one or more regulatory sequences, advantageously for enhancing gene expression. These regulatory sequences are intended to make possible the specific expression of the genes and proteins. Depending on the host organism, this may mean, for example, that the gene is expressed and/or overexpressed only after induction has taken place, or else that it is expressed and/or overexpressed immediately. For example, these regulatory sequences take the form of sequences to which inductors or repressors bind, thus controlling the expression of the nucleic acid.

In addition to these novel regulatory sequences, or instead of these sequences, the natural regulatory elements of these sequences may still be present before the actual structural genes and, if appropriate, may have been genetically modified in such a way that their natural regulation is eliminated and the expression of the genes is enhanced. However, the expression cassette (=expression construct=gene construct) can also be simpler in construction, that is to say no additional regulatory signals have been inserted before the nucleic acid sequence or its derivatives, and the natural promoter together with its regulation was not removed. Instead, the natural regulatory sequence has been mutated in such a way that regulation no longer takes place and/or gene expression is enhanced. These modified promoters can also be positioned on their own before the natural gene in the form of part-sequences (=promotor with parts of the nucleic acid sequences used in accordance with the invention) in order to enhance the activity. Moreover, the gene construct may advantageously also comprise one or more what are known as enhancer sequences in operable linkage with the promoter, which make possible an enhanced expression of the nucleic acid sequence. Additional advantageous sequences, such as further regulatory elements or terminator sequences, may also be inserted at the 3' end of the DNA sequences. The Δ12-desaturase, ω3-desaturase, Δ4-desaturase, Δ5-desaturase, Δ6-desaturase, Δ8-desaturase, Δ5-elongase, Δ6-elongase and/or Δ9-elongase genes may be present in one or more copies of the expression cassette (=gene construct). Preferably, only one copy of the genes is present in each expression cassette. This gene construct or the gene constructs can be expressed together in the host organism. In this context, the gene construct(s) can be inserted in one or more vectors and be present in the cell in free form, or else be inserted in the genome. It is advantageous for the insertion of further genes in the genome when the genes to be expressed are present together in one gene construct.

In this context, the regulatory sequences or factors can, as described above, preferably have a positive effect on the gene expression of the genes introduced, thus enhancing it. Thus, an enhancement of the regulatory elements, advantageously at the transcriptional level, may take place by using strong transcription signals such as promoters and/or enhancers. In addition, however, enhanced translation is also possible, for example by improving the stability of the mRNA.

The regulatory sequences include, in particular, plant sequences such as promoter and terminator sequences. The constructs can advantageously be stably propagated in microorganisms, in particular in *E. coli* and *Agrobacterium tumefaciens*, under selective conditions and make possible the transfer of heterologous DNA into plants or microorganisms.

Useful regulatory sequences are present, for example, in promoters such as the cos, tac, trp, tet, trp-tet, lpp, lac, lpp-lac, laclq, T7, T5, T3, gal, trc, ara, SP6, λ-PR or λ-PL promoter and are advantageously employed in Gram-negative bacteria. Further advantageous regulatory sequences are, for example, present in the Gram-positive promoters amy and SPO2, in the yeast or fungal promoters ADC1, MFα, AC, P60, CYC1, GAPDH, TEF, rp28, ADH or in the plant promoters CaMV/ 35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzenesulfonamide-inducible), Plant J. 2, 1992:397-404 (Gatz et al., tetracycline-inducible), EP-Δ0 335 528 (abscissic acid-inducible) or WO 93/21334 (ethanol- or cyclohexenol-inducible) promoters. Further suitable plant promoters are the cytosolic FBPase promoter or the ST-LSI promoter of potato (Stockhaus et al., EMBO J. 8, 1989, 2445), the *glycine max* phosphoribosylpyrophosphate amidotransferase promoter (Genbank Accession No. U87999) or the node-specific promoter described in EP-A-0 249 676.

Especially advantageous promoters are promoters which make possible the expression in tissues which are involved in the biosynthesis of fatty acids. Very especially advantageous are seed-specific promoters, such as the USP promoter as described, but also other promoters such as the LeB4, DC3, phaseolin or napin promoter. Further especially advantageous promoters are seed-specific promoters which can be used for monocotyledonous or dicotyledonous plants and which are described in U.S. Pat. No. 5,608,152 (oilseed rape napin promoter), WO 98/45461 (*Arabidopsis* oleosin promoter), U.S. Pat. No. 5,504,200 (*Phaseolus vulgaris* phaseolin promoter), WO 91/13980 (*Brassica* Bce4 promoter), by Baeumlein et al., Plant J., 2, 2, 1992:233-239 (LeB4 promoter from a legume), these promoters being suitable for dicots. Examples of promoters which are suitable for monocots are the barley lpt-2 or lpt-1 promoter (WO 95/15389 and WO 95/23230), the barley hordein promoter and other suitable promoters described in WO 99/16890.

In principle, it is possible to use all natural promoters together with their regulatory sequences, such as those mentioned above. It is also possible and advantageous to use synthetic promoters, either in addition or alone, in particular when they mediate seed-specific expression, such as those described in WO 99/16890.

In order to achieve a particularly high Δ5-unsaturated fatty acid content, especially in transgenic plants, the Δ5-desaturase genes should advantageously be expressed in oil crops in a seed-specific manner. To this end, seed-specific promoters can be used, or those promoters which are active in the embryo and/or in the endosperm. In principle, seed-specific promoters can be isolated both from dicotyledonous and from monocotyledonous plants. Preferred promoters are listed hereinbelow: USP (=unknown seed protein) and vicilin (*Vicia faba*) [Bäumlein et al., Mol. Gen Genet., 1991, 225(3)], napin (oilseed rape) [U.S. Pat. No. 5,608,152], acyl carrier protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], legumines B4 (LegB4 promoter) [Bäumlein et al., Plant J., 2,2, 1992], Lpt2 and Ipt1 (barley) [WO 95/15389 and WO95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soybean) [EP 571 741], phosphoenol pyruvate carboxylase (soybean) [JP 06/62870], ADR12-2 (soybean) [WO 98/08962], isocitrate lyase (oilseed rape) [U.S. Pat. No. 5,689,040] or α-amylase (barley) [EP 781 849].

Plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic-acid-inducible promoter (WO 95/19443), a tetracycline-inducible promoter (Gatz et al. (1992) Plant J. 2, 397-404) and an ethanol-inducible promoter.

To ensure the stable integration of the biosynthesis genes into the transgenic plant over a plurality of generations, each of the nucleic acids which encode Δ12-desaturase, ω3-desaturase, Δ9-elongase, Δ6-desaturase, Δ8-desaturase, Δ6-elongase, Δ5-desaturase, Δ5-elongase and/or Δ4-desaturase and which are used in the process should be expressed under the control of a separate promoter, preferably a promoter which differs from the other promoters, since repeating sequence motifs can lead to instability of the T-DNA, or to recombination events. In this context, the expression cassette is advantageously constructed in such a way that a promoter is followed by a suitable cleavage site, advantageously in a polylinker, for insertion of the nucleic acid to be expressed and, if appropriate, a terminator sequence is positioned behind the polylinker. This sequence is repeated several times, preferably three, four or five times, so that up to five genes can be combined in one construct and introduced into the transgenic plant in order to be expressed. Advantageously, the sequence is repeated up to three times. To express the nucleic acid sequences, the latter are inserted behind the promoter via a suitable cleavage site, for example in the polylinker.

Advantageously, each nucleic acid sequence has its own promoter and, if appropriate, its own terminator sequence. Such advantageous constructs are disclosed, for example, in DE 101 02 337 or DE 101 02 338. However, it is also possible to insert a plurality of nucleic acid sequences behind a promoter and, if appropriate, before a terminator sequence. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoter, and different terminator sequences can be used in the expression cassette. However, it is also possible to use only one type of promoter in the cassette. This, however, may lead to undesired recombination events.

As described above, the transcription of the genes which have been introduced should advantageously be terminated by suitable terminator sequences at the 3' end of the biosynthesis genes which have been introduced (behind the stop codon). An example of a sequence which can be used in this context is the OCS 1 terminator sequence. As is the case with the promoters, different terminator sequences should be used for each gene.

Advantageously, in particular for the process of the second aspect of the invention, the gene construct additionally comprises a nucleic acid sequence encoding a polypeptide having Δ9-elongase activity, for example a sequence encoding the C18-Δ9 elongase from *Isochrysis galbana* (SEQ ID NO: 25) or *Acanthamoeba castellanii* (SEQ ID NO: 24)

The gene construct of the present invention may also comprise biosynthesis genes of the fatty acid or lipid metabolism selected from the group acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s) and desaturase(s) such as Δ4-desaturase, Δ5-desaturase, Δ6-desaturase, Δ8-desaturase, Δ9-desaturase, Δ12-desaturase or Δ6-elongase.

These additional nucleic acids or genes can be cloned into the expression cassettes, which are then used for transforming plants with the aid of vectors such as *Agrobacterium*.

Here, the regulatory sequences or factors can, as described above, preferably have a positive effect on, and thus enhance, the expression genes which have been introduced. Thus, enhancement of the regulatory elements can advantageously take place at the transcriptional level by using strong transcription signals such as promoters and/or enhancers. However, an enhanced translation is also possible, for example by improving the stability of the mRNA. In principle, the expression cassettes can be used directly for introduction into the plants or else be introduced into a vector. Therefore, in yet another aspect of the invention, there is provided a vector comprising a nucleic acid or a gene construct in any of the aspects of the invention described above.

In one embodiment, the vector may be a cloning vector.

The nucleic acid sequences of the invention may be introduced alone, or preferably, in combination with an expression cassette (nucleic acid construct) into an organism. To introduce the nucleic acids, the latter are advantageously amplified and ligated in the known manner. Preferably, a procedure following the protocol for Pfu DNA polymerase or a Pfu/Taq DNA polymerase mixture is followed. The primers are selected taking into consideration the sequence to be amplified. The primers should advantageously be chosen in such a way that the amplificate comprises the entire codogenic sequence from the start codon to the stop codon. After the amplification, the amplificate is expediently analyzed. For example, a gel-electrophoretic separation can be carried out, which is followed by a quantitative and a qualitative analysis. Thereafter, the amplificate can be purified following a standard protocol (for example Qiagen). An aliquot of the purified amplificate is then available for the subsequent cloning step.

Suitable cloning vectors are generally known to the skilled worker. These include, in particular, vectors which are capable of replication in microbial systems, that is to say mainly vectors which ensure efficient cloning in yeasts or fungi and which make possible the stable transformation of plants. Those which must be mentioned in particular are various binary and cointegrated vector systems which are suitable for the T-DNA-mediated transformation. Such vector systems are, as a rule, characterized in that they comprise at least the vir genes required for the Agrobacterium-mediated transformation and the T-DNA-delimiting sequences (T-DNA border). These vector systems advantageously also comprise further cis-regulatory regions such as promoters and terminator sequences and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, while a second one bears T-DNA, but no vir gene. Owing to this fact, the last-mentioned vectors are relatively small, easy to manipulate and to replicate both in *E. coli* and in *Agrobacterium*. These binary vectors include vectors from the series pBIB-HYG, pPZP, pBecks, pGreen. In accordance with the invention, Bin19, pBI101, pBinAR, pGPTV and pCAMBIA are used by preference. An overview of the binary vectors and their use is found in Hellens et al, Trends in Plant Science (2000) 5, 446-451. In order to prepare the vectors, the vectors can first be linearized with restriction endonuclease(s) and then modified enzymatically in a suitable manner. Thereafter, the vector is purified, and an aliquot is employed for the cloning step. In the cloning step, the enzymatically cleaved and, if appropriate, purified amplificate is cloned with vector fragments which have been prepared in a similar manner, using ligase. In this context, a particular nucleic acid construct, or vector or plasmid construct, can have one or else more than one codogenic gene segment. The codogenic gene segments in these constructs are preferably linked operably with regulatory sequences. The regulatory sequences include, in particular, plant sequences such as the above-described promoters and terminator sequences. The constructs can advantageously be stably propagated in microorganisms, in particular in *E. coli* and *Agrobacterium tumefaciens*, under selective conditions and make possible the transfer of heterologous DNA into plants or microorganisms.

The nucleic acids used in the process, the inventive nucleic acids and nucleic acid constructs, can be introduced into organisms such as microorganisms or advantageously plants, advantageously using cloning vectors, and thus be used in the transformation of plants such as those which are published and cited in: Plant Molecular Biology and Biotechnology (CRC Press, Boca Raton, Fla.), Chapter 6/7, p. 71-119 (1993); F. F. White, Vectors for Gene Transfer in Higher Plants; in: Transgenic Plants, Vol. 1, Engineering and Utilization, Ed.: Kung and R. Wu, Academic Press, 1993, 15-38; B. Jenes et al., Techniques for Gene Transfer, in: Transgenic Plants, Vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. Thus, the nucleic acids, the inventive nucleic acids and nucleic acid constructs, and/or vectors used in the process can be used for the recombinant modification of a broad spectrum of organisms, advantageously plants, so that the latter become better and/or more efficient producers of Δ5-unsaturated fatty acids. A series of mechanisms exist by which a modification of the Δ5-desaturase protein is possible, so that the yield, production and/or production efficiency of the advantageous Δ5-unsaturated fatty acids in a plant, preferably in an oil crop plant or a microorganism, can be influenced directly owing to this modified protein. The number or activity of the proteins or genes can be increased, so that greater amounts of the gene products and, ultimately, greater amounts of the compounds of the general formula I are produced. A de novo synthesis in an organism which has lacked the activity and ability to biosynthesize the compounds prior to introduction of the corresponding gene(s) is also possible. This applies analogously to the combination with further desaturases or elongases or further enzymes of the fatty acid and lipid metabolism. The use of various divergent sequences, i.e. sequences which differ at the DNA sequence level, may also be advantageous in this context, or else the use of promoters for gene expression which make possible a different gene expression in the course of time, for example as a function of the degree of maturity of a seed or an oil-storing tissue.

Owing to the introduction of a Δ5-desaturase gene into an organism, alone or in combination with other genes in a cell, it is not only possible to increase biosynthesis flux towards the end product, but also to increase, or to create de novo the corresponding triacylglycerol composition. Likewise, the number or activity of other genes which are involved in the import of nutrients which are required for the biosynthesis of one or more fatty acids, oils, polar and/or neutral lipids, can be increased, so that the concentration of these precursors, cofactors or intermediates within the cells or within the storage compartment is increased, whereby the ability of the cells to produce Δ5-unsaturated fatty acids as described below is enhanced further. By optimizing the activity or increasing the number of one or more Δ5-desaturase genes which are involved in the biosynthesis of these compounds, or by destroying the activity of one or more genes which are involved in the degradation of these compounds, an enhanced yield, production and/or efficiency of production of fatty acid and lipid molecules in organisms, advantageously in plants, is made possible.

Nucleic acids which can advantageously be used in the process are derived from bacteria, fungi, diatoms, animals such as *Caenorhabditis* or *Oncorhynchus* or plants such as algae or mosses, such as the genera *Shewanella, Physcomitrella, Thraustochytrium, Fusarium, Phytophthora, Ceratodon, Mantoniella, Ostreococcus, Isochrysis, Aleurita, Muscarioides, Mortierella, Borago, Phaeodactylum, Crypthecodinium*, specifically from the genera and species *Oncorhynchus mykiss, Xenopus laevis, Ciona intestinalis, Thalassiosira pseudonona, Mantoniella squamata, Ostreococcus* sp., *Ostreococcus tauri, Euglena gracilis, Physcomitrella patens, Phytophtora infestans, Fusarium graminaeum, Cryptocodinium cohnii, Ceratodon purpureus, Isochrysis galbana, Acanthamoeba castellanii, Aleurita farinosa, Thraustochytrium* sp., *Muscarioides viallii, Mortierella alpina, Borago officinalis, Phaeodactylum tricornutum, Caenorhabditis elegans* or especially advantageously from *Oncorhynchus mykiss, Euglena gracilis, Thalassiosira pseudonona* or *Crypthecodinium cohnii.*

In an alternative embodiment, the vector may be an expression vector designed to transform an organism in which the nucleic acid is to be expressed and the compound of formula I is synthesized.

These advantageous vectors, preferably expression vectors, comprise the nucleic acids which encode the Δ5-desaturase and which is used in the process of the first or second aspects As used in the present context, the term "vector" refers to a nucleic acid molecule which is capable of transporting another nucleic acid to which it is bound. One type of vector is a "plasmid", a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with bacterial replication origin). Other vectors are advantageously integrated into the genome of a host cell when they are introduced into the host cell, and thus replicate together with the host genome. Moreover, certain vectors can govern the expression of genes with which they are in operable linkage. These vectors are referred to in the present context as "expression vectors". Usually, expression vectors which are suitable for DNA recombination techniques take the form of plasmids.

In the present description, where the term "plasmid" is used, it should be understood that plasmids can be substituted for other types of expression vector, such as viral vectors, which exert similar functions. Furthermore, the term "vector" is also intended to comprise other vectors with which the skilled worker is familiar, such as phages, viruses such as SV40, CMV, TMV, transposons, IS elements, phasmids, phagemids, cosmids, linear or circular DNA.

The recombinant expression vectors advantageously used in the process comprise the nucleic acids described below or the above-described gene construct in a form which is suitable for expressing the nucleic acids used in a host cell, which means that the recombinant expression vectors comprise one or more regulatory sequences, selected on the basis of the host cells used for the expression, which regulatory sequence(s) is/are linked operably with the nucleic acid sequence to be expressed. In a recombinant expression vector, "linked operably" means that the nucleotide sequence of interest is bound to the regulatory sequence(s) in such a way that the expression of the nucleotide sequence is possible and they are bound to each other in such a way that both sequences carry out the predicted function which is ascribed to the sequence (for example in an in-vitro transcription/translation system, or in a host cell if the vector is introduced into the host cell). The term "regulatory sequence" is intended to comprise promoters, enhancers and other expression control elements (for example polyadenylation signals). These regulatory sequences are described, for example, in Goeddel: Gene Expression Technology: Methods in Enzymology 185, Academic Press, San Diego, Calif. (1990), or see: Gruber and Crosby, in: Methods in Plant Molecular Biology and Biotechnolgy, CRC Press, Boca Raton, Fla., Ed.: Glick and Thompson, Chapter 7, 89-108, including the references cited therein. Regulatory sequences comprise those which govern the constitutive expression of a nucleotide sequence in many types of host cell and those which govern the direct expression of the nucleotide sequence only in specific host cells under specific conditions. The skilled worker knows that the design of the expression vector can depend on factors such as the choice of host cell to be transformed, the desired expression level of the protein and the like.

The recombinant expression vectors used can be designed for the expression of Δ5-desaturase in prokaryotic or eukaryotic cells. This is advantageous since intermediate steps of the vector construction are frequently carried out in microorganisms for the sake of simplicity. For example, the Δ5-desaturase gene can be expressed in bacterial cells, insect cells (using Baculovirus expression vectors), yeast and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Ed., pp. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Ed., pp. 1-28, Cambridge University Press: Cambridge), algae (Falciatore et al., 1999, Marine Biotechnology. 1, 3:239-251), ciliates of the types: *Holotrichia, Peritrichia, Spirotrichia, Suctoria, Tetrahymena, Paramecium, Colpidium, Glaucoma, Platyophrya, Potomacus, Desaturaseudocohnilembus, Euplotes, Engelmaniella* and *Stylonychia*, in particular of the genus *Stylonychia lemnae*, using vectors in a transformation method as described in WO 98/01572 and, preferably, in cells of multi-celled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.:583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Vol. 1, Engineering and Utilization, Ed.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes involves the use of vectors comprising constitutive or inducible promoters which govern the expression of fusion or nonfusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) und pRIT5 (Pharmacia, Piscataway, N.J.), where glutathione S-transferase (GST), maltose-E binding protein and protein A, respectively, is fused with the recombinant target protein.

Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression from the pTrc vector is based on the transcription from a hybrid trlac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (DE3) from a resident λ-prophage which harbors a T7 gn1 gene under the transcriptional control of the lacUV 5 promoter.

Other vectors which are suitable for prokaryotic organisms are known to the skilled worker, these vectors are, for example in *E. coli* pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdC1, in *Streptomyces* pIJ101, pIJ364, pIJ702 or pIJ361, in *Bacillus* pUB110, pC194 or pBD214, in *Corynebacterium* pSA77 or pAJ667.

In a further embodiment, the expression vector is a yeast expression vector. Examples for vectors for expression in the yeast *S. cerevisiae* comprise pYeDesaturasec1 (Baldari et al. (1987) Embo J. 6:229-234), pMFa (Kudan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Ed., pp. 396-428: Academic Press: San Diego]. Further suitable yeast vectors are, for example, pAG-1, YEp6, YEp13 or pEMBLYe23.

As an alternative, Δ5-desaturase can be expressed in insect cells using Baculovirus vectors. Baculovirus expression vectors which are available for the expression of proteins in cultured insect cells (for example Sf9 cells) comprise the pAc series (Smith et al. (1983) Mol. Cell Biol. 3:2156-2165) and the pVL series (Lucklow and Summers (1989) Virology 170: 31-39).

The abovementioned vectors are only a small overview over suitable vectors which are possible. Further plasmids are known to the skilled worker and are described, for example, in: Cloning Vectors (Ed. Pouwels, P. H., et al., Elsevier, Amsterdam-New York-Oxford, 1985, ISBN 0 444 904018). For further suitable expression systems for prokaryotic and eukaryotic cells, see the Chapters 16 and 17 in Sambrook, J., Fritsch, E. F., and Maniatis, T., Molecular Cloning: A Laboratory Manual, 2. edition, Cold Spring Harbor Laboratory, Cold Spring Harbor Laboratory Press, Cold Spring Harbor, N.Y., 1989.

In a further embodiment of the process, the Δ5-desaturase can be expressed in single-celled plant cells (such as algae), see Falciatore et al., 1999, Marine Biotechnology 1 (3):239-251 and references cited therein, and in plant cells from higher plants (for example spermatophytes such as arable crops). Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38.

A plant expression cassette preferably comprises regulatory sequences which are capable of governing the expression of genes in plant cells and which are linked operably so that each sequence can fulfill its function, such as transcriptional termination, for example polyadenylation signals. Preferred polyadenylation signals are those which are derived from *Agrobacterium tumefaciens* T-DNA, such as gene 3 of the Ti plasmid pTiACH$_5$ (Gielen et al., EMBO J. 3 (1984) 835 et seq.), which is known as octopine synthase, or functional equivalents thereof, but all other terminator sequences which are functionally active in plants are also suitable.

Since plant gene expression is very often not limited to the transcriptional level, a plant expression cassette preferably comprises other sequences which are linked operably, such as translation enhancers, for example the overdrive sequence, which enhances the tobacco mosaic virus 5'—untranslated leader sequence, which increases the protein/RNA ratio (Gallie et al., 1987, Nucl. Acids Research 15:8693-8711).

As described above, plant gene expression must be linked operably with a suitable promoter which triggers gene expression with the correct timing or in a cell- or tissue-specific manner. Utilizable promoters are constitutive promoters (Benfey et al., EMBO J. 8 (1989) 2195-2202), such as those which are derived from plant viruses, such as 35S CaMV (Franck et al., Cell 21 (1980) 285-294), 19S CaMV (see also U.S. Pat. No. 5,352,605 and WO 84/02913), or plant promoters, such as the promoter of the Rubisco subunit, which is described in U.S. Pat. No. 4,962,028.

Other preferred sequences for use in operable linkage in plant gene expression cassettes are targeting sequences, which are required for steering the gene product into its corresponding cell compartment (see a review in Kermode, Crit. Rev. Plant Sci. 15, 4 (1996) 285-423 and references cited therein), for example into the vacuole, into the nucleus, all types of plastids, such as amyloplasts, chloroplasts, chromoplasts, the extracellular space, the mitochondria, the endoplasmic reticulum, elaioplasts, peroxisomes and other compartments of plant cells.

As described above, plant gene expression can also be achieved via a chemically inducible promoter (see review in Gatz 1997, Annu. Rev. Plant Physiol. Plant Mol. Biol., 48:89-108). Chemically inducible promoters are particularly suitable when it is desired that the gene expression takes place in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter.

Promoters which respond to biotic or abiotic stress conditions are also suitable, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

Especially preferred are those promoters which bring about the gene expression in tissues and organs in which the biosynthesis of fatty acids, lipids and oils takes place, in seed cells, such as cells of the endosperm and of the developing embryo. Suitable promoters are the oilseed rape napin promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumine B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable noteworthy promoters are the barley lpt2 or lpt1 gene promoter (WO 95/15389 and WO 95/23230) or the promoters from the barley hordein gene, the rice glutelin gene, the rice oryzin gene, the rice prolamine gene, the wheat gliadine gene, the wheat glutelin gene, the maize zeine gene, the oat glutelin gene, the sorghum kasirin gene or the rye secalin gene, which are described in WO 99/16890.

For the process of the second aspect, it may be desired to bring about the multiparallel expression of the Δ5-desaturase and the Δ9-elongase used in the process. Such expression cassettes can be introduced via the simultaneous transformation of a plurality of individual expression constructs or, preferably, by combining a plurality of expression cassettes on one construct. Also, a plurality of vectors can be transformed with in each case a plurality of expression cassettes and then transferred into the host cell.

Other promoters which are likewise especially suitable are those which bring about a plastid-specific expression, since plastids constitute the compartment in which the precursors and some end products of lipid biosynthesis are synthesized. Suitable promoters, such as the viral RNA polymerase promoter, are described in WO 95/16783 and WO 97/06250, and the clpP promoter from *Arabidopsis*, described in WO 99/46394.

Vector DNA can be introduced into prokaryotic and eukaryotic cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd ed., Cold Spring Harbor Laboratory, Cold Spring Harbor Laboratory Press, Cold Spring Harbor, N.Y., 1989) and other laboratory textbooks such as Methods in Molecular Biology, 1995, Vol. 44, *Agrobacterium* protocols, Ed.: Gartland and Davey, Humana Press, Totowa, N.J.

In a further aspect of the invention there is provided a transgenic non human organism comprising at least one nucleic acid, gene construct or vector according to a previous aspect of the invention.

The transgenic nonhuman organism may be a microorganism, a nonhuman animal or a plant.

Host cells which are suitable in principle for taking up the nucleic acid according to the invention, the gene product according to the invention or the vector according to the invention are all prokaryotic or eukaryotic organisms. The host organisms which are advantageously used are microorganisms such as fungi or yeasts, or plant cells, preferably plants or parts thereof. Fungi, yeasts or plants are preferably used, especially plants, for example plants such as oil crops, which are high in lipid compounds, such as oilseed rape, evening primrose, hemp, thistle, peanut, canola, linseed, soybean, safflower, sunflower, borage, or plants such as maize, wheat, rye, oats, triticale, rice, barley, cotton, cassava, pepper, Tagetes, Solanacea plants such as potato, tobacco, eggplant and tomato, *Vicia* species, pea, alfalfa, bushy plants (coffee, cacao, tea), *Salix* species, trees (oil palm, coconut), and perennial grasses and fodder crops. Especially preferred plants according to the invention are oil crops such as soybean, peanut, oilseed rape, canola, linseed, hemp, evening primrose, sunflower, safflower, trees (oil palm, coconut).

In an advantageous embodiment, the term "nucleic acid (molecule)" as used in the present context additionally comprises the untranslated sequence at the 3' and at the 5' end of the coding gene region: at least 500, preferably 200, especially preferably 100 nucleotides of the sequence upstream of the 5' end of the coding region and at least 100, preferably 50, especially preferably 20 nucleotides of the sequence downstream of the 3' end of the coding gene region. An "isolated" nucleic acid molecule is separate from other nucleic acid molecules which are present in the natural source of the nucleic acid. An "isolated" nucleic acid preferably has no sequences which naturally flank the nucleic acid in the genomic DNA of the organism from which the nucleic acid is derived (for example sequences which are located at the 5' and 3' ends of the nucleic acid ). In various embodiments, the isolated Δ12-desaturase, ω3-desaturase, Δ9-elongase, Δ6-desaturase, Δ8-desaturase, Δ6-elongase, Δ5-desaturase, Δ5-elongase or Δ4-desaturase molecule can comprise for example fewer than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived.

The nucleic acid molecules of the present invention, for example a nucleic acid molecule with a nucleotide sequence of SEQ ID NO: 1, SEQ ID NO: 3 or SEQ ID NO: 5 or of a part thereof can be isolated using molecular-biological standard techniques and the sequence information provided herein. Also, for example a homologous sequence or homologous, conserved sequence regions can be identified at the DNA or amino acid level with the aid of comparative algorithms. They can be used as hybridization probe and standard hybridization techniques (such as, for example, those described in Sambrook et al., Molecular Cloning: A Laboratory Manual. 2nd ed., Cold Spring Harbor Laboratory, Cold Spring Harbor Laboratory Press, Cold Spring Harbor, N.Y., 1989) for isolating further nucleic acid sequences which can be used in the process.

Moreover, a nucleic acid molecule comprising a complete sequence of SEQ ID NO: 1, SEQ ID NO: 3 or SEQ ID NO: 5 or a part thereof can be isolated by polymerase chain reaction, where oligonucleotide primers which are used on the basis of this sequence or parts thereof (for example a nucleic acid molecule comprising the complete sequence or part thereof can be isolated by polymerase chain reaction using oligonucleotide primers which have been generated based on this same sequence). For example, mRNA can be isolated from cells (for example by means of the guanidinium thiocyanate extraction method of Chirgwin et al. (1979) Biochemistry 18:5294-5299) and cDNA by means of reverse transcriptase (for example Moloney MLV reverse transcriptase, available from GibcotBRL, Bethesda, Md., or AMV reverse transcriptase, available from Seikagaku America, Inc., St. Petersburg, Fla.).

Synthetic oligonucleotide primers for the amplification by means of polymerase chain reaction can be generated based on one of the sequences shown in SEQ ID NO: 1, SEQ ID NO: 3 or SEQ ID NO: 5 or with the aid of the amino acid sequences detailed in SEQ ID NO: 2, SEQ ID NO: 4 and SEQ ID NO: 6.

A nucleic acid according to the invention can be amplified by standard PCR amplification techniques using cDNA or, alternatively, genomic DNA as template and suitable oligonucleotide primers. The nucleic acid amplified thus can be cloned into a suitable vector and characterized by means of DNA sequence analysis.

Oligonucleotides which correspond to a desaturase nucleotide sequence can be generated by standard synthetic methods, for example using an automatic DNA synthesizer.

The abovementioned nucleic acids and protein molecules with Δ5-desaturase activity are used in the process according to the invention for the modulation of the production of Δ5-unsaturated fatty acids in transgenic organisms, advantageously in plants, such as maize, wheat, rye, oats, triticale, rice, barley, soybean, peanut, cotton, *Linum* species such as linseed or flax, *Brassica* species such as oilseed rape, canola and turnip rape, pepper, sunflower, borage, evening primrose and *Tagetes*, Solanaceae plants such as potato, tobacco, eggplant and tomato, *Vicia* species, pea, cassava, alfalfa, bushy plants (coffee, cacao, tea), *Salix* species, trees (oil palm, coconut) and perennial grasses and fodder crops, either directly (for example when the overexpression or optimization of a fatty acid biosynthesis protein has a direct effect on the yield, production and/or production efficiency of the fatty acid from modified organisms) and/or can have an indirect effect which nevertheless leads to an enhanced yield, production and/or production efficiency of the Δ5-unsaturated fatty acids or a reduction of undesired compounds (for example when the modulation of the metabolism of lipids and fatty acids, cofactors and enzymes lead to modifications of the yield, production and/or production efficiency or the composition of the desired compounds within the cells, which, in turn, can affect the production of one or more fatty acids).

The combination of various precursor molecules and biosynthesis enzymes leads to the production of various fatty acid molecules, which has a decisive effect on lipid composition, since Δ5-unsaturated fatty acids are not only incorporated into triacylglycerol but also into membrane lipids.

Brassicaceae, Boraginaceae, Primulaceae, or Linaceae are particularly suitable for the production of PUFAs, for example steandonic acid, eicosapentaenoic acid and docosahexaenoic acid. Linseed (*Linum usitatissimum*) is especially advantageously suitable for the production of PUFAs with the nucleic acid sequences according to the invention, advantageously, as described, in combination with further desaturases and elongases.

Lipid synthesis can be divided into two sections: the synthesis of fatty acids and their binding to sn-glycerol-3-phosphate, and the addition or modification of a polar head group. Usual lipids which are used in membranes comprise phospholipids, glycolipids, sphingolipids and phosphoglycerides. Fatty acid synthesis starts with the conversion of acetyl-CoA into malonyl-CoA by acetyl-CoA carboxylase or into acetyl-ACP by acetyl transacylase. After condensation reaction, these two product molecules together form acetoacetyl-ACP, which is converted via a series of condensation, reduction and dehydratization reactions so that a saturated fatty acid molecule with the desired chain length is obtained. The production of the unsaturated fatty acids from these molecules is catalyzed by specific desaturases, either aerobically by means of molecular oxygen or anaerobically (regarding the fatty acid synthesis in microorganisms, see F. C. Neidhardt et al. (1996) *E. coli* and *Salmonella*. ASM Press: Washington, D.C., pp. 612-636 and references cited therein; Lengeler et al. (Ed.) (1999) Biology of Procaryotes. Thieme: Stuttgart, N.Y., and the references therein, and Magnuson, K., et al. (1993) Microbiological Reviews 57:522-542 and the references therein). To undergo the further elongation steps, the resulting phospholipid-bound fatty acids must be returned to the fatty acid CoA ester pool. This is made possible by acyl-CoA: lysophospholipid acyltransferases. Moreover, these enzymes are capable of transferring the elongated fatty acids from the CoA esters back to the phospholipids. If appropriate, this reaction sequence can be followed repeatedly.

Examples of precursors for the biosynthesis of sciadonic acid and juniperonic acid are linoleic acid and finolenic acid. The C18-carbon fatty acids must be elongated to C20 in order to obtain the required fatty acids and this can be achieved with a Δ9-elongase. With the aid of the Δ5-desaturases of the present invention, sciadonic acid and juniperonic acid can be produced and subsequently employed in various applications regarding foodstuffs, feedstuffs, cosmetics or pharmaceuticals.

The synthesized Δ5-unsaturated fatty acids are obtained in the process according to the invention in the form of the free fatty acid or in the form of their esters, for example in the form of their glycerides.

The term "glyceride" is understood as meaning glycerol esterified with one, two or three carboxyl radicals (mono-, di- or triglyceride). "Glyceride" is also understood as meaning a mixture of various glycerides. The glyceride or glyceride mixture may comprise further additions, for example free fatty acids, antioxidants, proteins, carbohydrates, vitamins and/or other substances.

For the purposes of the invention, a "glyceride" is furthermore understood as meaning glycerol derivatives. In addition to the above-described fatty acid glycerides, these also include glycerophospholipids and glyceroglycolipids. Preferred examples which may be mentioned in this context are the glycerophospholipids such as lecithin (phosphatidylcholine), cardiolipin, phosphatidylglycerol, phosphatidylserine and alkylacylglycerophospholipids.

Furthermore, fatty acids must subsequently be translocated to various modification sites and incorporated into the triacylglycerol storage lipid. A further important step in lipid synthesis is the transfer of fatty acids to the polar head groups, for example by glycerol fatty acid acyltransferase (see Frentzen, 1998, Lipid, 100(4-5):161-166).

Publications on plant fatty acid biosynthesis and on the desaturation, the lipid metabolism and the membrane transport of lipidic compounds, on beta-oxidation, fatty acid modification and cofactors, triacylglycerol storage and triacylglycerol assembly, including the references therein, see the following papers: Kinney, 1997, Genetic Engeneering, Ed.: J K Setlow, 19:149-166; Ohirogge and Browse, 1995, Plant Cell 7:957-970; Shanklin and Cahoon, 1998, Annu. Rev. Plant Physiol. Plant Mol. Biol. 49:611-641; Voelker, 1996, Genetic Engeneering, Ed.: J K Setlow, 18:111-13; Gerhardt, 1992, Prog. Lipid R. 31:397-417; Gühnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16.

Phospholipids for the purposes of the invention are understood as meaning phosphatidylcholine, phosphatidylethanolamine, phosphatidylserine, phosphatidylglycerol and/or phosphatidylinositol, advantageously phosphatidylcholine. The terms production or productivity are known in the art and comprise the concentration of the fermentation product (compounds of the formula I) which is formed within a specific period of time and in a specific fermentation volume (for example kg of product per hour per liter). It also comprises the productivity within a plant cell or a plant, that is to say the content of the desired fatty acids produced in the process relative to the content of all fatty acids in this cell or plant. The term production efficiency comprises the time required for obtaining a specific production quantity (for example the time required by the cell to establish a certain throughput rate of a fine chemical). The term yield or producticarbon yield is known in the art and comprises the efficiency of the conversion of the carbon source into the product (i.e. the fine chemical). This is usually expressed for example as kg of product per kg of carbon source. By increasing the yield or production of the compound, the amount of the molecules obtained of this compound, or of the suitable molecules of this compound obtained in a specific culture quantity over a specified period of time is increased. The terms biosynthesis or biosynthetic pathway are known in the art and comprise the synthesis of a compound, preferably an organic compound, by a cell from intermediates, for example in a multi-step and strongly regulated process. The terms catabolism or catabolic pathway are known in the art and comprise the cleavage of a compound, preferably of an organic compound, by a cell to give catabolites (in more general terms, smaller or less complex molecules), for example in a multi-step and strongly regulated process. The term metabolism is known in the art and comprises the totality of the biochemical reactions which take place in an organism.

The metabolism of a certain compound (for example the metabolism of a fatty acid) thus comprises the totality of the biosynthetic pathways, modification pathways and catabolic pathways of this compound in the cell which relate to this compound.

Owing to their homology to the Δ5-desaturase, nucleic acids disclosed here, nucleic acid molecules which are advantageous for the process according to the invention can be isolated following standard hybridization techniques under stringent hybridization conditions, using the sequences or part thereof as hybridization probe. In this context it is possible, for example, to use isolated nucleic acid molecules which are least 15 nucleotides in length and which hybridize under stringent conditions with the nucleic acid molecules which comprise a nucleotide sequence of The invention will now be described in greater detail with reference to the following Examples and to the drawings in which:

FIG. 1 is a comparison of the deduced amino acid sequences of A. leveillei and C. palustris desaturases AL10, AL21 and Cal2 with related sequences.

FIGS. 2 A-B depict a GC-MS analysis of fatty acid methyl esters derived from leaf tissue of wildtype Arabidopsis (FIG. 2A) or transgenie lines, expressing A. leveillei acyl-CoA desaturase AL21 (FIG. 2B). The presence of additional peaks is indicated with arrows. The figure shows that AL21 inserts Δ5-double bonds into a range of substrates.

FIGS. 3a-e show mass spectral identification of Δ5-fatty acids from transgenic Arabidopsis expressing A.leveillei acyl-Coa desaturase AL21: FIG. a) 18:1Δ5, FIG. b) authentic compound; FIG. c) 16:1Δ5; FIG. d) 18:3Δ5,9,12; FIG. e) authentic fatty acid derivative from a Pinus sp. Diagnostic ions are starred.

FIGS. 4A-B depict a comparison of Acyl-CoA profiles of trausgenic Arabidopsis expressing A. leveillei acyl-CoA desaturase AL21. Acyl-CoA poois of Arabidopsis leaves from wildtype plants (FIG. 4A) and AL21 transgenic plants (FIG. 4B) were analysed by HPLC. The presence of additional peaks is indicated with stars. The internal standard is 17:0. The figure shows that desaturation products (*) are present in the acyl-CoA pool.

FIGS. 5a-f is depict a series of GC profiles showing the expression of A. leveiliei acyl-CoA desaturases in transgenic Arabidopsis. Total fatty acid methyl esters derived from leaf tissue of wildtype Arabidopsis (FIG. 5a), Δ9 elongase line CA1-9 (FIG. 5b), double-transgenics CA1-9+AL21 (FIG. 5c and e) or CA1-9+ AL10 (FIG. 5d and f). C20 elongated products are marked with a star, Δ5-unsaturated fatty acids are indicated with solid arrows. The figure demonstrates that co-expression with Δ9 elongase reveals the function of A10 Δ5-desaturase.

FIG. 6 shows MS identification of 20:3Δ5,11,14 and 20:4Δ5, 11,14,17 from transgenic Arabidopsis plants co-expressing the A. leveillei acyl-CoA desaturases Al10 and Al21 and IgASE1.

FIG. 7 is a series of Acyl-CoA profiles of transgenic Arabidopsis co-expressing A. leveillei acyl-CoA desaturase AL21 and IgASE1. Acyl-CoA pools of Arabidopsis leaves from Δ9 elongase line CA1-9 (A) and double-transgenic CA1-9+AL10 plants (B) were analysed by HPLC. The presence of additional peaks is indicated with stars. The internal standard is 17:0. A 5-unsaturated fatty acids are indicated with solid arrows. The figure shows that C20 NMIFAs are present in the acyl-CoA pool of transgenic plants co-expressing Al10 and IgELO9.

FIG. 8 Functional expression in yeast in the presence of exogenous substrates.

FIGS. 9a-b show GC profiles of an A. thaliana leaf fatty acid methyl esers, extracted from a double transgenic plant expressing the A. leveillei Δ5-desaturase Al21 and I.galbana Δ9-elongase (FIG. 9a), or extracted from a single transgenic plant expressing the I. galbana Δ9-elongase (FIG. 9b).

Figure 2:
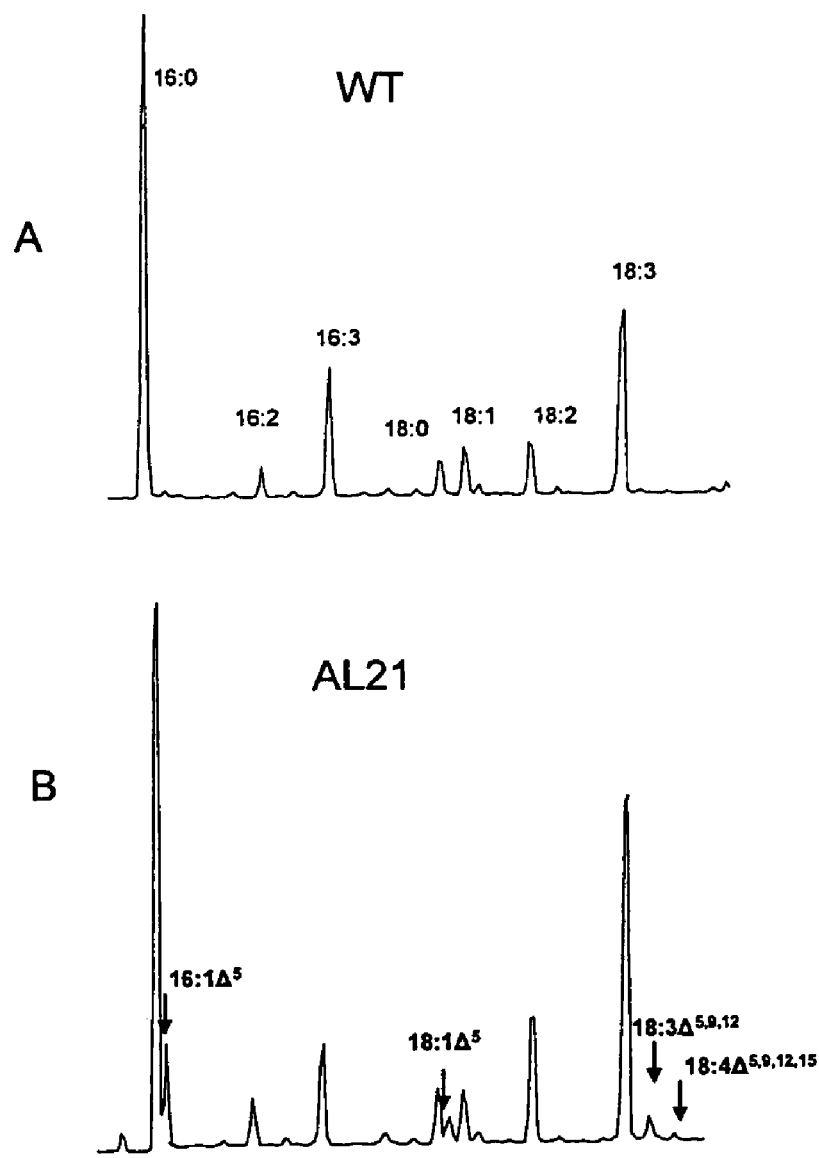

For reasons of clarity:
Al10 shall be identical to AlCoa10
Al21 shall be identical to AlCoa21
Cal2 shall be identical to CalCoa2

EXAMPLE 1

Materials and Methods.
Plant Material.
Seeds were obtained from Chiltern Seeds, Cumbria, UK.
Nucleic Acid Manipulation.
Total RNA was isolated from developing seeds of Anemone leveillei and Caltha palustris using the RNAeasy kit (Qiagen).
PCR-based Cloning.
Two degenerate primers were designed to conserved amino acid sequences corresponding to the histidine boxes and identified in previously characterized acyl-CoA desaturases: forward primer Des2F:

5'-TGGGTI(A/T)(G/C)IA(C/T)ICA(T/C)(C/A)GITA(T/C)CA(T/C)-

(SEQ ID NO 7) designed to encode histidine box II (WVSTHRYHHQF) and reverse primer DesR:

5'-GC(A/G)TG(A/G)TG(A/G)TT(A/G)TT(A/G)TGCCAICC(T/C)TCICC, (SEQ ID NO: 8) designed to encode the complement of histidine box III (GEGWHNNHHA), where I substitutes inosine.

These primers were used for PCR amplification with cDNAs transcribed from total RNA isolated from developing seeds of Anemone leveillei and Caltha palustris using previously described protocol (Sayanova et al, PNAS, 1997; 94: 4211-4216). The PCR fragments of the expected length (420 bp) were cloned into TOPO TA vector (Invitrogen) and sequenced. Data bank searches and alignments with these new sequences showed similarities to acyl-CoA desaturaseses for two different fragments from A. leveillei and one from C. palustris. The derived sequence data were used to design primers for the amplification of 5'- and 3' ends of putative desaturases using a SMART RACE cDNA Amplification kit (BD-Clontech).

The resulting 5'- and 3'-RACE products were used to amplify full-length copies of the two putative desaturases from cDNAs of *Anemone leveillei* designated Al10 (SEQ ID NO: 5) and Al21 (SEQ ID NO: 3) respectively and one putative desaturases from cDNAs of *Caltha palustris* designated Cal2 (SEQ ID NO: 1). Gene-specific primers were designed to the 5'- and 3'-ends of the coding regions of the corresponding desaturase sequences with restriction sites to facilitate cloning into plant vectors. The following pairs of forward/reverse (F/R) primers were used (restriction sites are indicated in bold).

```
Cal2:
                                        (SEQ ID NO: 9)
    SalF:    GGTCGACATGGCTCTAATTGCAACAACCCCCAAA;

(SEQ ID NO: 10)
    ClaF:    GATCGATATGGCTCTAATTGCAACAACCCCCAAA;

(SEQ ID NO: 11)
    SacR:    GAGCTCTTACTCGCTGAAACACATCC;

(SEQ ID NO: 12)
    ClaR:    GATCGATTTACTCGCTGAAACACATCC;

Al10
                                        (SEQ ID NO: 13)
    XbaF:    GGTCTAGAATGGATCTCACATCAATGG;

(SEQ ID NO: 14)
    NotF:    GGCGGCCGCATGGATCTCACATCAATGG;

(SEQ ID NO: 15)
    ClaF:    GATCGATATGGATCTCACATCAATGG;

(SEQ ID NO: 16)
    SalR:    GGTCGACTCAATTTTTGAAAGACATCTTACGCTTG;

(SEQ ID NO: 17)
    NotR:    GGCGGCCGCTCAATTTTTGAAAGACATCTTACGCTTG.

Al21
                                        (SEQ ID NO: 18)
    SmaF:    GGGCCCGGGATGGAACTCCCAGCGAT;

(SEQ ID NO: 19)
    NotF:    GGCGGCCGCATGGAACTCCCAGCGAT;

(SEQ ID NO: 20)
    ClaF:    GATCGATATGGAACTCCCAGCGAT;

(SEQ ID NO: 21)
    SalR:    GGTCGACTTACTTGTCGTTCACACAGAAC;

(SEQ ID NO: 22)
    NotR:    GGCGGCCGCTTACTTGTCGTTCACACAGAAC;

(SEQ ID NO: 23)
    ClaR:    GATCGATTTACTTGTCGTTCACACAGAAC.
```

Functional Expression in Yeast.

All coding regions corresponding to *A. leveillei* desaturases were inserted as Cla1/Cla1 fragments into the yeast pYES2.1 TOPO TA expression vector. Coding region corresponding to Isochrysis galbana C18-Δ9-elongase, ASE1, was inserted as a Kpn1-BamH1 fragment into the pYES3 expression vector. Forward primers were designed to contain a G at position −3 and +4 to improve translation initiation in eukaryotic cells. ORFs encoding putative desaturation activities were introduced in *S.cerevisiae* strain W303-1A by a lithium acetate method as previously described (Sayanova et al., 2003, FEBS Letters, 542,100-104). Cultures were grown at 22° C. in the presence of 2% (v/v) raffinose and expression of the transgenes was induced by the addition of galactose to 2% (w/v) in the presence of 0.5 mM of the corresponding fatty acid and 1% (w/v) tergitol-Nonidet P-40 (Sigma) as described. Yeast transformants containing pYES2-derived constructs were grown on synthetic minimal medium minus uracil; pYES3-derived constructs were grown on minimal medium minus tryptophan. Co-transformed yeast was grown on minimal medium minus uracil and tryptophan.

Plant Transformation Constructs.

All coding regions used were placed in CaMV 35S promoter—nos terminator expression cassettes. The coding regions of Al10 and Al21 were inserted as XbaI/SalI- and SmaI/SalI fragments respectively into the binary vector pBIN19-35S, kindly provided by Dr. P. Buchner.

The coding region of CalCoa2 was inserted as a SalI/SacI fragment into the vector pJD330 and excised with BamHI/XbaI for insertion into pBin19. For seed specific expression both coding regions of AlCoa10 and Alcoa21 were inserted as NotI fragments into expression vector pKMS2 (donated by Dr. E. Cahoon).

Plant Transformation.

Binary plasmids were transferred to *Agrobacterium tumifaciens* strain GV3101 by electroporation and kanamycin-resistant colonies were selected. Wild type *Arabidopsis thaliana* ecotype Columbia plants and transgenic *Arabidopsis* plants harbouring the Δ9-specific elongase from *Isochrysis galbana*, IgASE1 (Qi et al. 2004 Nature Biotechnology 22: 739-745), were transformed by the floral dipping method (Clough and Bent, 1998, Plant Journal 16: 735-743). Kanamycin-resistant plants for each construct were selected and transplanted to soil and analysed.

Fatty Acid Analysis.

Fatty acids were extracted and methylated as described (Sayanova et al., 2003, FEBS Letters, 542,100-104). Methyl ester derivatives of total fatty acids extracted from leaves were analysed by GC and GC-MS. For the determination of the double bond positions fatty acids methyl esters were converted to the 4,4-dimethyloxazoline (DMOX) derivatives (Fay and Richli, 1991, Journal of Chromatography 541: 89-98). The derivatives were submitted to gas chromatography-mass spectrometry (GC-MS), with a Hewlett Packard 5890 Series II plus gas chromatograph attached to an HP model 5989 MS engine. The latter was used in the electron impact mode at 70 eV with a source temperature of 250° C. The GC was fitted on-column injection, and was equipped with a capillary column of fused silica coated with Supelcowax 10TM (0.25 mm×25 m, 0.25 μm film; Supelco UK, Poole, UK). After holding the temperature at 80° C. for 3 min, the column was temperature-programmed at 20° C./min to 180° C., then at 2° C./min to 280° C., where it was held for 15 min. Helium was the carrier gas at a constant flow-rate of 1 mL/min.

Acyl-CoA Analysis.

For acyl-CoA analysis the method developed by Larson and Graham for plant tissues was used (Larson and Graham, 2001, Plant Journal 25: 115-125).

Results

Isolation of Putative acyl-CoA Desaturases from Ranunculaceae Species.

The seed oils of *A. leveillei* and *C. palustris* contain significant amounts of sciadonic acid. Therefore, the developing seed of these two species were used for RNA extraction and further analysis.

A PCR based approach was used to identify cDNAs for Δ5cis-desaturase. Degenerate primers (SEQ ID NO: 7 and SEQ ID NO: 8) designed to the histidine boxes identified in previously isolated putative acyl-CoA desaturases from rose and *Arabidopsis* were used.

The resulting 420 bp fragments were sequenced yielding two different types of sequences from *A. leveillei* and one type of sequence from *C. palustris*. All of them showed a high level of identity to putative acyl-CoA desaturase-like polypeptides from higher plants such as *Arabidopsis*; they also show some similarity to the partial sequence described by Cahoon et al (2000, Plant Physiology 124: 243 -251) for the *Limnanthes* Δ5-desaturase. These partial sequences were used to design 5' and 3'-RACE primers to amplify both ends of three putative acyl-CoA desaturases. Total RNA isolated from *A. leveillei* and *C. palustris* seeds was used as a template in all the RACE reactions. The sequence data acquired from 3' and 5 RACE were used to design primers to the 5' and 3'- ends of the coding regions of each of the three genes (SEQ ID NOS: 9-23). The primers also contained restriction sites to facilitate the cloning of these genes into the binary vectors for plant expression. Full-length copies of these cDNA clones were amplified directly from the corresponding cDNAs. These primers successfully amplified two full-sized cDNA clones from *A. leveillei*, designated Al10 (SEQ ID NO: 5) and Al21(SEQ ID NO: 3) and two cDNA clones from *C. palustris*, designated Cal1 and Cal2 (SEQ ID NO: 1). The cDNAs encode polypeptides of 378 (Cal1), 376 (Cal2, SEQ ID NO: 2), 312 (Al10, SEQ ID NO: 6) and 321 (Al21, SEQ ID NO: 6) amino acids. Polypeptides corresponding to cDNA clones Cal1 and Cal2 were almost identical except Cal1 contained an insertion of two amino acids at the position 60 (Leu Asp) (sequence not included). For further analysis we used cDNA clone Cal2. All four polypeptides were found to share up to 25% amino acid sequence identity with Δ9-acyl CoA desaturases from rat and human, but were most related to acyl-CoA desaturase like polypeptides from *L. douglasii*, rose and *Arabidopsis* (FIG. 1).

Expression of *A. leveillei* and *C. palustris* Putative Acyl-CoA Desaturases in *A. thaliana*.

Figure 3:
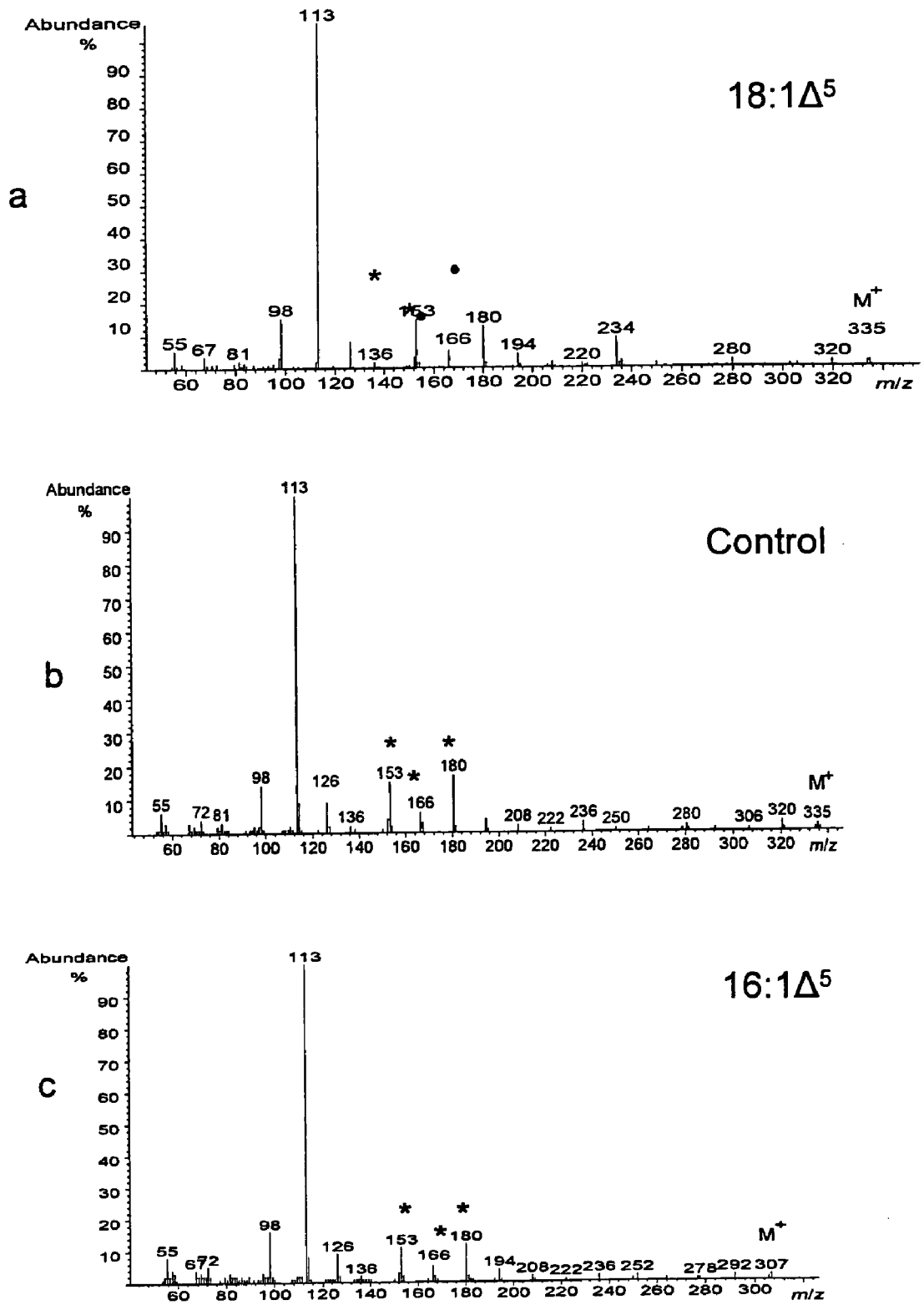

The coding regions for the three polypeptides, Cal2, Al10 and Al21, were introduced into plant expression vectors under the control of the CAMV 35S promoter and resulting constructs were used to transform *A. thaliana* plants. GC profiles of total fatty acids extracted from leaves of wild-type and transgenic plants transformed with Al10 and AL21 constructs show the presence of several mono- and polyunsaturated fatty acids that were not detected in wild type *Arabidopsis* (FIG. 2). These novel fatty acids were identified by GC-MS analysis of a DMOX derivatives of their methyl esters as previously described (Fay and Richli, 1991, Journal of Chromatography 541: 89-98). This confirmed their identities as Δ5 isomers of 16:1, 18:1, 18:3 and 18:4 fatty acids (FIG. 3). A double bond in position 5 in a DMOX derivative is usually characterized by a fingerprint of ions at m/z=153, 166, and 180. Thus, the double bond position of 18:1 was confirmed from the spectrum shown in FIG. 3a which can be compared with that of the authentic compound (FIG. 3b). 16:1Δ5 was essentially the same in the key region of the spectrum, differing only in the area of molecular ion (FIG. 3c). Fatty acid 18:3Δ5,9,12 was identified from comparisons of authentic spectra shown in FIG. 3d,e. The abundant ion at m/z=180 is highly characteristic of a 5,9-double bond system. MS analysis confirmed the presence of double bonds in positions 9 and 12 (located by gaps of 12 amu between m/z=194 and 206 and 234 and 246, respectively) and in the position 5, indicated by the especially abundant key diagnostic ion at m/z=180 representing cleavage at the centre of the bis-methylene-interrupted double bond system.

The most abundant of these fatty acids was 16:1 Δ5 which accounted for 1.8% (w/w) of the total fatty acids. The Δ5 isomers of 18:1, 18:3 and 18:4 each participated to less than 1% of the total fatty acids in the transgenic *Arabidopsis*. However, no Δ5-unsaturated fatty acids were found in transgenic *Arabidopsis* plants expressing Al10. Plants expressing Cal2 produced very small amounts of 16:0 (<1%).

Figure 4:
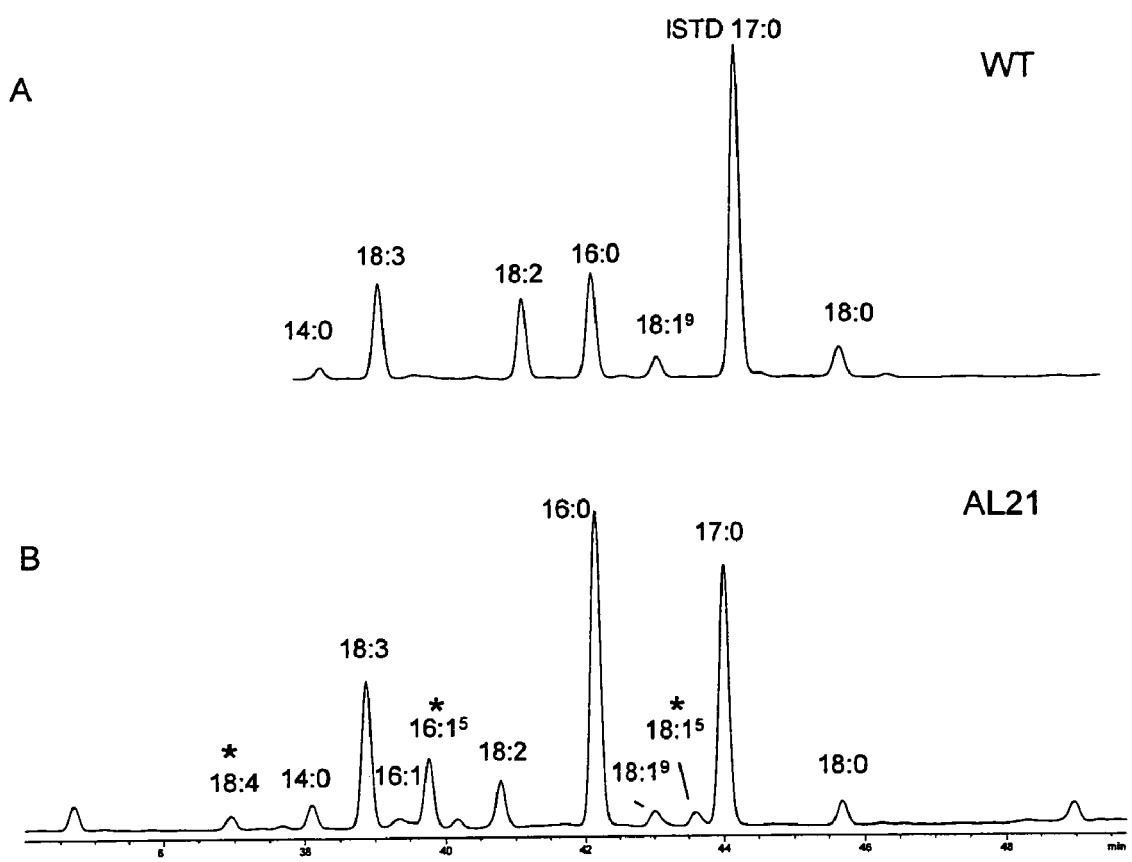

Analysis of the acyl-CoA pools of leaf tissues of *Arabidopsis* transformed with both constructs, Al10 and Al21 was carried out (FIG. 4). This revealed the presence of the Δ5-desaturated fatty acids corresponding to 16:1, 18:1 18:3 and 18:4 in transgenic plants, expressing Al21. Especially high were levels of 16:1Δ5 in transgenic plants expressing AL21. In the case of the acyl-CoA profiles for the leaves of the plants expressing AL10, the presence of the Δ5-desaturated fatty acids was not detected.

Co-expression of *A. leveillei* and *C. palustris* Acyl-CoA Desaturases in IgASE1 Transgenic *A. thaliana*.

Figure 5:
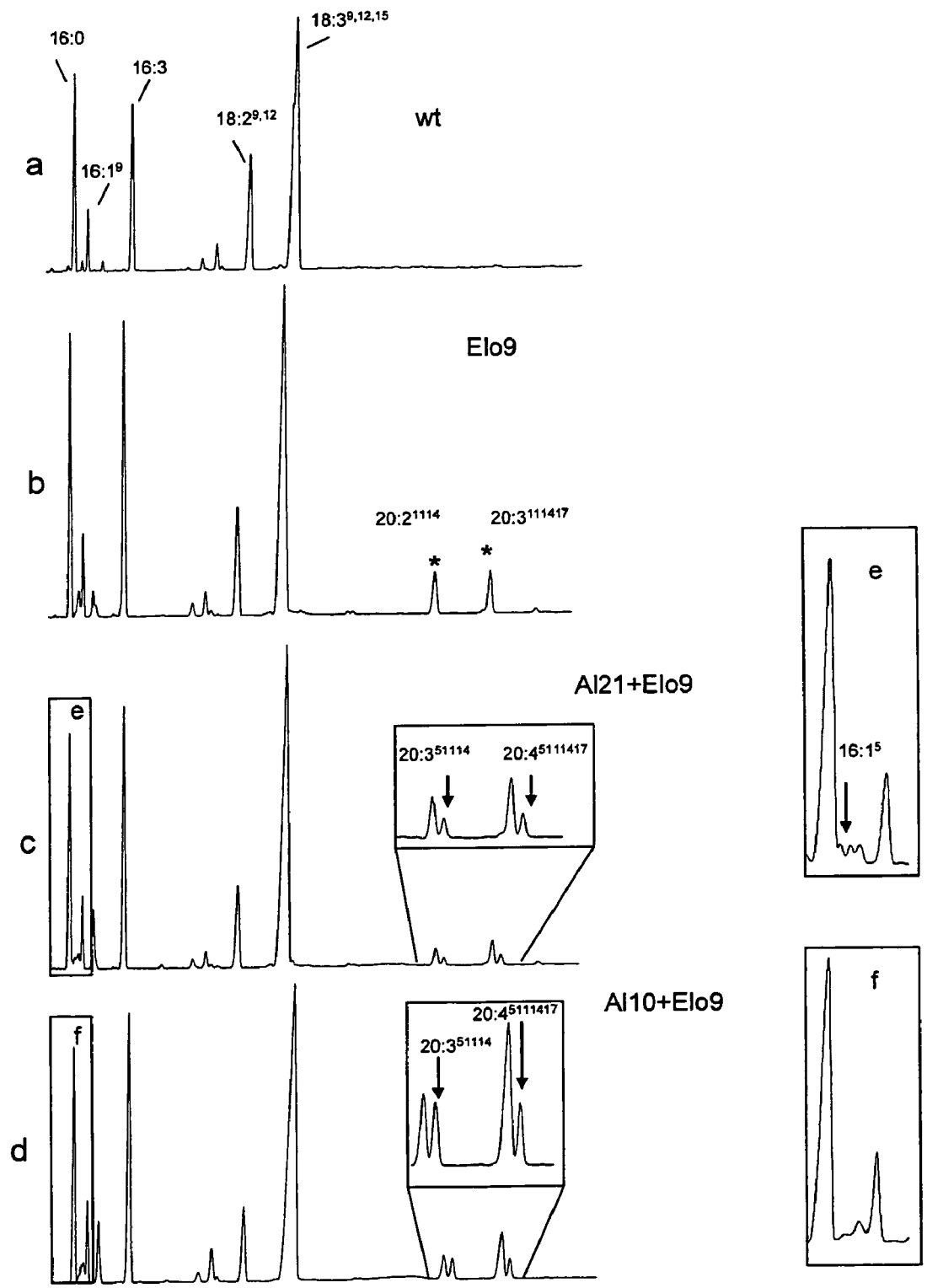
Figure 6:
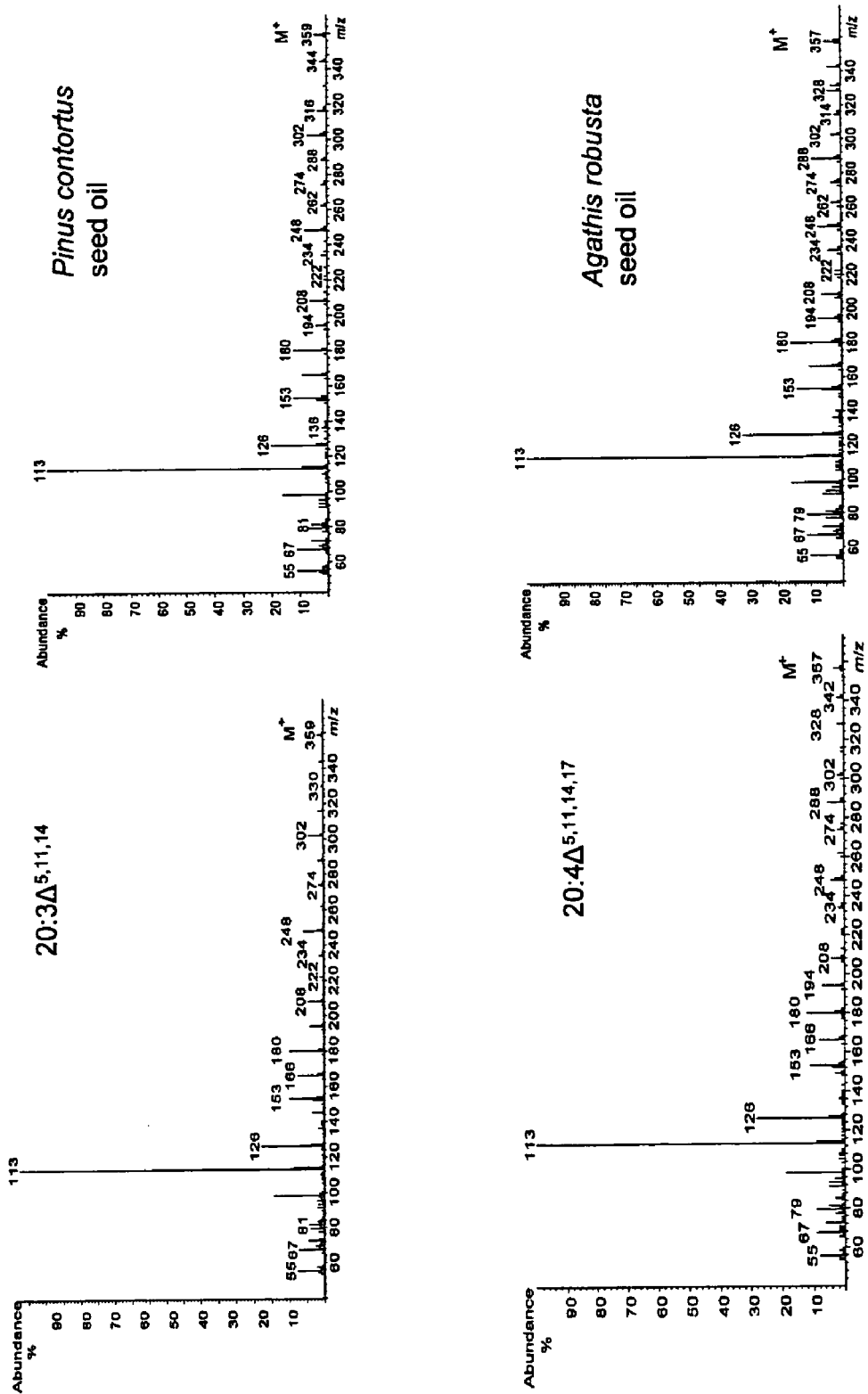

Since the synthesis of SA requires the presence of 20:2 n-6 as a substrate, we used *Arabidopsis* lines engineered to accumulate this fatty acid. Kanamycin resistance was used as a selectable marker in transformation of Liberty herbicide resistant IgASE1-line (which expresses the C18-Δ9-elongase from *Isochrysis galbana* (SEQ ID NO: 25) and therefore synthesises 20:2, n-6 and 20:3, n-3) with constructs containing *A. leveillei* and *C. palustris* acyl-CoA desaturases coding regions under the control of the CaMV 35S promoter. 40 independent double transgenic lines (i.e. BASTA and Kan resistant) for each of the constructs, AL10 and Al21, were obtained by *A. tumefaciens*-mediated transformation. Two additional peaks appeared in the GC profiles of the leaf fatty acids of the double transgenic lines harbouring both *A. leveillei* putative acyl-CoA desaturase activities, Al10 and Al21, compared to its single transgenic parent (FIG. 5). These were identified by GC-MS analysis as sciadonic acid (C20:3 Δ5cis, 11,14) and juniperonic acid (JA, C20:4 Δ5cis, 11,14,17), respectively, on the basis of the retention times of known standards and m/z (FIG. 6). GC-MS analysis of the leaf fatty acids of double transgenic *Arabidopsis* plants expressing AL21 also confirmed the presence of additional peak corresponding to 16:1 Δ5.

TABLE Ia

Total fatty acid composition of leaves from transgenic *A. thaliana* plants

| Fatty acids | 16:0 | 16:1$^5$ | 16:1$^9$ | 16:2 | 16:3 | 18:0 | 18:1 | 18:2 |
|---|---|---|---|---|---|---|---|---|
| Elo9 | 14.9 ± 0.8 | — | 3.8 ± 0.3 | 2.0 ± 0.1 | 19.4 ± 0.1 | 0.9 ± 0.1 | 1.6 ± 0.4 | 8.0 ± 1.0 |
| AL21 + Elo9 | 11.1 ± 0.3 | 0.6 ± 0.1 | 2.7 ± 0.4 | 2.5 ± 0.2 | 22.9 ± 0.8 | 0.5 ± 0.2 | 1.7 ± 0.3 | 5.2 ± 1.5 |
| AL10 + Elo9 | 13.4 ± 0.5 | — | 3.3 ± 0.2 | 3.4 ± 0.1 | 18.8 ± 1.5 | 0.6 ± 0.4 | 2.2 ± 0.2 | 5.3 ± 0.9 |

TABLE Ia-continued

Total fatty acid composition of leaves from transgenic A. thaliana plants

| Fatty acids | 18:3 | 20:2[11,14] | 20:3[5,11,14] | 20:3[11,14,17] | 20:4[5,11,14,17] |
|---|---|---|---|---|---|
| Elo9 | 47 ± 2.5 | 3.3 ± 1.5 | — | 3.8 ± 2.0 | — |
| AL21 + Elo9 | 42 ± 1.1 | 0.74 ± 0.3 | 0.5 ± 0.1 | 2.9 ± 1.0 | 1.3 ± 0.1 |
| AL10 + Elo9 | 43 ± 1.1 | 1.9 ± 0.4 | 1.5 ± 0.2 | 3.1 ± 1.1 | 1.4 ± 0.3 |

The values are mol % ± SD (n = 4).

SA and JA accounted for 0.5% and 1.3% of total fatty acids in plants expressing AL21 (Table Ia) and represented a conversion of 40% and 31% of their respective substrates. In plants expressing AL10 SA and JA accounted for 1.5% and 1.1% respectively and represented a conversion of 44% and 31% of their respective substrates. Single transgenic plants expressing Δ9-elongase activity accumulated C20:2 and C20:3 fatty acids to 3.3% and 3.8% of total fatty acids.

Figure 7:
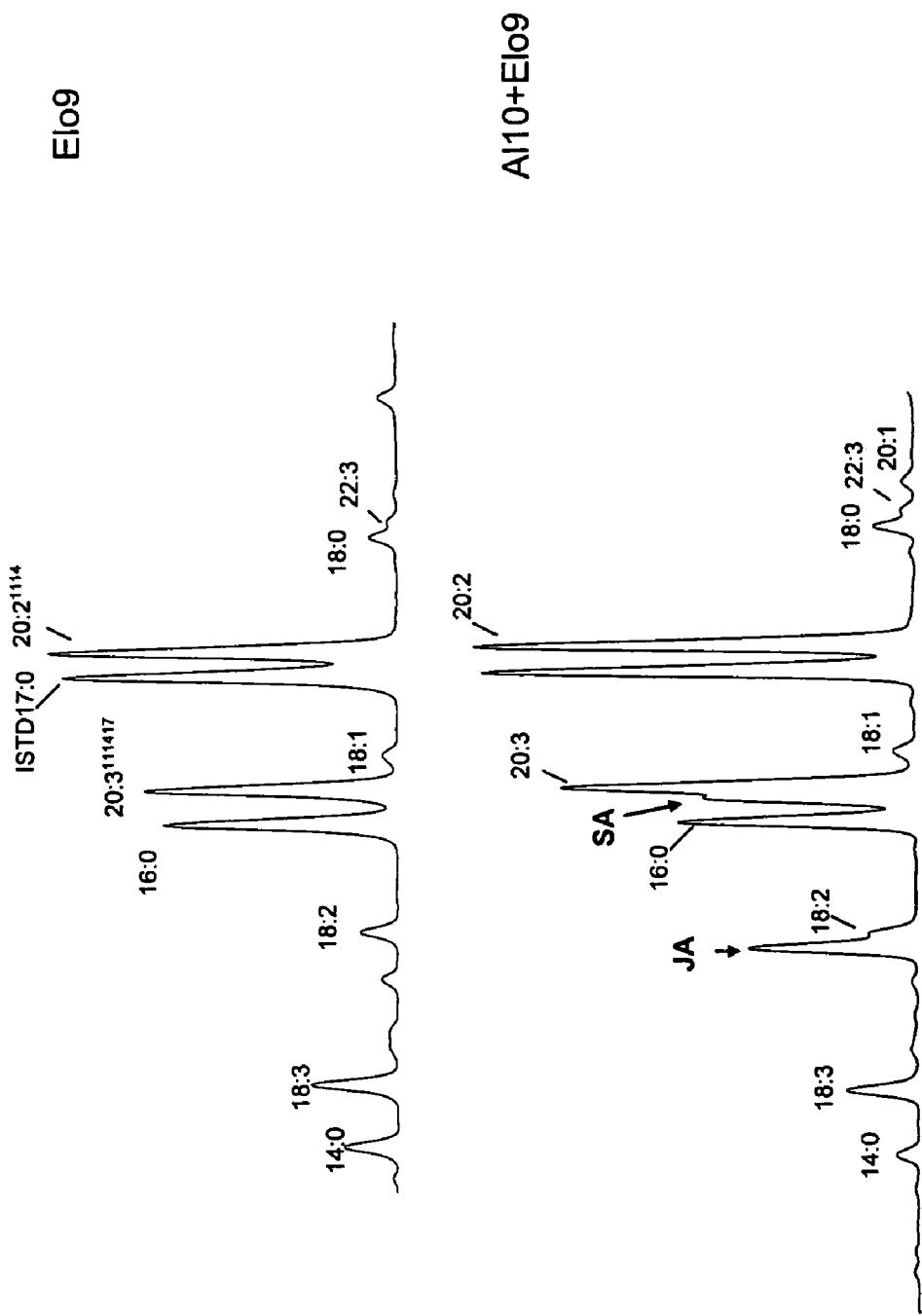

SA and JA accounted for 1% and 0.8% of total fatty acids (Table Ib) and represented a conversion of 53% and 44% of their respective substrates. Single transgenic plants expressing Δ9-eongase activity accumulated C20:2 and C20:3 fatty acids to 4.5% and 3.0% of total fatty acids, similar to those observed previously.

glycerolipids, and may imply they are poor substrates for endogenous *Arabidopsis* acyltransferases. When the acyl-CoA pool for lines co-expressing the IgASE1 elongase and *Anemone* desaturase were examined, considerable conversion of 20:2 and 20:3 to SA and JA was observed (see FIG. 7 for details). As has previously been observed with analysis of PUFA acyl-CoAs, separation of regioisomers is potentially difficult. However, SA accumulates as an overlapping peak with the 20:3 n-3 peak (i.e. the elongation product of ALA). In the case of JA, this elutes close to 18:2, and we reason that the JA peak is likely to be the larger of the two (based on retention time and no alteration to endogenous 18:2 fatty acid levels in these lines).

TABLE Ib

Total fatty acid composition of leaves from single and double transgenic A. thaliana plant

| Fatty acids | 16:0 | 16:1 | 16:2 | 16:3 | 18:0 | 18:1 | 18:2 | 18:3 | 20:2 | SA | 20:3 | JA |
|---|---|---|---|---|---|---|---|---|---|---|---|---|
| Al1028 | 14.0 | 4.0 | 0.74 | 13.8 | 1.6 | 3.6 | 12.65 | 45.7 | 0.8 | 0.92 | 1.0 | 0.8 |
| IgASE1 | 11.0 | 2.8 | 0. | 13.5.0 | 0.8 | 3.5 | 8.2 | 30.5 | 5.5 | — | 4.4 | — |

Acyl-CoA Profiling of Double- and Single-transgenic *A. thaliana* Plants.

Recent studies of PUFAs biosynthesis in transgenic plants suggest that the microsomal elongase uses acyl CoA as a substrate.

Functional Characterization of *A. leveillei* AL10 and AL21 Desaturases in Yeast.

The two full-length cDNAs corresponding to the two *A. leveillei* Al10 and Al21 ORFs were cloned in pYES2 vector and expressed in yeast under the control of galactose induc-

TABLE II

Fatty acid profile of the Acyl-CoA pool of a single and double transgenic A. thaliana. plants.

| FA | 16:0 | 18:0/22:3 | 18:1 | 18:2 | 18:2/JA | 18:3 | 20:0 | 20:1 | 20:2 | 20:3 | 20:3/SA |
|---|---|---|---|---|---|---|---|---|---|---|---|
| IgASE1 | 16.3 | 1.8 | 1.1 | 2.4 | — | 6.0 | 2.3 | 1.0 | 23.6 | 17.3 | — |
| Al1028 | 14.2 | 3.4 | 1.7 | — | 12.4 | 4.4 | 2.3 | 1.3 | 27.0 | — | 32.1 |

Figure 8:
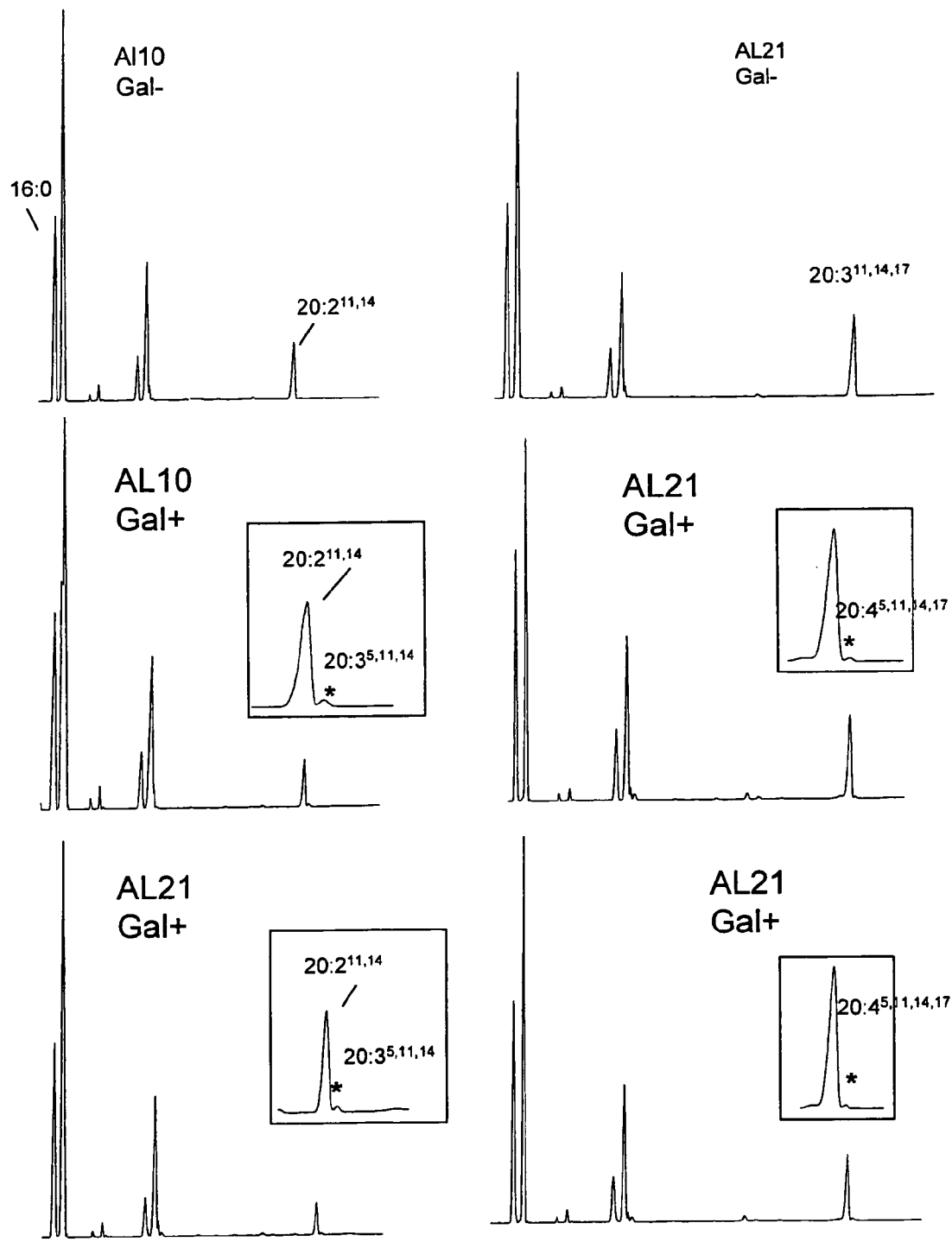
Figure 10:
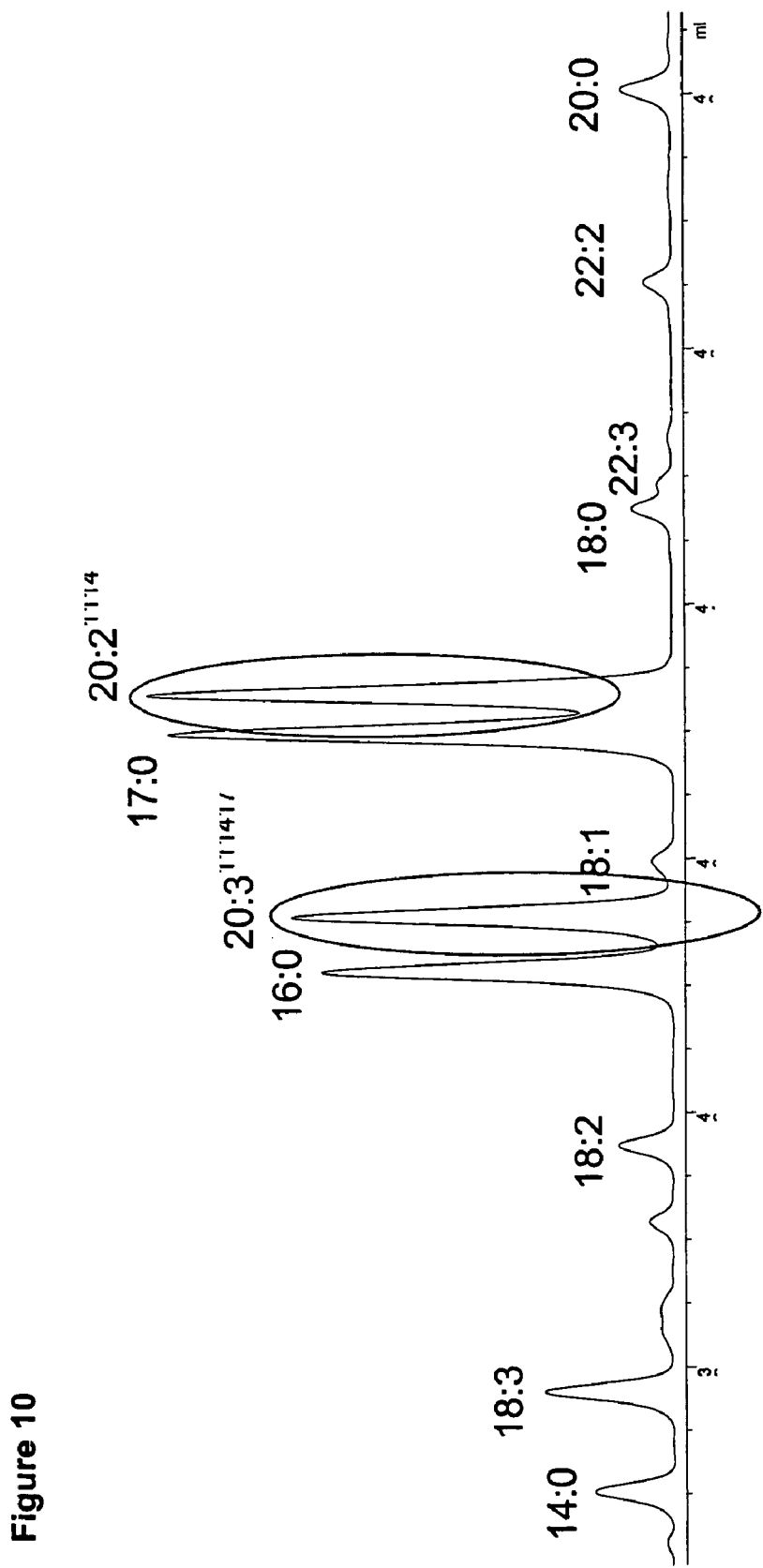
FIG. 10 shows an acyl CoA profile of an Arabidopsis single transgenic plant expressing IgASE1. The accumulation of 20:2 and 20:3 is observed, representing the elongation of LA and ALA, and the failure of these elongation products to accumulate in glycerolipids.
Figure 11:
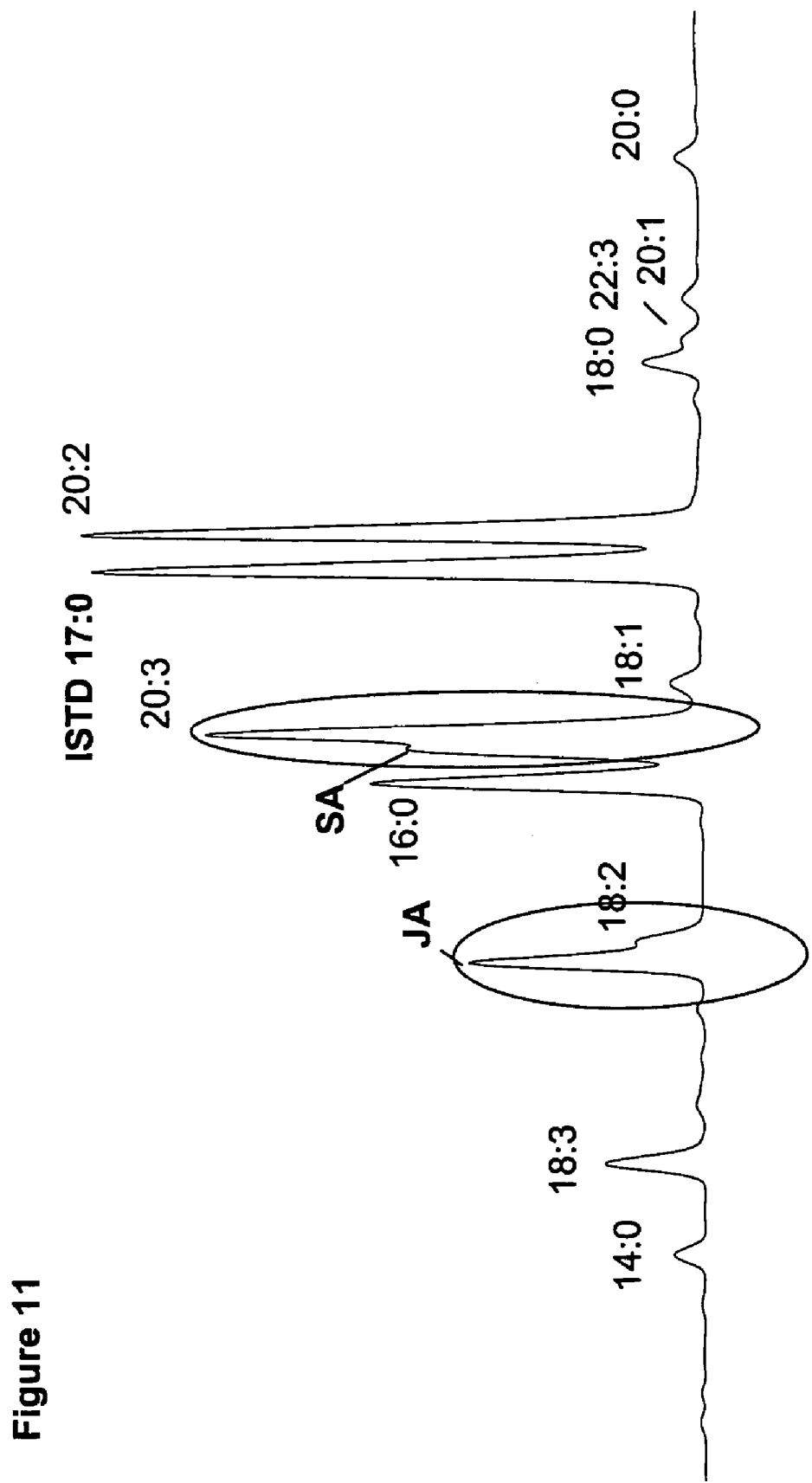
FIG. 11 shows an acyl CoA profile of a double transgenic plant expressing IgASE1 and A. leveillei Δ5-desaturase Al21.

Analysis of the acyl-CoA pool of the *Isochrysis galbana* Δ9 (IsoD9) elongase-containing transgenic plants (IgASE1) revealed the accumulation of high levels of acyl-CoAs representing the elongation products of linoleic acid (LA) and linolenic acid (ALA) (i.e. 20:2 n-6 and 20:3 n-3). These latter products represent potential substrates for the *Anemone* desaturase, especially if the enzyme utilises acyl-CoA substrates. it should also be noted that the accumulation of 20:2-CoA and 20:3-CoA in the IgASE1 lines is likely to represent poor transfer of the these esters from the CoA pool into ible GAL1 promoter in the presence of either 20:2 or 20:3 exogenous substrates. GC analysis of fatty acid methyl esters (FAMEs) revealed that transformed yeast cells were able to produce additional fatty acids that were not detected in controls. These fatty acids were identified by GC-MS-analysis as Δ5cis-20:3- and 20:4 NMIP-fatty acids. Each new putative Δ5-unsaturated fatty acid accounted for <1% of the total fatty acids of transgenic yeast (FIG. 8). To obtain higher levels of Δ5-unsaturated fatty acids in transgenic yeast we co-expressed both *A. leveilei* Δ5 desaturases with the C18-Δ9

PUFA-specific elongase IgASE1 from *Isochrysis galbana* in the presence of two different substrates, 18:2, n6 or 18:3, n-3. The results indicated that combination of elongation and desaturation activities has not generated better amounts of Sciadonic and Juniperonic acids in yeast (results not shown).

We therefore conclude that we have functionally indentified the Δ5-desaturase responsible for the NMI-desaturation and the synthesis of sciadonic and juniperonic acid. Moreover, we show that this enzyme is an acyl-CoA desaturase, and therefore represents the first cloned and characterised example of such an activity from higher plants. It is very likely that it would be possible to increase the accumulation of SA and JA in transgenic plants by optimising their exchange out of the acyl-CoA pool, by the co-expression of a suitable acyltransferases.

EXAMPLE 2

Generation of Transgenic Plants
a) Generation of Transgenic Oilseed Rape Plants (Modified Method of Moloney et al., 1992, Plant Cell Reports, 8:238-242)

Binary vectors in *Agrobacterium tumefaciens* C58C1: pGV2260 or *Escherichia coli* (Deblaere et al, 1984, Nucl. Acids. Res. 13, 4777-4788) can be used for generating transgenic oilseed rape plants. To transform oilseed rape plants (Var. Drakkar, NPZ Nordeutsche Pflanzenzucht, Hohenlieth, Germany), a 1:50 dilution of an overnight culture of a positively transformed agrobacterial colony in Murashige-Skoog medium (Murashige and Skoog 1962 Physiol. Plant. 15, 473) supplemented with 3% sucrose (3MS medium) is used. Petiools or hypocotyls of freshly germinated sterile oilseed rape plants (in each case approx. 1 cm$^2$) are incubated with a 1:50 agrobacterial dilution for 5-10 minutes in a Petri dish. This is followed by 3 days of coincubation in the dark at 25° C. on 3MS medium supplemented with 0.8% Bacto agar. The cultures are then grown for 3 days at 16 hours light/8 hours dark and the cultivation is continued in a weekly rhythm on MS medium supplemented with 500 mg/l Claforan (cefotaxim sodium), 50 mg/l kanamycin, 20 μM benzylaminopurine (BAP), now supplemented with 1.6 g/l of glucose. Growing shoots are transferred to MS medium supplemented with 2% sucrose, 250 mg/l Claforan and 0.8% Bacto agar. If no roots develop after three weeks, 2-indolebutyric acid was added to the medium as growth hornone for rooting. Regenerated shoots were obtained on 2MS medium supplemented with kanamycin and Claforan; after rooting, they were transferred to compost and, after growing on for two weeks in a controlled-environment cabinet or in the greenhouse, allowed to flower, and mature seeds were harvested and analyzed by lipid analysis for elongase expression, such as Δ5-elongase or Δ6-elongase activity or ω3-desaturase activity. In this manner, lines with elevated contents of polyunsaturated $C_{20}$- and $C_{22}$-fatty acids can be identified.

b) Generation of Transgenic Linseed Plants

Transgenic linseed plants can be generated for example by the method of Bell et al., 1999, In Vitro Cell. Dev. Biol.-Plant. 35(6):456-465 by means of particle bombardment. In general, linseed was transformed by an agrobacteria-mediated transformation, for example by the method of Mlynarova et al. (1994), Plant Cell Report 13: 282-285.

The invention claimed is:

1. A process for the production of a compound of formula (I):

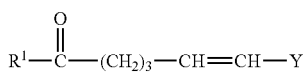

in an organism, the process comprising introducing into an organism which comprises a lipid of general formula (III):

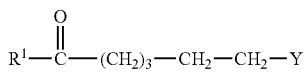

at least one nucleic acid sequence comprising:
 a) the nucleic acid sequence of SEQ ID NO: 3;
 b) a nucleic acid sequence which encodes the polypeptide of SEQ ID NO: 4; or
 c) a derivative of the nucleic acid sequence of SEQ ID NO: 3 which encodes a polypeptide with at least 85% identity at the amino acid level with SEQ ID NO: 4, wherein said polypeptide has Δ5-desaturase activity;
and expressing said nucleic acid sequence;
wherein, in general formulae (I) and (III):
 Y=a $C_{10}$-$C_{18}$ hydrocarbon chain containing up to four carbon-carbon double bonds;
 $R^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II:
 in which
  $R^2$=hydrogen, lysophosphatidyl choline, lysophosphatidylethanolamine, lysophos-phatidylglycerol, lyso-diphosphatidylglycerol, lysophosphatidylserine, lysophos-phatidylinositol or saturated or unsaturated $C_2$-$C_{24}$-alkylcarbonyl,
  $R^3$=hydrogen, saturated or unsaturated $C_2$-$C_{24}$-alkylcarbonyl, or $R^2$ and $R^3$ independently of one another are a radical of the formula Ia:

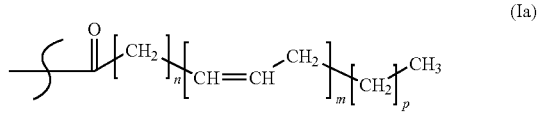

in which
 n=2, 3, 4, 5, 6, 7 or 9, m=2, 3, 4, 5 or 6 and p=0 or 3;
and wherein an oxygen in the $R^1$ radical may be replaced by sulphur such that $R^1$ is bonded to the remainder of the molecule via a thioester linkage.

2. A process as claimed in claim 1 wherein, in the compound of formula (I), the —CH=CH— double bond is in the cis orientation.

3. The process as claimed in claim 1 wherein, in the moiety Y, the carbon-carbon double bonds are in the cis orientation.

4. The process as claimed in claim 1, wherein in the compound of general formula (I) Y is:
—(CH$_2$)$_4$—CH═CH—CH$_2$—CH═CH—(CH$_2$)$_4$—CH$_3$, such that the compound of general formula (I) is sciadonic acid or a derivative thereof;
—(CH$_2$)$_4$—CH═CH—CH$_2$—CH═CH—CH$_2$—CH═CH—CH$_2$—CH$_3$, such that the compound of general formula (I) is juniperonic acid or a derivative thereof.

5. A process for the production of a compound of general formula (I) as defined in claim 1 and in which Y is:
—(CH$_2$)$_4$—CH═CH—CH$_2$—CH═CH—(CH$_2$)$_4$—CH$_3$; or
—(CH$_2$)$_4$—CH═CH—CH$_2$—CH═CH—CH$_2$—CH═CH—CH$_2$—CH$_3$;
in an organism which comprises linoleic (C18:2 n-6) or linolenic (C18:3 n-3) acid, the process comprising introducing into the organism:
at least one nucleic acid sequence comprising
 a) the nucleic acid sequence of SEQ ID NO: 3;
 b) a nucleic acid sequence which encodes the polypeptide of SEQ ID NO: 4; or
 c) a derivative of the nucleic acid sequence of SEQ ID NO: 3 which encodes a polypeptide with at least 85% identity at the amino acid level with SEQ ID NO: 4, wherein said polypeptide has Δ5-desaturase activity; and
at least one nucleic acid sequence encoding a polypeptide having Δ9 elongase activity;
and expressing said nucleic acid sequence.

6. The process as claimed in claim 5, wherein the nucleic acid sequence encoding a polypeptide having Δ9 elongase activity comprises a sequence encoding the C18-Δ9 elongase from *Isochrysis galbana* (SEQ ID NO: 25) or *Acanthamoeba castellanii* (SEQ ID NO: 24).

7. The process according to claim 1, wherein the substituents R$^2$ or R$^3$ independently of one another are saturated or unsaturated C$_{18}$-C$_{22}$-alkylcarbonyl.

8. The process according to claim 1, wherein the substituents R$^2$ or R$^3$ independently of one another are unsaturated C$_{18}$-, C$_{20}$- or C$_{22}$-alkylcarbonyl with at least two double bonds.

9. The process according to claim 1, wherein the organism is a microorganism or a plant.

10. The process according to claim 1, wherein the organism is an oil-producing plant, a vegetable plant or an ornamental.

11. The process according to claim 1, wherein the organism is a plant selected from the group of the plant families: Adelothe-ciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae or Prasinophyceae.

12. The process according to claim 1, wherein the compounds of the formula I are isolated from the organism in the form of their oils, lipids or free fatty acids.

13. The process according to claim 1, wherein the compounds of the formula I are isolated in a concentration of at least 1% by weight based on the total lipid content of the transgenic organism.

14. An isolated nucleic acid sequence which encodes a polypeptide with Δ5-desaturase activity and which comprises SEQ ID NO: 3.

15. An isolated nucleic acid sequence comprising a nucleic acid sequence which encodes a polypeptide with at least 85% identity at the amino acid level with SEQ ID NO: 4, wherein said polypeptide has Δ5-desaturase activity.

16. A gene construct comprising the nucleic acid sequence of claim 14, operably linked with one or more regulatory sequences.

17. The gene construct according to claim 16, further comprising a nucleic acid sequence encoding a polypeptide having Δ9-elongase activity.

18. The gene construct according to claim 17, wherein the nucleic acid sequence encoding a polypeptide having Δ9 elongase activity comprises a sequence encoding the C18-Δ9 elongase from *Isochrysis galbana* (SEQ ID NO: 25) or *Acanthamoeba castellanil* (SEQ ID NO: 24).

19. The gene construct according to claim 17, wherein the nucleic acid construct comprises additional biosynthesis genes of the fatty acid or lipid metabolism selected from the group acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s).

20. The gene construct according to claim 18, wherein the nucleic acid construct comprises additional biosynthesis genes of the fatty acid or lipid metabolism selected from the group Δ4-desaturase, Δ5-desaturase, Δ6-desaturase, Δ8-desaturase, Δ9-desaturase, Δ12-desaturase or Δ6-elongase.

21. A vector comprising the nucleic acid sequence of claim 14.

22. A transgenic organism comprising the nucleic acid sequence of claim 14, wherein the organism is a plant or microorganism.

23. The transgenic organism of claim 22, wherein the organism is a microorganism.

24. The transgenic organism of claim 22, wherein the organism is a plant.

25. A vector comprising the gene construct according to claim 16.

26. A transgenic organism comprising the gene construct of claim 16, wherein the organism is a plant or microorganism.

27. The transgenic organism of claim 26, wherein the organism is a plant.

28. A transgenic organism comprising the vector of claim 21, wherein the organism is a plant or microorganism.

29. The transgenic organism of claim 28, wherein the organism is a microorganism.

30. A transgenic organism comprising the nucleic acid sequence of claim 15, wherein the organism is a plant or microorganism.

* * * * *

UNITED STATES PATENT AND TRADEMARK OFFICE
CERTIFICATE OF CORRECTION

PATENT NO. : 7,723,574 B2
APPLICATION NO. : 11/603557
DATED : May 25, 2010
INVENTOR(S) : Thorsten Zank et al.

It is certified that error appears in the above-identified patent and that said Letters Patent is hereby corrected as shown below:

In the Claims:

In Claim 1, in column 68, on line 40, "or a radical of formula II:" should read

-- or a radical of formula II:

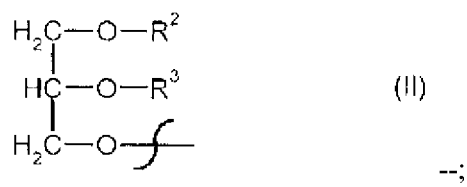

--;

In Claim 11, in column 69, on line 48, "lothe-ciaceae" should read -- lotheciaceae --;

In Claim 18, in column 70, on line 19, "castellanil" should read -- castellanii --.

Signed and Sealed this
Twenty-ninth Day of March, 2011

David J. Kappos
*Director of the United States Patent and Trademark Office*